(12) United States Patent
Zaborsky

(10) Patent No.: US 11,357,875 B2
(45) Date of Patent: *Jun. 14, 2022

(54) DISINFECTING METHODS AND APPARATUS

(71) Applicant: Inikoa Medical, Inc., Newark, CA (US)

(72) Inventor: Brett M. Zaborsky, Newark, CA (US)

(73) Assignee: INIKOA MEDICAL, INC., Newark, CA (US)

( * ) Notice: Subject to any disclaimer, the term of this patent is extended or adjusted under 35 U.S.C. 154(b) by 175 days.

This patent is subject to a terminal disclaimer.

(21) Appl. No.: 16/863,419

(22) Filed: Apr. 30, 2020

(65) Prior Publication Data
US 2020/0276342 A1    Sep. 3, 2020

Related U.S. Application Data

(63) Continuation of application No. 15/876,796, filed on Jan. 22, 2018, now Pat. No. 10,675,368, which is a
(Continued)

(51) Int. Cl.
*A61L 2/00* (2006.01)
*A61B 1/07* (2006.01)
(Continued)

(52) U.S. Cl.
CPC ............... *A61L 2/0023* (2013.01); *A61B 1/07* (2013.01); *A61L 2/0047* (2013.01); *A61L 2/08* (2013.01); *A61L 2/084* (2013.01); *A61L 2/10* (2013.01); *A61M 25/0026* (2013.01); *A61M 39/16* (2013.01); *A61M 39/28* (2013.01); *G01M 11/31* (2013.01); *G02B 6/02* (2013.01); *G02B 6/102* (2013.01); *A61L 2202/11* (2013.01); *A61L 2202/14* (2013.01); *A61L 2202/16* (2013.01); *A61L 2202/24* (2013.01);
(Continued)

(58) Field of Classification Search
CPC ..... A61B 1/07; A61L 2/08; A61L 2/10; A61L 2/0023
See application file for complete search history.

(56) References Cited

U.S. PATENT DOCUMENTS 4,412,834 A    11/1983  Kulin
5,260,020 A    11/1993  Wilk et al.
(Continued)

FOREIGN PATENT DOCUMENTS

WO    2014159874 A1    10/2014

OTHER PUBLICATIONS

International Search Report and Written Opinion in corresponding International Application No. PCT/US18/38199, dated Jul. 27, 2018 (6 pages).
(Continued)

*Primary Examiner* — Kevin Joyner
(74) *Attorney, Agent, or Firm* — Edell, Shapiro & Finnan, LLC

(57) ABSTRACT

According to one implementation a central venous catheter is provided that includes an end emitting optical fiber that is configured to end emit bacterial disinfecting light to disinfect a conduit located inside the hub, the conduit connecting the working lumen of an infusion shaft with a working lumen of a main shaft.

16 Claims, 76 Drawing Sheets

Related U.S. Application Data continuation-in-part of application No. 15/631,674, filed on Jun. 23, 2017, now Pat. No. 9,925,287, which is a continuation of application No. 15/629,494, filed on Jun. 21, 2017, now Pat. No. 9,925,285.

(51) Int. Cl.

| | | |
|---|---|---|
| *A61L 2/08* | (2006.01) | |
| *A61L 2/10* | (2006.01) | |
| *A61M 39/16* | (2006.01) | |
| *A61M 25/00* | (2006.01) | |
| *A61M 39/28* | (2006.01) | |
| *G02B 6/02* | (2006.01) | |
| *G02B 6/10* | (2006.01) | |
| *G01M 11/00* | (2006.01) | |
| *A61N 5/06* | (2006.01) | |

(52) U.S. Cl.
CPC ............. *A61M 2025/004* (2013.01); *A61M 2025/0019* (2013.01); *A61N 5/0624* (2013.01)

(56) References Cited

U.S. PATENT DOCUMENTS

| | | | |
|---|---|---|---|
| 5,637,877 A | 6/1997 | Sinofsky | |
| 5,695,482 A | 12/1997 | Kaldany | |
| 6,461,569 B1 | 10/2002 | Boudreaux | |
| 6,524,529 B1 | 2/2003 | Horton, III | |
| 6,564,087 B1 | 5/2003 | Pitris et al. | |
| 7,274,844 B2 | 9/2007 | Walt et al. | |
| 7,686,839 B2 | 3/2010 | Parker | |
| 8,197,087 B2 | 6/2012 | Sobue et al. | |
| 8,431,910 B1 | 4/2013 | Perry | |
| 8,556,950 B2 | 10/2013 | Rioux et al. | |
| 8,574,490 B2 | 11/2013 | Haytman et al. | |
| 8,632,576 B2 | 1/2014 | Quisenberry | |
| 8,702,640 B2 | 4/2014 | Dacey, Jr. et al. | |
| 8,706,211 B2 | 4/2014 | Dacey, Jr. et al. | |
| 8,953,914 B2 | 2/2015 | Genier | |
| 9,259,513 B2 | 2/2016 | Bedwell et al. | |
| 9,278,148 B2 | 3/2016 | Fewkes et al. | |
| 9,295,742 B2 | 3/2016 | Rasooly et al. | |
| 2002/0025097 A1 | 2/2002 | Cooper et al. | |
| 2002/0037133 A1 | 3/2002 | Unsworth | |
| 2003/0017073 A1 | 1/2003 | Eckhardt et al. | |
| 2005/0175658 A1 | 8/2005 | Dimauro et al. | |
| 2005/0279354 A1 | 12/2005 | Deutsch et al. | |
| 2006/0140562 A1 | 6/2006 | Joseph et al. | |
| 2006/0206997 A1 | 9/2006 | Chiang et al. | |
| 2011/0291995 A1 | 12/2011 | Shr et al. | |
| 2012/0321509 A1 | 12/2012 | Bak | |
| 2013/0035629 A1 | 2/2013 | Soltz et al. | |
| 2013/0115131 A1 | 5/2013 | Hegg et al. | |
| 2013/0267888 A1 | 10/2013 | Rhodes et al. | |
| 2013/0303996 A1* | 11/2013 | Rasooly .................. | A61L 2/10 604/264 |
| 2015/0043875 A1 | 2/2015 | Bookbinder et al. | |
| 2015/0126976 A1 | 5/2015 | Tang et al. | |
| 2015/0148734 A1 | 5/2015 | Fewkew et al. | |
| 2015/0231287 A1 | 8/2015 | Lin et al. | |
| 2015/0335773 A1 | 11/2015 | Bauco | |
| 2016/0001038 A1 | 1/2016 | Romo et al. | |

OTHER PUBLICATIONS

Notice of Reason for Rejection received in JP app. No. 2020-520186, dated Jan. 26, 2021 (7 pages).

* cited by examiner

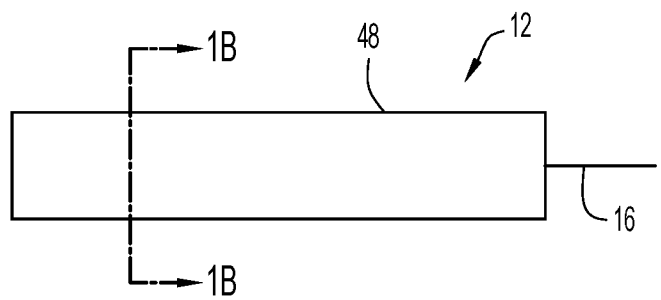
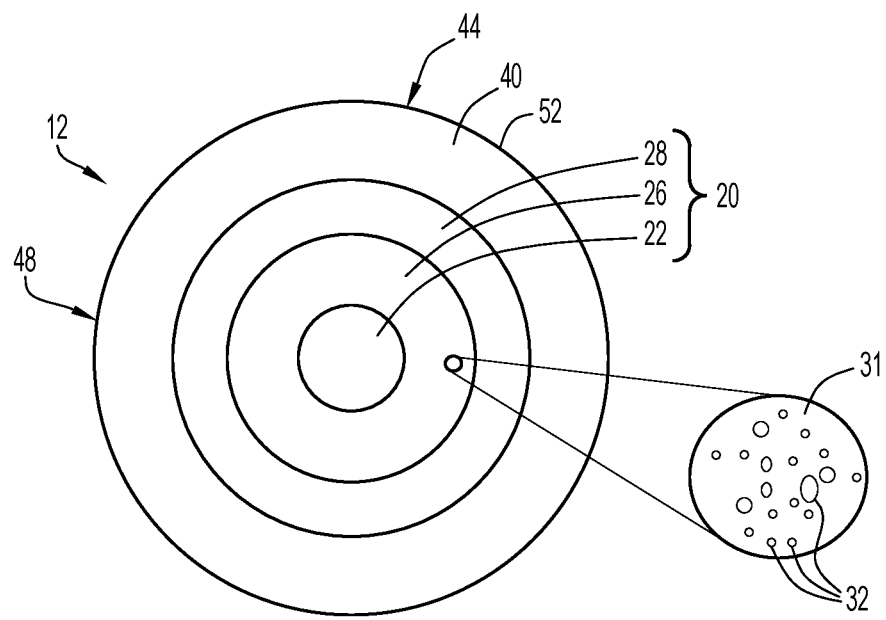
FIG.1A
FIG.1B

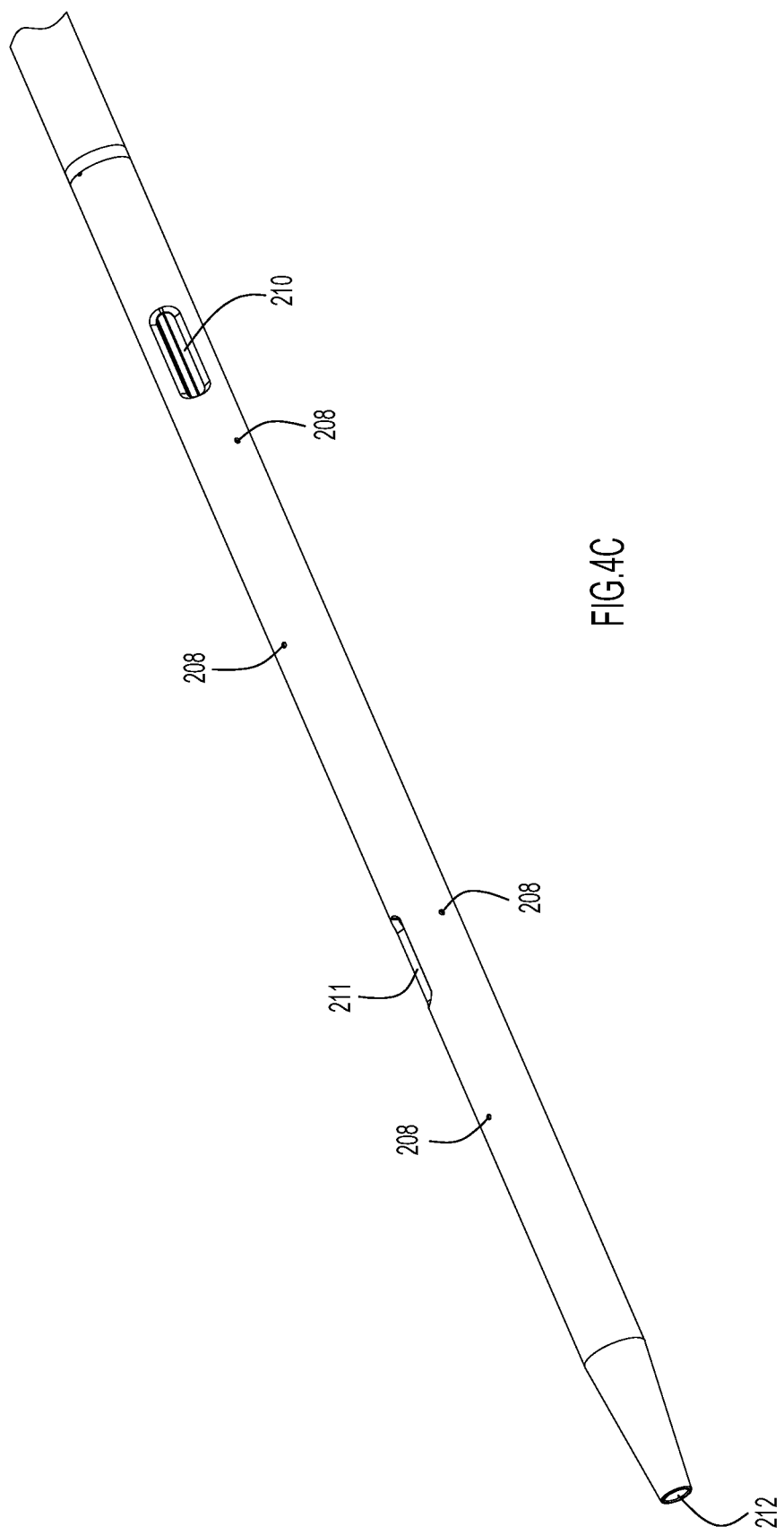

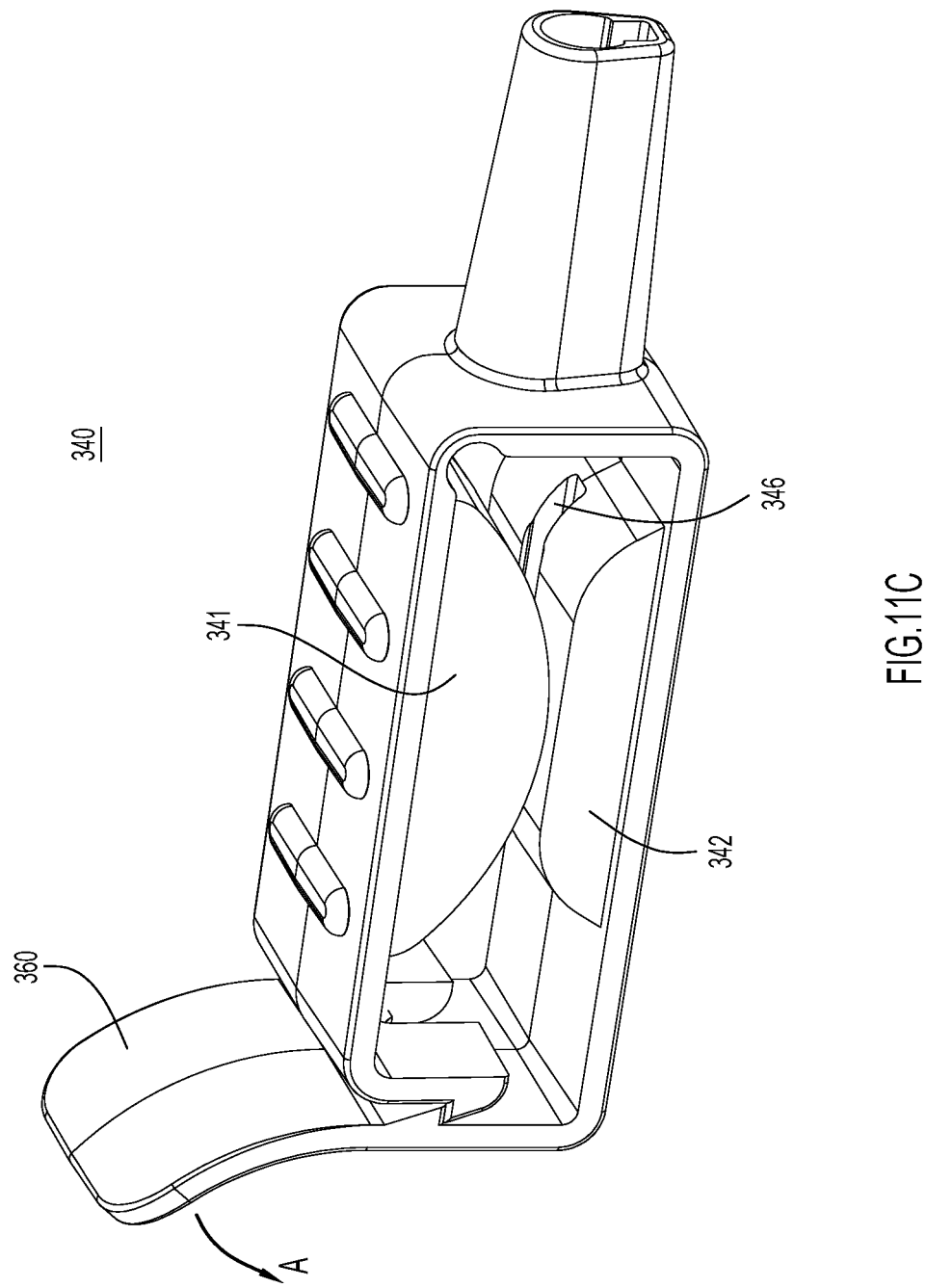

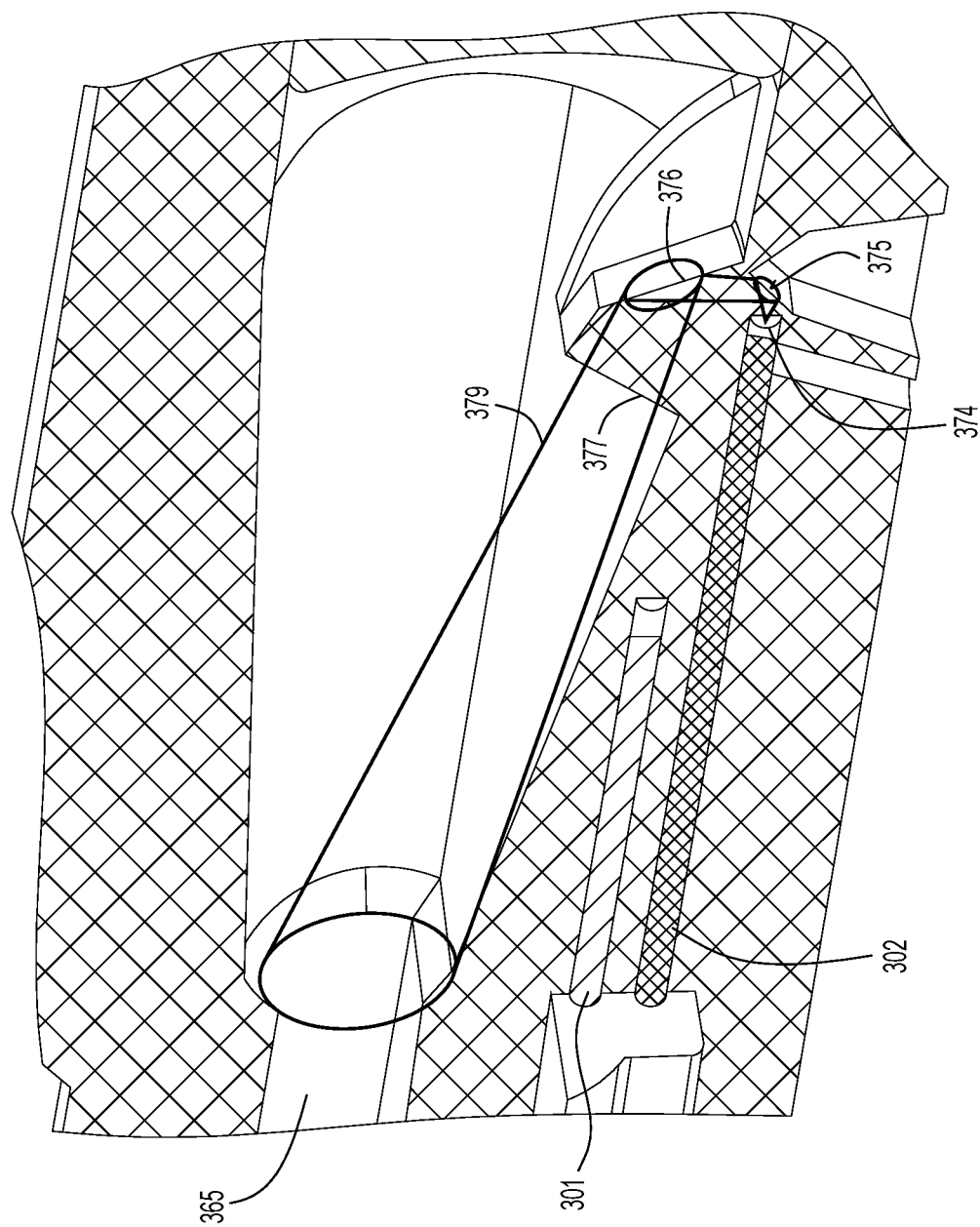

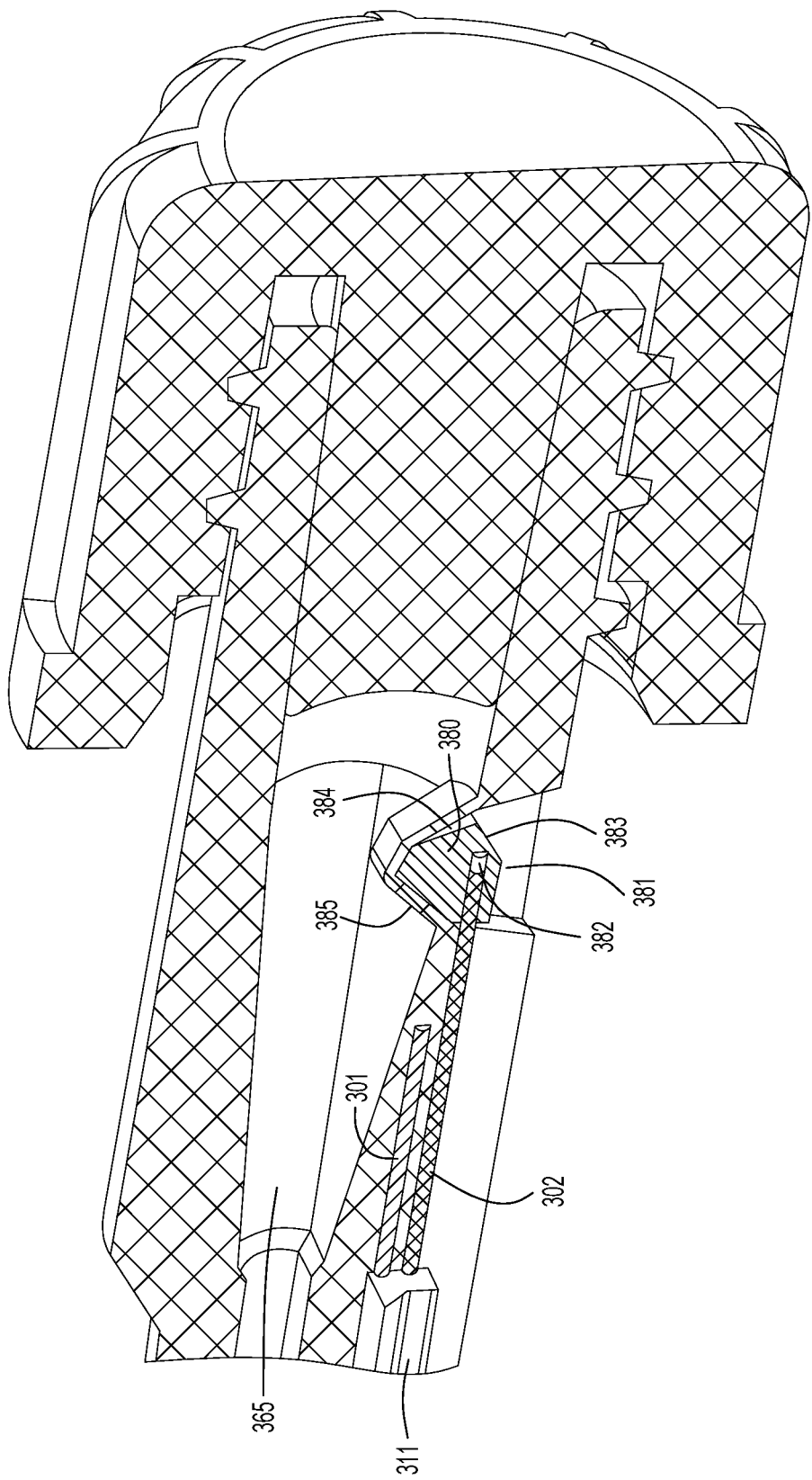

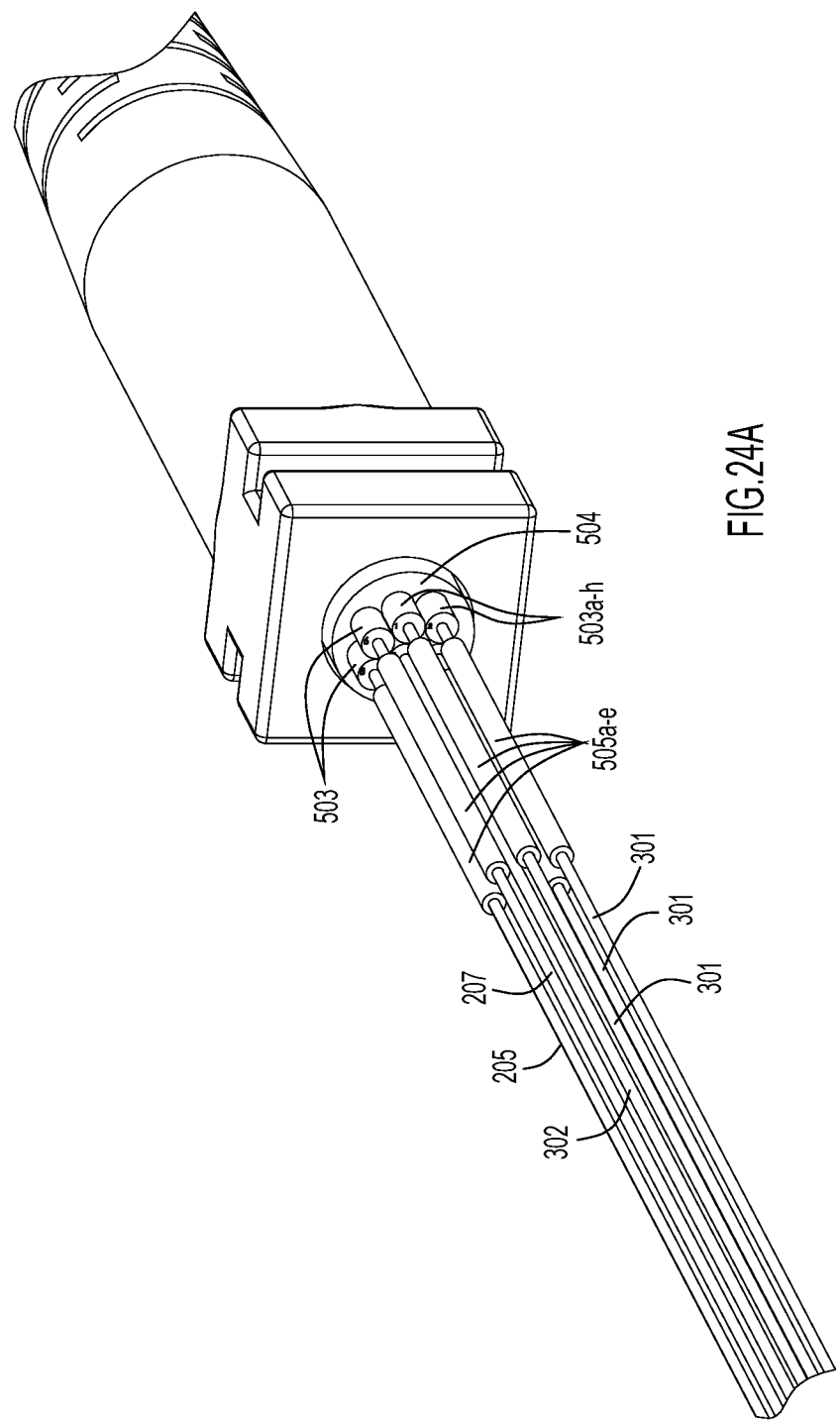

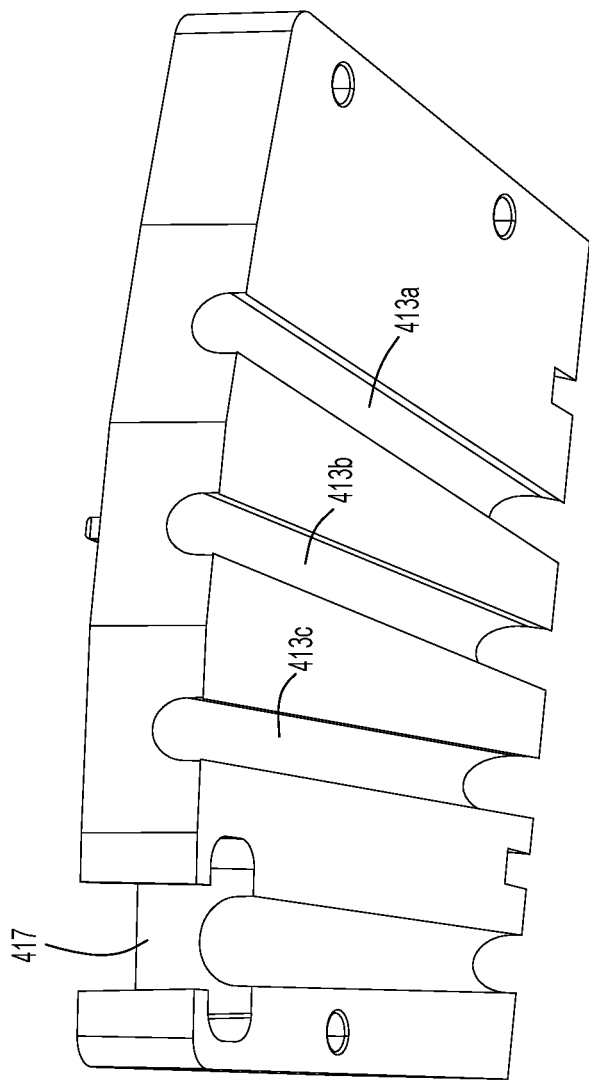

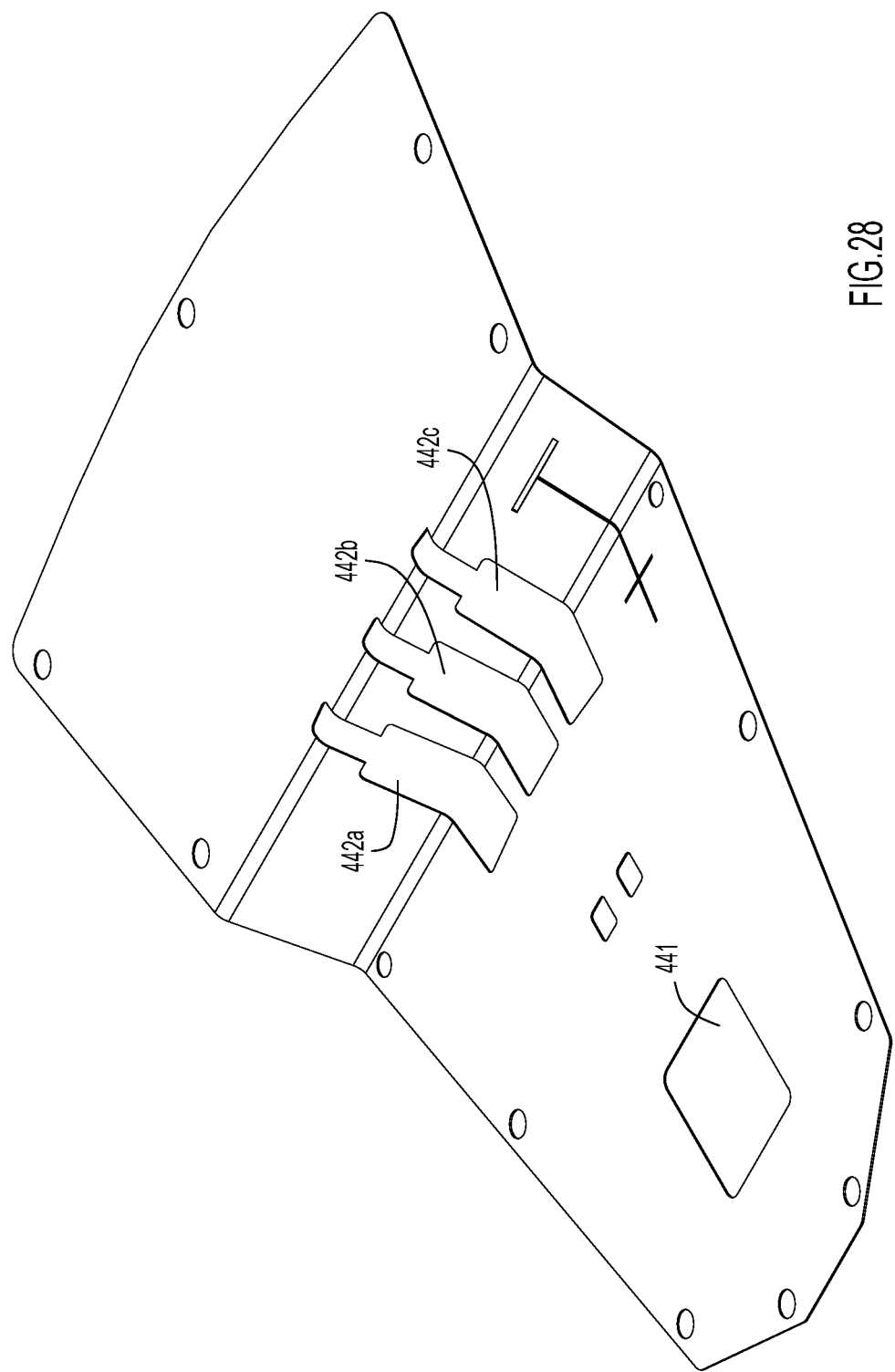

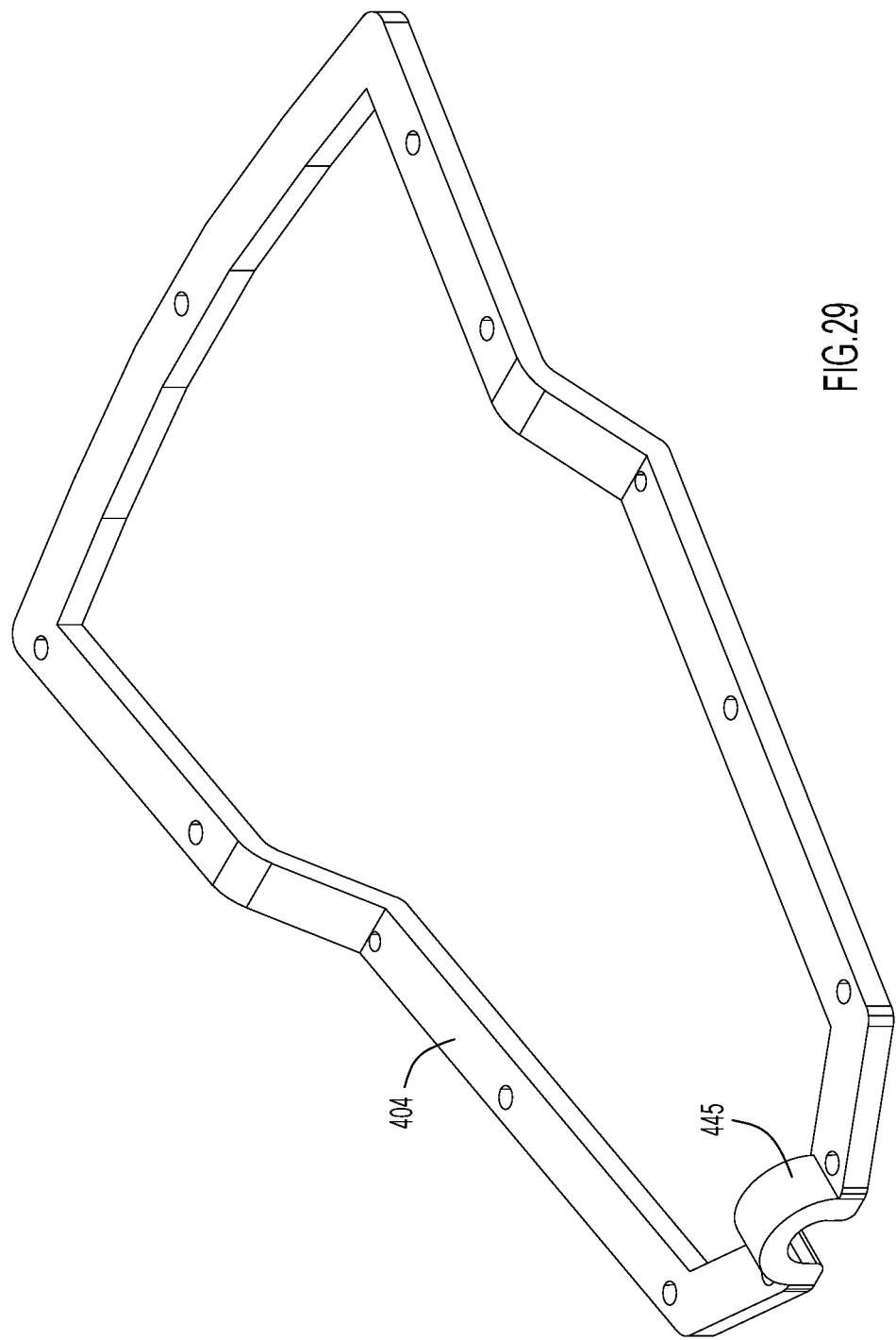

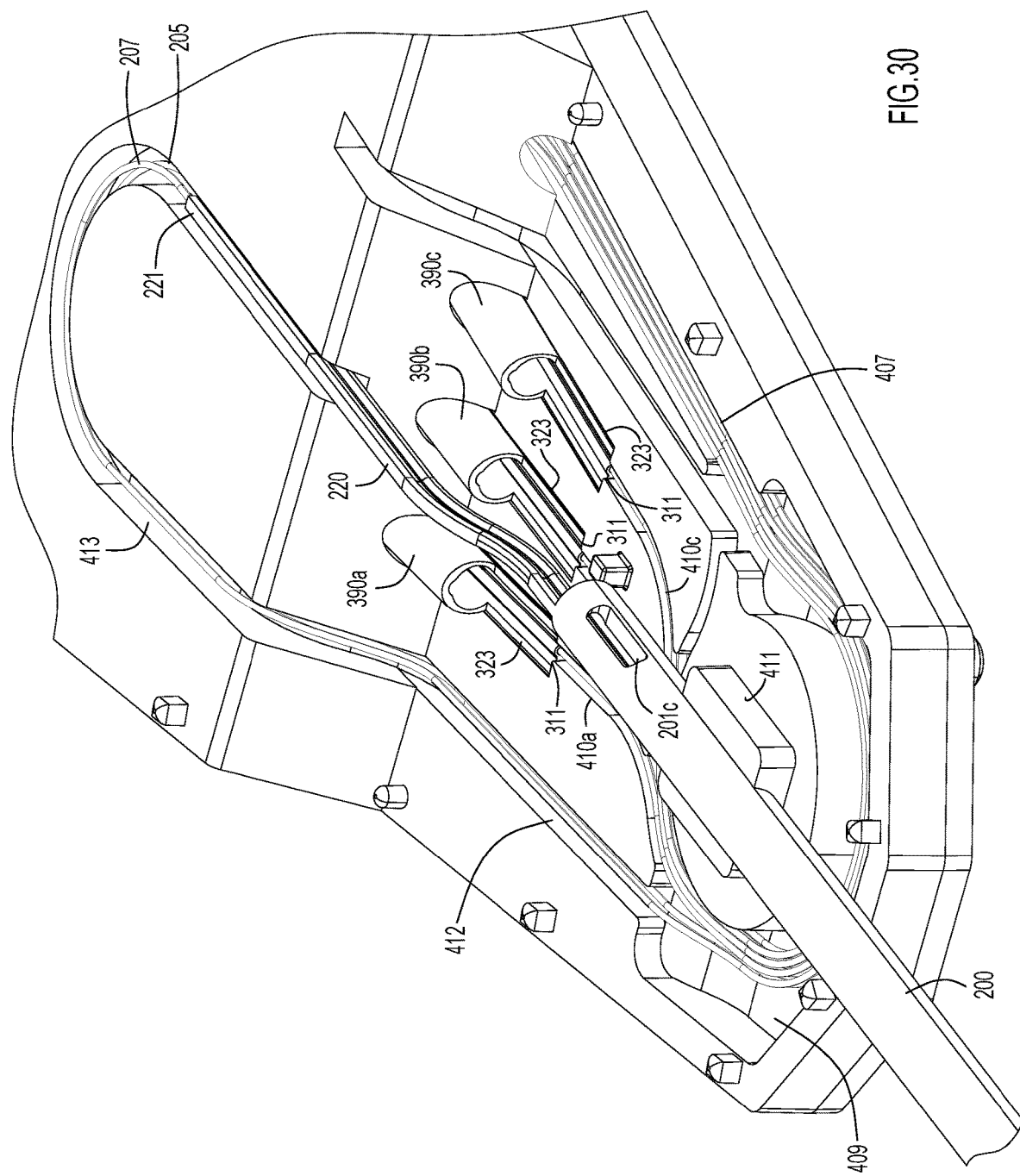

DISINFECTING METHODS AND APPARATUS

CROSS-REFERENCE TO RELATED APPLICATIONS

This application is a continuation of application Ser. No. 15/876,796, filed Jan. 22, 2018, which is a continuation-in-part of application Ser. No. 15/631,674, filed Jun. 23, 2017, now U.S. Pat. No. 9,925,287, which is a continuation of application Ser. No. 15/629,494 filed Jun. 21, 2017, now U.S. Pat. No. 9,925,285.

TECHNICAL FIELD

The present disclosure relates to devices having disinfecting capabilities and to methods for disinfecting any of a host of devices including, for example, devices used in the medical treatment of patients.

BACKGROUND

Unwanted and dangerous bacteria growth can occur on or in devices that are commonly used to treat patients. These devices may include central venous catheters, urinary catheters, ventilators, wound protection devices, etc. Hospital acquired infections account for a substantial yearly expense to hospitals and insurance companies, and are a major cause of extending hospital stays for patients. Equipment or components of water processing plants, food processing plants, dairies, livestock habitation facilities, etc. are also susceptible bacteria growth.

SUMMARY OF THE DISCLOSURE

According to some implementations disclosed herein light is used to disinfect the internal and/or external surfaces of devices used in the medical treatment of patients. The light may be any wavelength of light that is capable of killing bacteria, such as, for example, ultra violet (UV) light and blue light which may be delivered by one or both of a radially emitting optical fiber and an end emitting optical fiber.

An advantage of using light to kill bacteria is that it is not susceptible to the danger of antimicrobial resistance that can occur with the use of pharmacologic or chemical agents. Another advantage is that there are severe side effects associated with many pharmacologic or chemical agents are avoided.

According to other implementations light based detection means is used to monitor the formation of clots and/or bacterial biofilms on the outer surface of catheters residing in a vessel or duct of a patient.

It is important to note that although the forthcoming disclosure is directed primarily to medical devices, it is in no way limited to such devices. For example, the apparatus and methods disclosed herein related to killing bacteria with light and the monitoring of clot or biofilm growth can also be applied to equipment or components of water processing plants, food processing plants, dairies, livestock habitation facilities, etc.

These and other advantages and features will become evident in view of the drawings and detailed description.

BRIEF DESCRIPTION OF THE DRAWINGS

FIGS. 1A and 1B respectively show a side view and cross-section view of a radially emitting optical fiber according to some implementation;

FIG. 4C is a perspective view of a distal end portion of the main shaft depicted in FIGS. 4A and 4B.

FIG. 11C illustrates the infusion shaft running through the clamp of FIG. 11A with the clamp being in the open position.

FIG. 20B illustrates a path of the light emitted by the end emitting fiber through the proximal connector of FIG. 20A.

FIG. 21A is a cross-section side view of an infusion shaft proximal connector according to one implementation.

FIG. 24A shows a perspective view of a distal end of the umbilical cord of FIG. 23 according to one implementation.

FIGS. 27A and 27B are enlarged perspective views of the top and bottom of the mid-tray of FIG. 25, respectively.

FIG. 28 is an enlarged view of the cover of FIG. 25.

FIG. 29 is an enlarged view of the gasket of FIG. 25.

FIG. 30 is a perspective view of a partially assembled hub according to one implementation.

DETAILED DESCRIPTION

Figure 2:
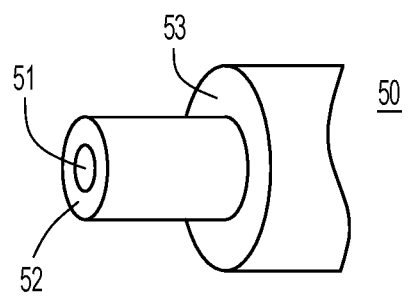
FIG. 2 is a perspective view of an end emitting optical fiber according to some implementations.

FIG. 1A is a schematic side view of a radially emitting fiber with a plurality of voids in the core of the radially emitting optical fiber 12 having a central axis 16. FIG. 1B is a schematic cross-section of a radially emitting optical fiber 12 as viewed along the direction 1B-1B in FIG. 1A. Radially emitting fiber 12 can be, for example, an optical fiber with a nano-structured fiber region having periodic or non-periodic nano-sized structures 32 (for example voids). In an example implementation, fiber 12 includes a core 20 divided into three sections or regions. These core regions are: a solid central portion 22, a nano-structured ring portion (inner annular core region) 26, and outer, solid portion 28 surrounding the inner annular core region 26. A cladding region 40 surrounds the annular core 20 and has an outer surface. The cladding 40 may have low refractive index to provide a high numerical aperture. The cladding 40 can be, for example, a low index polymer such as UV or thermally curable fluoroacrylate or silicone.

An optional coating 44 surrounds the cladding 40. Coating 44 may include a low modulus primary coating layer and a high modulus secondary coating layer. In at least some implementations, coating layer 44 comprises a polymer coating such as an acrylate-based or silicone based polymer. In at least some implementations, the coating has a constant diameter along the length of the fiber.

In other exemplary implementations, coating 44 is designed to enhance the distribution and/or the nature of radiated light that passes from core 20 through cladding 40. The outer surface of the cladding 40 or the of the outer of optional coating 44 represents the sides 48 of fiber 12 through which light traveling in the fiber is made to exit via scattering, as described herein.

A protective jacket (not shown) optionally covers the cladding 40.

In some implementations, the core region 26 of radially emitting fiber 12 comprises a glass matrix 31 with a plurality of non-periodically disposed nano-sized structures (e.g., voids) 32 situated therein, such as the example voids shown in detail in the magnified inset of FIG. 1B. In another example implementation, voids 32 may be periodically disposed, such as in a photonic crystal optical fiber, wherein the voids may have diameters between about $1 \times 10^{-6}$ m and $1 \times 10^{-5}$ m. Voids 32 may also be non-periodically or randomly disposed. In some exemplary implementations, glass 31 in region 26 is fluorine-doped silica, while in other implementations the glass may be an undoped pure silica.

The nano-sized structures 32 scatter the light away from the core 20 and toward the outer surface of the fiber. The scattered light is then diffused through the outer surface of the fiber 12 to provide the desired illumination. That is, most of the light is diffused (via scattering) through the sides of the fiber 12 and along the fiber length without the need to remove any portion of the cladding 40.

According to some implementations the nano-sized structures 32 are formed in the cladding 40 of the fiber in lieu of or in conjunction with providing nano-sized structures in the core 12.

According to some implementations the core 20 has a diameter in the range of 125-300 µm and the overall diameter of the fiber system, including the protective jacket, is in the range of 700 to 1200 µm. According to some implementation, the outer diameter of the fiber 12 without a jacket is in the range of 200-350 µm.

A detailed description of exemplary radially emitting optical fibers may be found in U.S. Reissue Pat. No. RE46,098 whose content is incorporated herein by reference in its entirety.

An example of a radially emitting optical fiber is the Fibrance® Light Diffusing Fiber manufactured by Corning® Incorporated located in Corning, N.Y. The Fibrance® Light Diffusing Fiber has many of the attributes of the radially emitting fiber 12 described above. An advantage of the Fibrance® Light Diffusing Fiber is that it emits light essentially along its entire length and has a small functional bend radius of around 5 millimeters which allows it be easily bent to assume a host of shapes. Breakage of the fiber typically occurs when it is bent to a bend radius of less than about 2 millimeters.

Radially emitting fibers like those disclosed in U.S. Reissue Pat. No. RE46,908 do not require the removal of a light reflective component or light reflective element to enable the emission of light radially from the optical fiber.

An end emitting optical fiber is an optical fiber that emits light from a terminal end of the fiber. Such emitted light is referred to herein as "end emitted light" A multimode optical fiber 50, like that shown in FIG. 2, is one example of an end emitting optical fiber wherein light is guided down the center of the fiber through the core 51 and out the end thereof. The fiber 50 includes a core 51 surrounded by a cladding 52. The cladding 52 has a lower index of refraction than the core 51 and traps the light in the core using an optical technique called "total internal reflection." The fiber 50 itself may include a coated "buffer" to protect the fiber from moisture and physical damage. The core 51 and cladding 52 are usually made of ultra-pure glass, although some fibers are all plastic or a glass core and plastic cladding. According to some implementations the core 51 has a diameter in the range of 50-250 µm and the diameter of the cladding 52 is typically around 100-500 µm. The overall diameter of the fiber system, including the buffer coating 53, is typically around 150-750 µm. Breakage of the fiber typically occurs when it is bent to a bend radius of less than about 2 millimeters.

A "transport fiber" as used herein, refers to an optical fiber that transports light longitudinally through its core to an end of the fiber with little loss. That is, the vast majority (e.g., ≥90%) of the light fed into a proximal end of the transport fiber is delivered to the terminal end of the fiber. As explained in more detail below, transport fibers are used in a variety of the implementations disclosed and contemplated herein to couple a light source (e.g., a laser) to a radially emitting optical fiber and/or end emitting fiber. According to some implementations, the transport fibers disclosed herein are multimode optical fibers.

It is important to note that a radially emitting optical fiber, like the examples discussed above, may also emit light from the core 20 at a terminal end of the radially emitting optical fiber 12. Thus, according to some implementations a disinfecting of a device may occur as a result of bacterial disinfecting light being emitted from both the circumference and the end of a radially emitting fiber. An optical fibers designated for this use is referred to herein as a "dual emitting fiber".

Blue light and ultra-violet light have been shown to kill or curtail the growth of certain types of unwanted bacteria that is hazardous and potentially fatal to mammalian life. Examples of such bacteria are *Staphylococcus aureus, Pseudomonas aeruginosa, Leuconostoc mesenteroides, Bacillus atrophaeus, Escherichia coli*, Coagulase-negative staphylococci etc. In treatments involving a mammal, blue light is preferred over ultra-violet light due to detrimental effects of ultra-violet light on mammalian cells and possible damage to host tissue. In accordance with some implementations disclosed herein blue light at a wavelength of between 380-495 nm and an exposure of between 100-1,000 Joules/cm' is employed to kill the unwanted bacteria. According to other implementations, ultra-violet light at a wavelength of 100-400 nm and exposure up to 6 $J/cm^2$ is employed to kill unwanted bacteria.

It is important to note that the present disclosure is in no way limited to the use of blue light and ultra-violet light to kill unwanted bacteria. As briefly explained above, the present disclosure contemplates the use of any type of light that is susceptible to killing unwanted bacteria.

Figure 3:
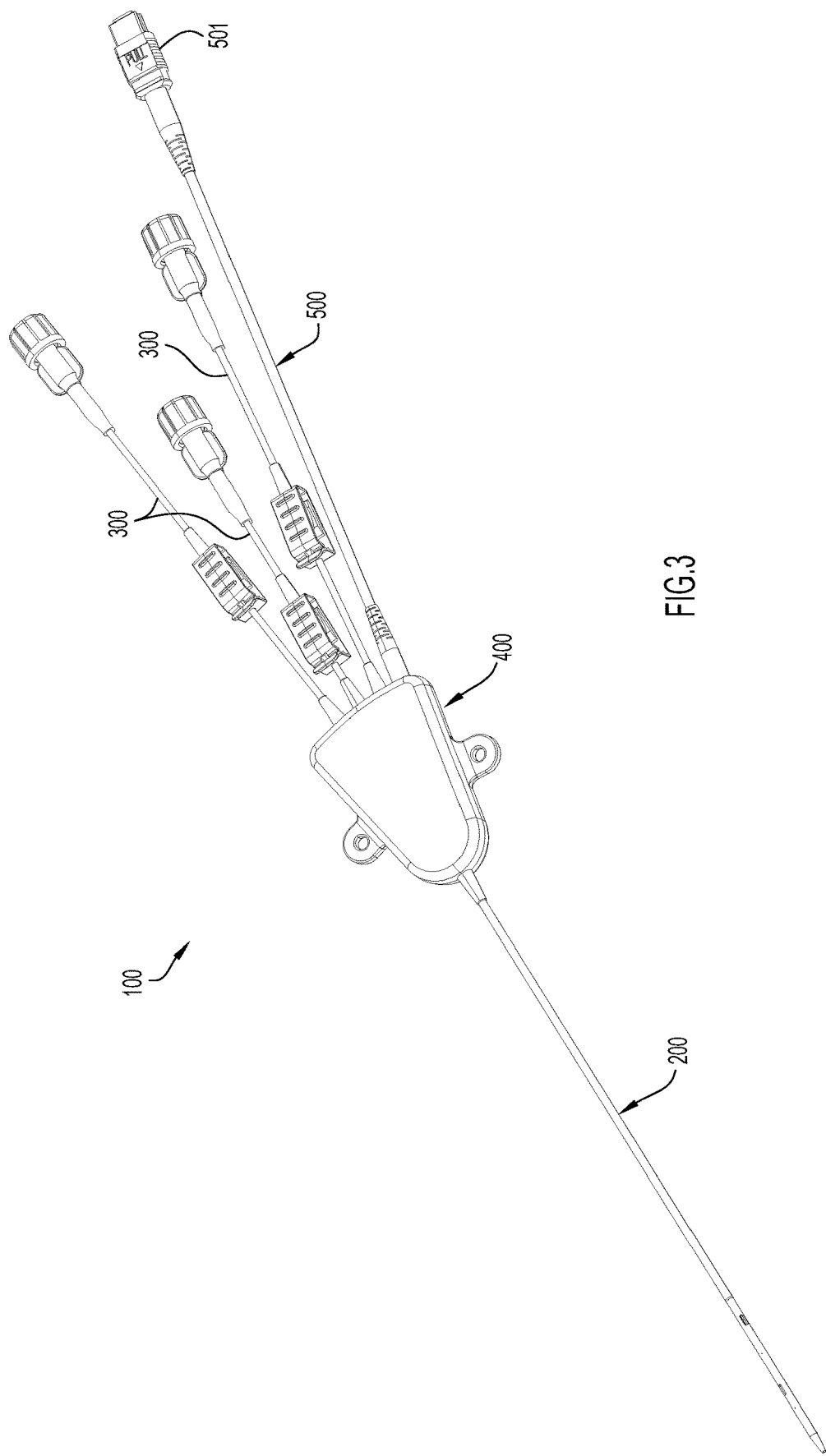
FIG. 3 is a perspective view of a central venous catheter assembly according to some implementations.

FIG. 3 illustrates a central venous catheter (CVC) 100 that will serve as an exemplary device in which light emitting optical fibers are used to disinfect one or both of the internal and external surfaces of the device. It will become evident in the forthcoming disclosure that many of the same principles employed in the CVC example are equally applicable to a host of other medical and non-medical devices.

A CVC, also called a central line, a long, thin, polymeric, flexible tube (referred to herein as the "main shaft") used to deliver medicines, fluids, nutrients, or blood products to a venous system of a patient over a long period of time, usually from days up to several weeks or more. The main shaft is often inserted into the arm or chest through the skin into a vein. The main shaft is typically threaded through this vein until it reaches a larger vein, such as, for example, a large vein near the heart.

According to some implementations one or more or all of the light emitting optical fibers that pass through the CVC are unjacketed optical fibers that include only a core and a cladding. This reduces the diametric profile of the optical fibers that allows them to be more readily integrated into a CVC, or other types of devices, without substantially altering the manner in which the CVC is traditionally used. In this way, established clinical practices may be followed. The lower diametric profile also beneficially enables the parts of the CVC to be scaled to a smaller size.

FIG. 3 depicts a perspective view of a CVC 100 according to one implementation. In this implementation the CVC includes a main shaft 200 having three working lumens (see FIGS. 4A, 5A and 5B) through which different types of therapeutic agents may be delivered to the patient. The working lumens may also serve as conduits for receiving other types of medical instruments such as, for example, a guidewire that is used to guide the distal end portion of the main shaft 200 to a desired location in the venous system.

In the example of FIG. 3, the CVC 100 includes three infusion shafts 300 having working lumens 308 that are fluidly and respectively coupled to three working lumens 201a, 201b and 201c of the main shaft 200 through a hub 400. That is, the lumen 308 of each of the infusion shafts 300 is separately fluidly coupled to one of the working lumens of the main shaft 200. The main shaft 200 of the CVC 100 may comprise more or fewer working lumens with there being a corresponding number of infusion shafts. For example, the main shaft 200 of the CVC 100 may have one, two or four working lumens with a corresponding one, two or four infusion shafts 300.

A light delivery umbilical 500 comprising one or more transport fibers may be provided to transport light from a light source to one or more optical fibers disposed in one or more of the main shaft 200, infusion shafts 300 and hub 400. The light delivery umbilical 500 may include one or more proximal connectors 501 to couple one or more light sources to the one or more transport fibers.

What follows is a detailed description of exemplary implementations of each of the main shaft 200, infusion shafts 300, hub 400, light delivery umbilical 500 and laser system.

Figure 4A:
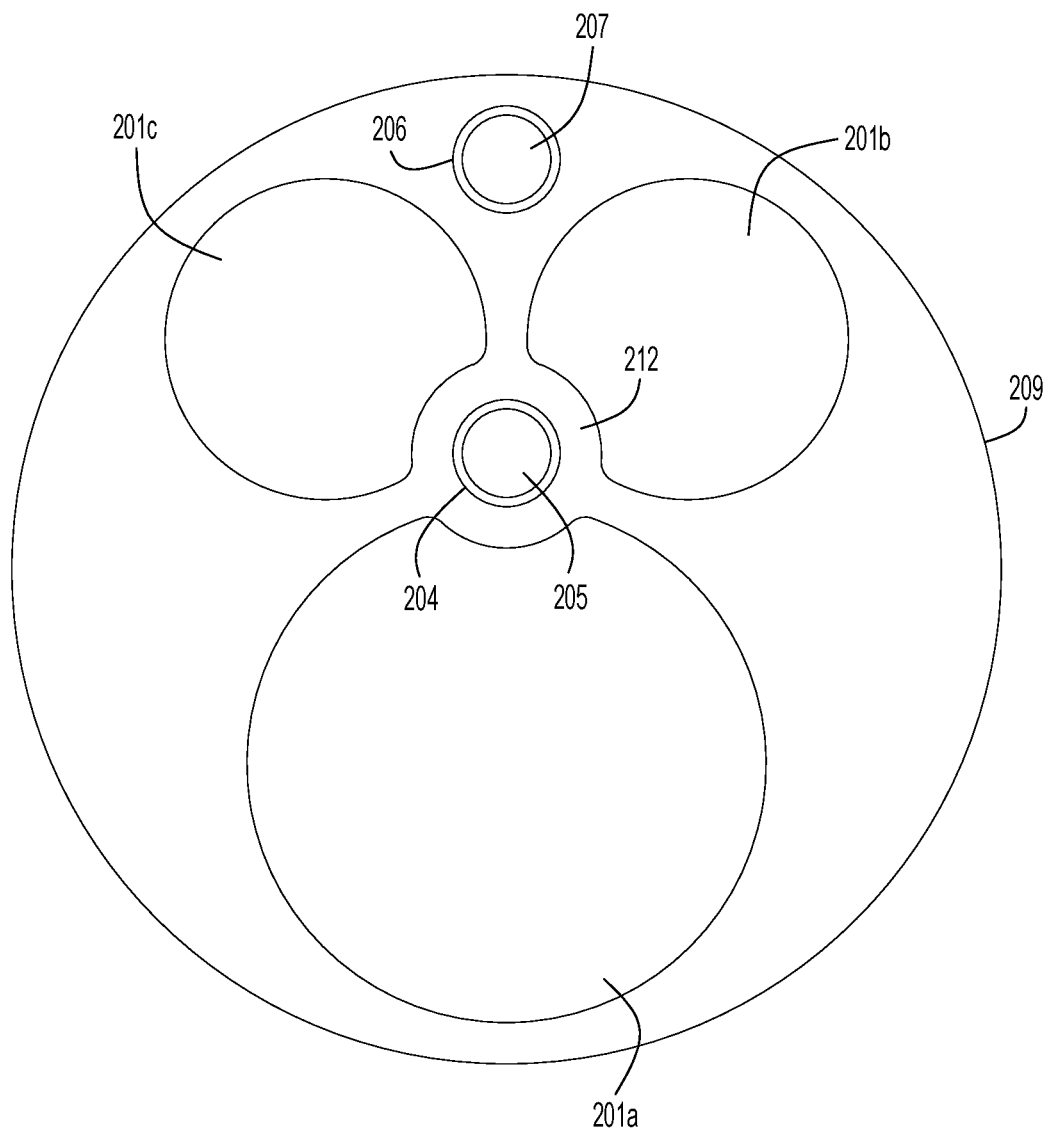
FIG. 4A is a cross-section view of a main shaft of a central venous catheter according to one implementation.
Figure 4B:
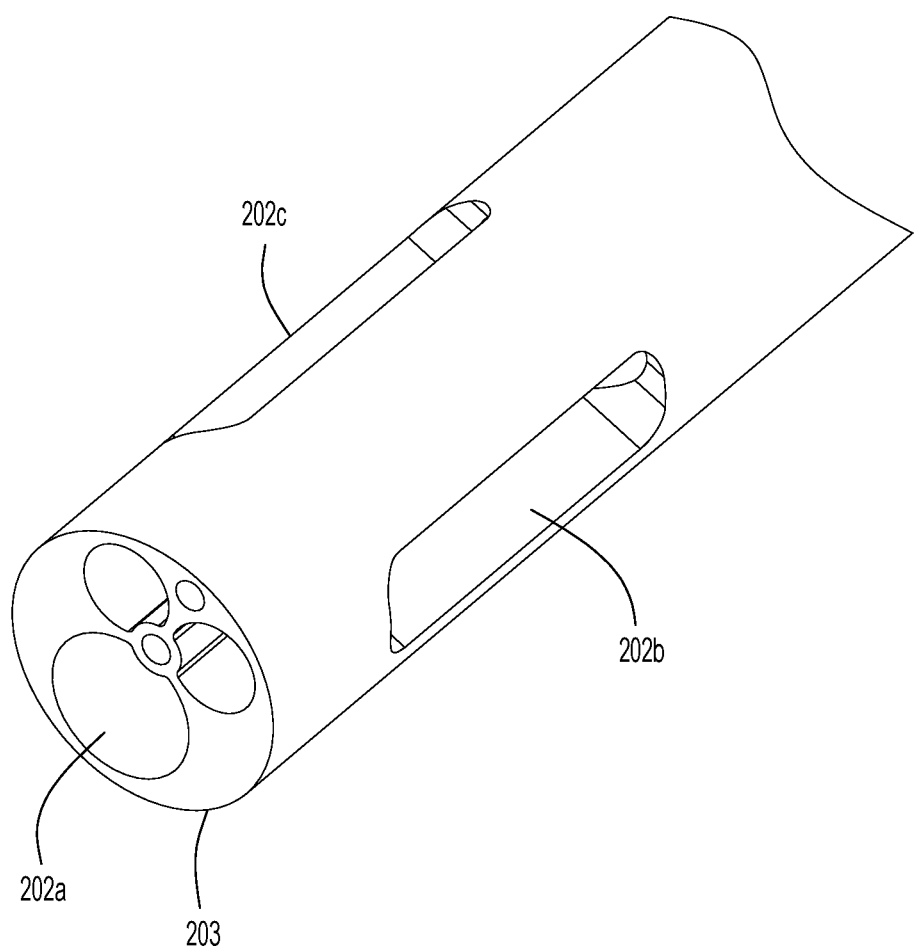
FIG. 4B is a perspective view of the main shaft depicted in FIG. 4A.
Figure 4D:
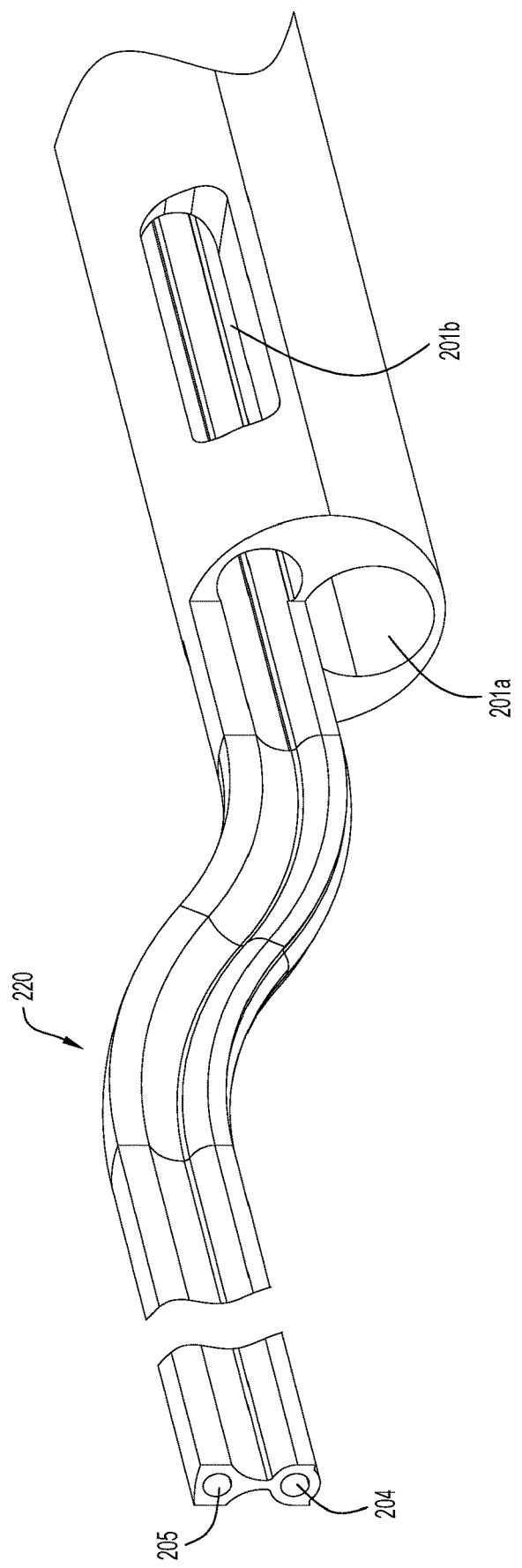
FIG. 4D is a perspective view of a proximal end portion of the main shaft according to one implementation.

FIG. 4A illustrates a cross-sectional view of a main shaft 200 of a CVC according to one implementation. As discussed above, according to some implementations the main shaft 200 includes first, second and third working lumens 201a, 201b and 201c, respectively. According to some implementations, as shown in FIG. 4B, the inlet 202a of the first working lumen 201a is located at the proximal end 203 of the main shaft 200, whereas the inlets 202b and 202c of the second and third working lumens 201b and 201c, respectively, are located a distance distal to proximal end 203 of the main shaft 200. According to other implementations one or both of the inlets 201b and 201c are located at the proximal end 203 of the main shaft 200.

In the implementation of FIG. 4A, the working lumens 201a-c have exit ports located at different longitudinal locations of the main shaft. In the example of FIG. 4C the exit ports are denoted by reference numbers 210, 211 and 212 with the distal exit port 212, intermediate exit port 211 and proximal exit port 210 being respectively associated with working lumens 201a, 201b and 201c.

According to some implementations the main shaft 200 also includes a disinfecting fiber lumen 204 wherein which resides a radially emitting fiber 205 that is capable of emitting bacterial disinfecting light. According to some implementations the disinfecting fiber lumen 204 originates at the proximal end 203 of the main shaft 200 and extends distally along at least a portion of the length of the main shaft. The radially emitting fiber 205 enters the disinfecting fiber lumen 204 at the proximal end 203 of the main shaft 200 and runs the entire length or a portion of the length of the disinfecting fiber lumen 204. Although not required, the disinfecting fiber lumen 204 is preferably placed in between the working lumens 201a-c as shown in FIG. 4A. In the implementation of FIG. 4A at least a portion of the wall 212 that forms the disinfecting fiber lumen 204 protrudes into each of the lumens 201a-c. This reduces or eliminates altogether the existence of shadows being cast into the working lumens 201a-c by virtue of the fiber lumen 204 protruding into the working lumens. The main shaft 200 is a flexible extruded polymer that is transparent or translucent to the light emitted by the radially emitting fiber 205 so that light energy that emanates radially from the radially emitting fiber 205 is able to pass throughout the working lumens 201a-c and surfaces of the main shaft to disinfect the interior of the working lumens, including the walls that form them, and the exterior surface 209 of the main shaft.

According to some implementations multiple radially emitting fibers 205 are used to disinfect the main shaft 200. In such instances the fibers may be bundled together inside a common disinfecting fiber lumen or may reside in multiple disinfecting fiber lumens dispersed within the main shaft 200.

The main shaft 200 may optionally be provided with an imaging lumen 206 that is configured to accommodate another light emitting optical fiber 207, hereinafter referred to as the "imaging fiber". As will be discussed in detail below, these elements, in addition to radial openings 208 in the main shaft 200, form a part of a detection system that may be used to detect biofilm buildup and/or clot formation on the external surface 209 of the main shaft.

According to some implementations of the CVC the main shaft 200 has neither a radially emitting fiber nor an imaging fiber.

According to some implementations the main shaft 200 comprises an elongate proximal end portion 220 that contains the disinfecting fiber lumen 204 and/or imaging lumen 205. As will be discussed in more detail below, the elongate proximal end portion 220 facilitates a routing of the radially emitting fiber 205 and/or imaging fiber 207 into the main shaft 200 via the hub 400. As will be discussed in more detail below, the hub 400 of the CVC is typically encapsulated by a casting material. The end portion 220 serves to prevent the optical fibers from being cast inside the casting material so that the optical fibers maintain a freedom of movement within the hub.

Figure 5A:
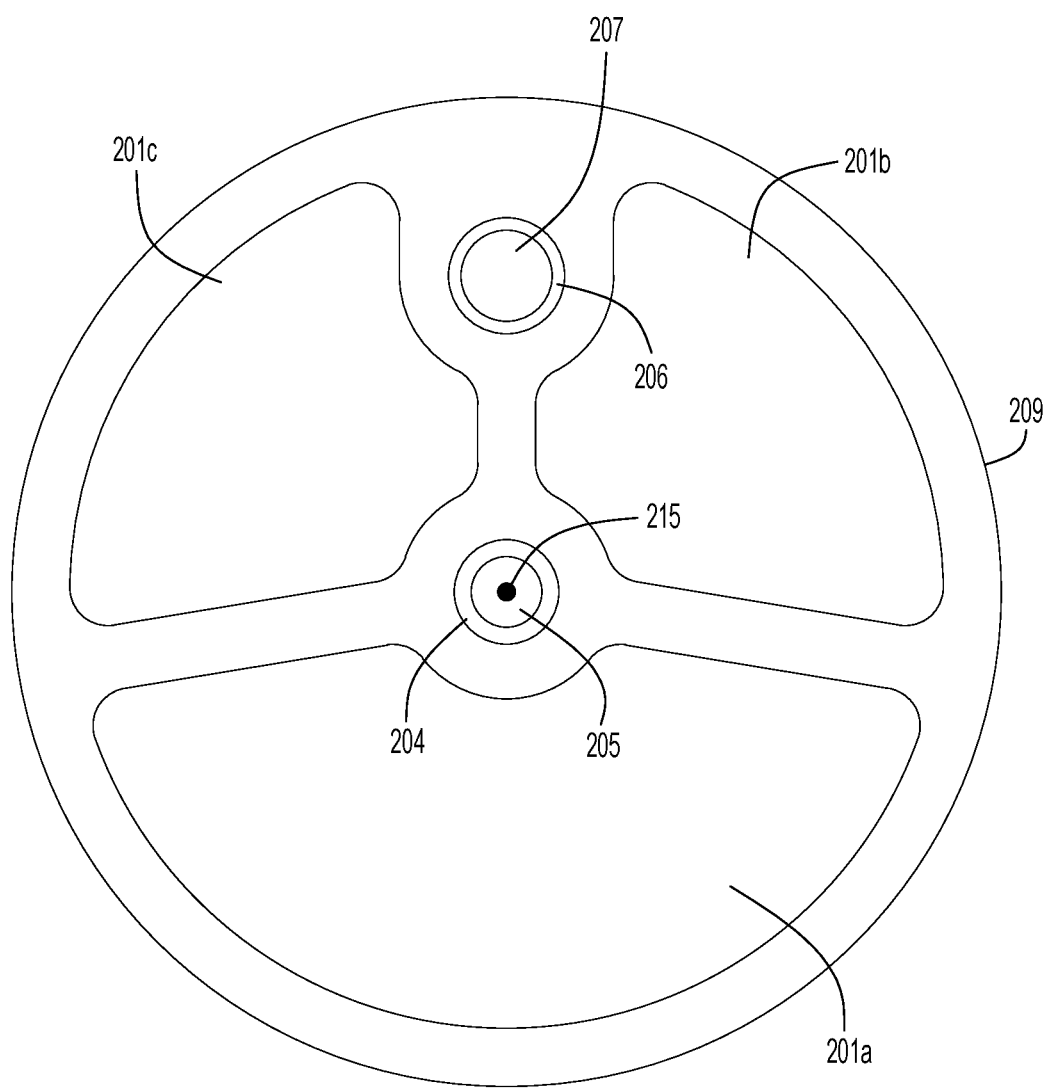
FIGS. 5A and 5B show cross-section views of a main shaft of a central venous catheter according to other implementations.
Figure 5B:
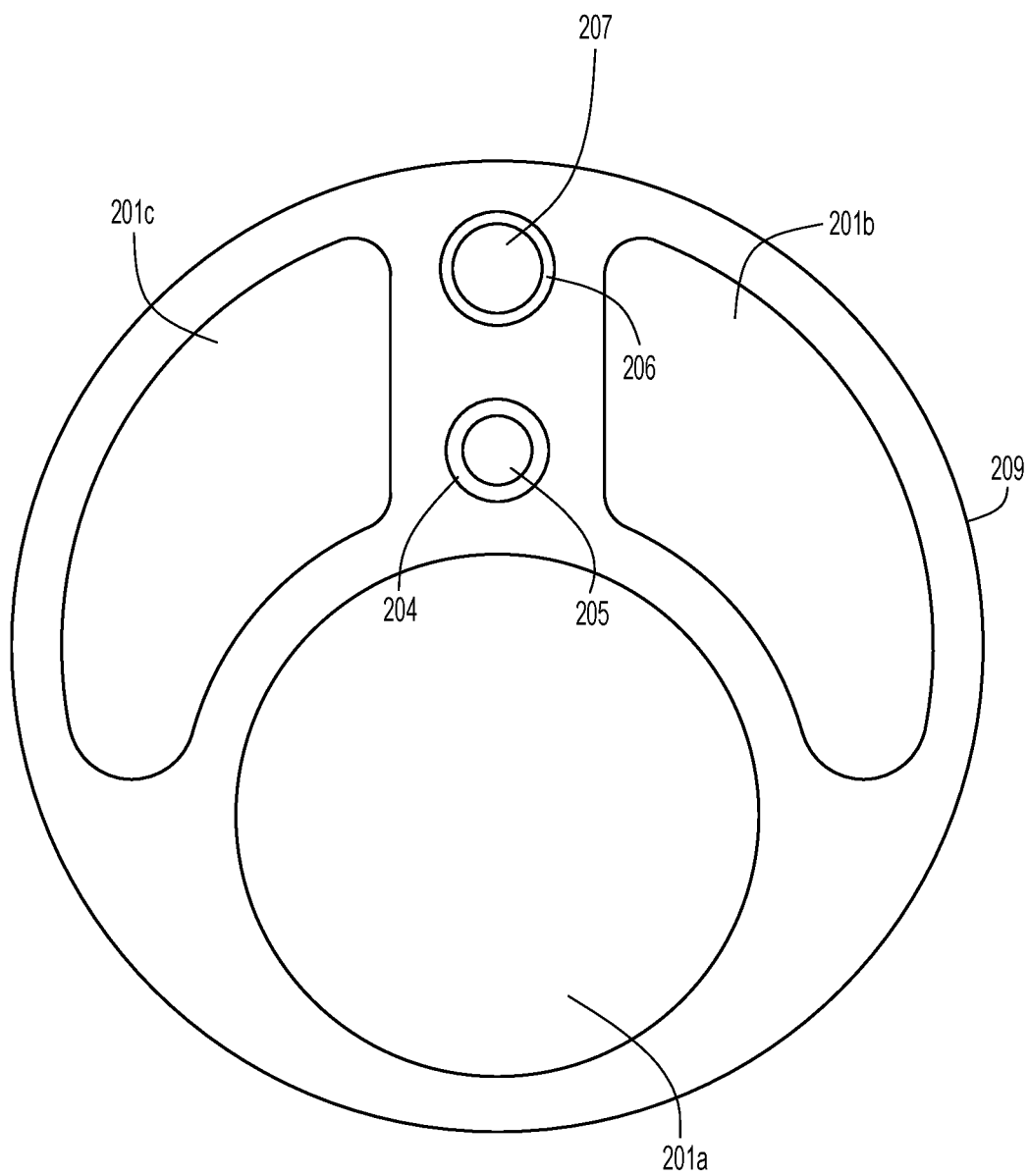

FIGS. 5A and 5B illustrate cross-sectional views of a main shaft 200 according to other implementations. In the implementation of FIG. 5A the disinfecting fiber lumen 204 is centrally located sharing a central axis 215 with main shaft 200 while in the implementation of FIG. 5B the disinfecting lumen 204 is located apart from the central axis 215 of the main shaft and runs axially parallel with the central axis along at least a portion of the length of the main shaft.

Because the imaging fiber 207 must optically communicate through the radial openings 208 located about the circumference of the main shaft 200, the imaging lumen 206 is located nearer to the exterior surface 209 of the main shaft than to the central axis 215 of the main shaft as shown in each of FIGS. 4A, 5A and 5B. As stated above, a detailed description of the configuration and function of these elements is provided below.

As explained above, optical fibers typically comprise cylindrical glass or plastic cores through which light is transported. The core runs along the fiber's length and is surrounded by a medium with a lower index of refraction, typically a cladding of a different glass, or plastic. The core and cladding of an optical fiber are susceptible to breaking if excessively stressed. To address this issue, according to some implementations the disinfecting fiber lumen 204 diameter is sized to be larger than the outer diameter of the radially emitting optical fiber 205 so that the optical fiber 205 is capable of sliding inside the disinfecting fiber lumen when the main shaft 200 is bent. This reduces or eliminates altogether the occurrence of tensile stresses in the optical fiber 205 To this end, according to some implementations the disinfecting fiber lumen 204 has diameter that is up to 30% greater than the outer diameter of the radially emitting fiber 205.

According to some implementations the main shaft 200 is formed via an extrusion process. In such implementations the radially emitting fiber 205 may be co-extruded with the shaft so that at the end of the extrusion process the fiber 205 resides in the disinfecting fiber lumen 204. According to a first co-extrusion process the disinfecting fiber lumen 204 is formed to have an inner diameter that is greater than the outer diameter of the radially emitting fiber 205. This allows the fiber 205 to slide inside the disinfecting fiber lumen 204 as described above. This has an impact of reducing tensile and bending stresses produced within the radially emitting fiber 205 when the main shaft 200 is bent in comparison to stresses that would exist if the fiber 205 were longitudinally fixed in the disinfecting fiber lumen 204.

Notwithstanding the foregoing, according to a second co-extrusion process the disinfecting fiber lumen 204 is formed to have an inner diameter that is equal to the outer diameter of the radially emitting fiber 205 with the fiber being fixed in the disinfecting fiber lumen.

In use, the CVC is periodically manipulated by a clinician. This manipulation can result in a bending and/or elongation of the main shaft and infusion shaft. In instances when the main shaft and/or infusion shaft contain an optical fiber, this bending and/or elongation of the shaft will induce bending and tensile stresses in the optical fiber. According to some implementations the main shaft 200 is constructed to limit or prevent its bending beyond a minimum bending radius of the radially emitting fiber 205. (Features for controlling tensile stresses in the optical fiber are discussed below.) The minimum bending radius may be that established by a manufacturer of the fiber 205. The minimum bending radius may be associated with a function limit or a breaking limit of the optical fiber. A functional minimum bending radius may be specified by the manufacturer of the optical fiber to denote a bending radius of the optical fiber beyond which the optical fiber is unable to properly function. A breakage minimum bending radius may be specified by the manufacturer of the optical fiber to denote a bending radius beyond which a breaking of the core and/or cladding occurs. Alternatively, the functional minimum bending radius may simply be considered to be an actual bending radius of the radially emitting fiber 205 beyond which the optical fiber is unable to properly function and the breakage minimum bending radius may be considered the actual bending radius of the radially emitting fiber 205 beyond which a breaking of the core and/or cladding occurs. The term "minimum bending radius" as used herein refers to any one of the aforestated definitions. To achieve a desired minimum bending radius of the main shaft 200 the material used to construct the main shaft may be selected to have a durometer that impedes a bending of the shaft beyond the minimum bending radius. In conjunction with or independent from the material selection, the thickness and geometry of the various walls of the main shaft 200 may be selected to achieve, or assist in achieving, the desired minimum bending radius. Stiffeners (e.g. a coil, mandrel, braiding, etc.) may also be embedded in the main shaft or otherwise attached to the main shaft to achieve the same objective.

According to some implementations the main shaft 200 is: 1) constructed so that the radially emitting fiber 205 is able to slide within the disinfecting lumen 204, and 2) constructed to limit or prevent the main shafts from bending beyond a minimum bending radius of the radially emitting fiber 205.

As discussed above, according to some implementations the radially emitting fiber 205, which includes both the core and cladding, is coextruded with the main shaft 200. According to other implementations the radially emitting optical fiber 205 is constructed by coextruding a light transmitting core with the main shaft 200 with the shaft material that surrounds the core acting as the fiber cladding. According to such implementations the core abuts the material that surrounds it.

According to some implementations at least a portion of the outer surface 209 of the main shaft 200 is equipped with a reflector that is configured to reduce or impede a loss of light emitted through the main shaft by fiber 205. This occurs by the reflector reflecting light that would otherwise escape the main shaft back into the main shaft. The reflector may comprise a light reflective coating on the external surface of the main shaft, a light reflective film wrapped about at least a portion of the external surface of the main shaft (e.g. a film heat shrunk on the outer surface of the main shaft), one or more light reflective elements embedded in the walls that form the working lumens 201*a-c*, etc.

As illustrated in the figures, according to some implementations the diameter and/or cross-sectional area of the disinfecting radially emitting fiber 205 is smaller than the diameter and/or cross-section area of each of the working lumens 201*a-c* of the main shaft 200. As also shown in the figures, according to some implementations no portion of the working lumens 201*a-c* is encircled by fiber 205.

Catheters in vivo are susceptible to the hazard of blood clot and biofilm formation on the external surface of the catheter. In the case of venous catheters, the blood clot or biofilm may break free from the catheter to create an embolization downstream which can result in serious harm or even death. In the case of urinary catheters, biofilm build up leads to patient discomfort.

Figure 6:
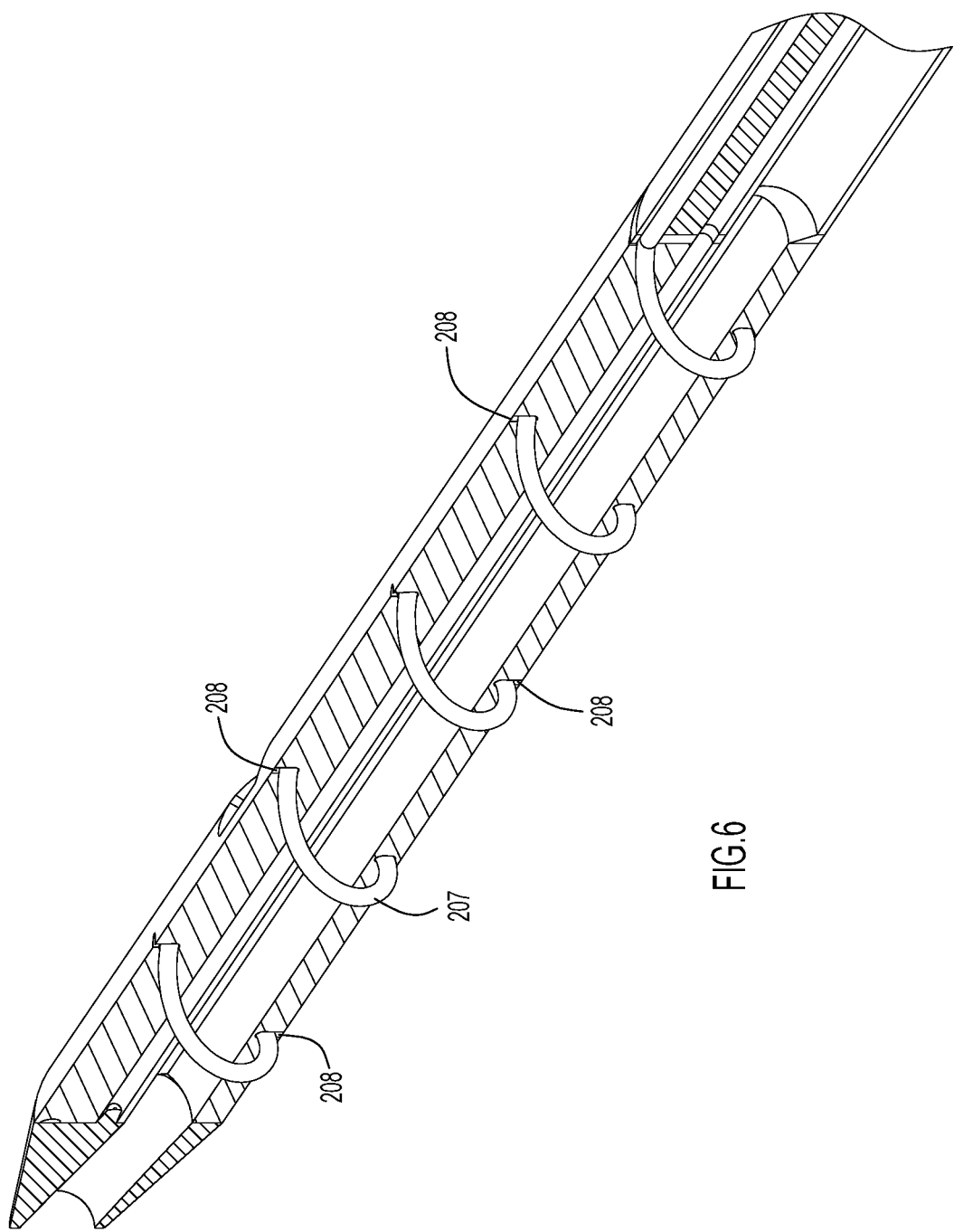
FIG. 6 shows a distal end portion of the main shaft having a spiral imaging fiber located adjacent apertures in the main shaft that extend to an exterior surface of the main shaft.
Figure 7A:
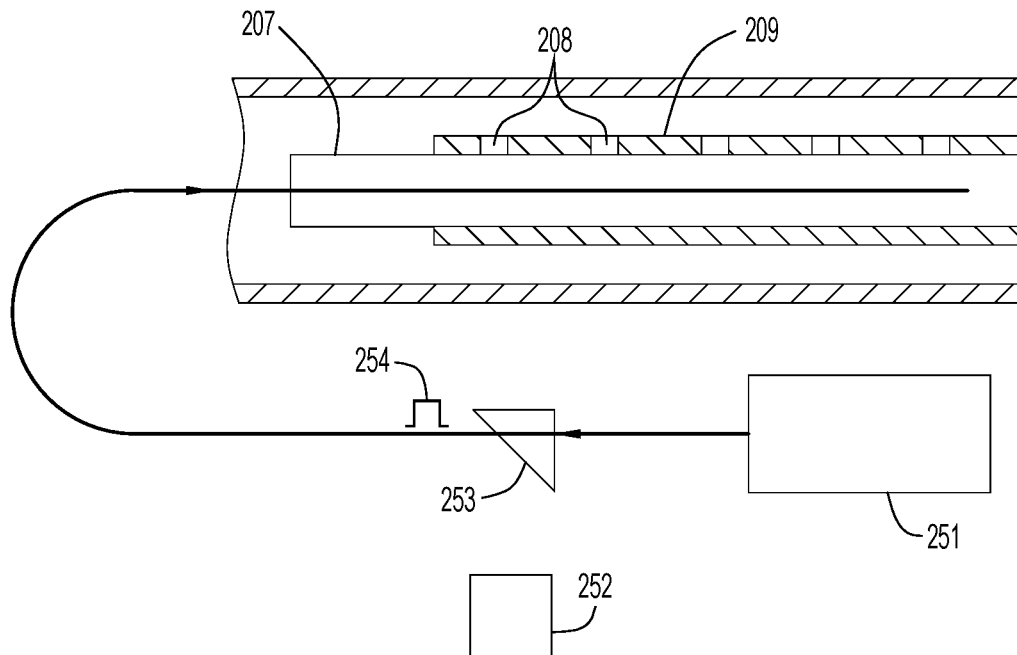
FIGS. 7A and 7B illustrate an imaging system associated with a main shaft of a central venous catheter according to one implementation.
Figure 7B:
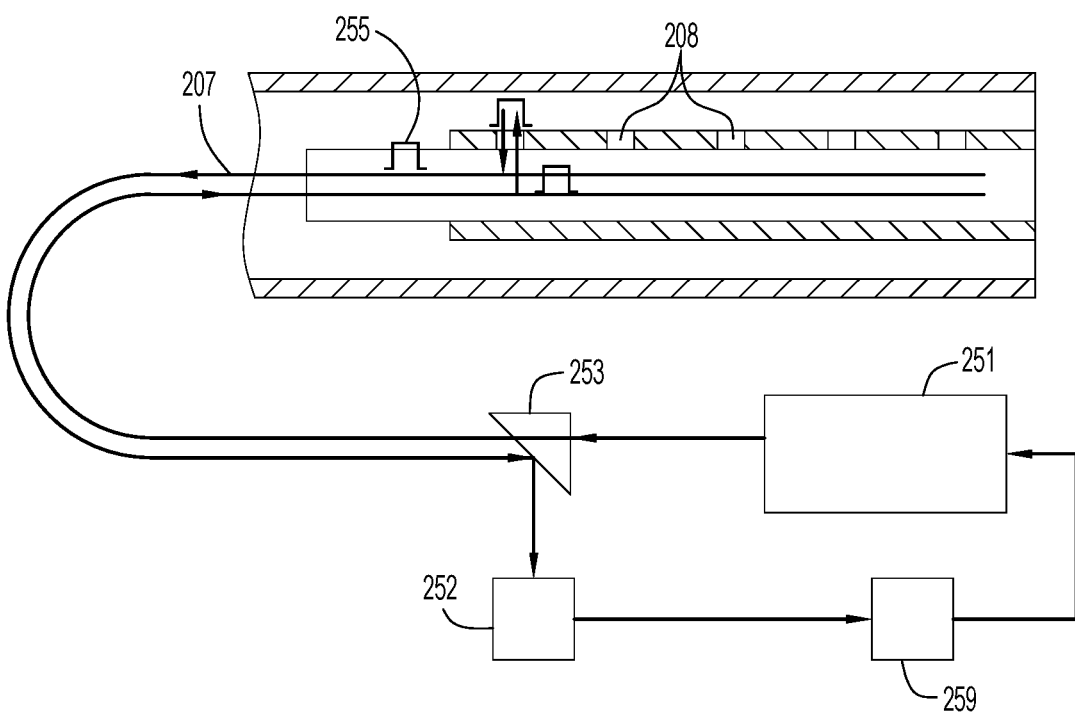

To address this issue, according to some implementations the main shaft 200 comprises an ability to detect biofilm and/or blood clot formation on the exterior surface 209 of the shaft by use of an optical based detection system like that illustrated in FIGS. 7A and 7B. The optical based detection system 250 is configured to detect short pulse width back reflections of light 255 reflected off a biofilm and/or blood clot or other unwanted substance residing on the external surface 209 of the main shaft 200. According to some implementations the detection is accomplished by radially emitting light from the imaging fiber 207 through a plurality of through holes 208 located between the imaging fiber and the exterior surface 209 of the main shaft 200. According to some implementations the portion of the imaging fiber 207 disposed in the distal section of the main shaft is located near the exterior surface 209 of the main shaft in a spiral fashion as shown in FIG. 6. According to such an implementation the through holes 208 are also spirally dispersed intermittently about the distal section of the main shaft 200, as also shown in FIG. 6, with each through hole 208 being longitudinally spaced from an adjacent through hole. Light delivered into the through holes 208 is reflected back into the through holes 208 and delivered to a back reflectance detector 252 as shown in FIG. 7B. The arrival time and amplitude of the light reflected back will depend on the location, density, thickness and mass of the biological tissue from which it is reflected. According to some implementations the imaging fiber 207 is fixed inside the main shaft 200.

Pulsed light 254 is delivered to the imaging fiber 207 from a light source 251 through a beam splitter 253. The light source 251 is typically a laser. The same beam splitter 253 is used to direct the back reflected light pulses 255 to the back reflectance detector 252. The pulse width of the light and the longitudinal distance between the through holes 208 in the main shaft 200 are selected such that the pulse width is shorter than the time taken by the light to travel between the through holes. As a result, pulsed back reflective light 255 can be consecutively collected through the through holes 208, beginning with the proximal-most through hole 208 and ending with the distal-most through hole 208, and delivered to the back reflectance detector 252 without colliding with one another. The back reflectance detector 252 identifies the through hole from which the back reflected light pulses originate by the order in which it receives the back reflected light pulses. The back reflectance detector 252 converts the back reflected light pulses 255 into electrical signals that are quantified into digital data that may be processed by a computer processor. According to some implementations a computer processor is provided in the back reflectance detector itself, while in other implementations the processor is located outside the back reflectance detector.

Upon the train of back reflected light pulses 255 having been received by the back reflectance detector 252, data associated with these pulses is processed by a software algorithm implemented by the processor to determine whether or not a biofilm, clot or other unwanted substance has formed on the exterior surface 209 of the main shaft 200. This can be achieved by comparing a baseline set of data representative of a clean outer exterior surface 209 of the main shaft 200 with the data collected. If the collected data differs from the baseline set of data in a particular way, the software algorithm may determine that a biofilm and/or clot exists on the outer surface of the main shaft.

According to some implementations the data is stored in a computer readable memory and the software algorithm compares the collected data collected with the stored data to determine if a biofilm or clot exists.

According to other implementations, and/or in conjunction with one or more of the processing methods described above, a software algorithm may process the collected data to form an image that can be used to determine the existence of a biofilm and/or clot on the outer surface 209 of the main shaft 200.

In accordance with any of the comparison methods disclosed above, a control unit 259 of the detection system may be configured to automatically activate the light source 251 to initiate a disinfection of the main shaft 200 upon the control unit determining or being informed of an unwanted substance existing on the outer surface of 209 of the main shaft 200.

According to some implementations the imaging fiber 207 is an optical fiber in which selected portions of the cladding have been removed at the site of the through holes 208 in the main shaft 200. Light is delivered from the fiber into and through the through holes 208 of the main shaft 200 via the holes formed in the cladding. According to other implementations the imaging fiber 207 comprises a radially emitting fiber 205 like those described above. According to such implementations the radially emitting fiber may possess an outer most layer (e.g. a jacket) having a plurality of strategically placed apertures that are circumferentially disposed about the radially emitting fiber 207. Light is delivered from the fiber 207 into and through the holes 208 in the main shaft 200 via the apertures formed in the outer most layer.

An advantage of the optical based detection systems disclosed herein is that they do not require a mechanical rotation and translation of the imaging fiber 207 to obtain three-dimensional data pertaining to the outer surface condition of the main shaft.

The introduction of fluids or treatment instruments into the working lumen or lumens of a CVC occurs via the use of one or more infusion shafts that are in fluid communication with the one or more working lumens of the main shaft. As discussed above, in the example CVC 100 of FIG. 3 there are three infusion shafts 300 that each have a working lumen 308 that is respectively in fluid communication with the first, second and third working lumens 201a, 201b, 201c of the main shaft 200. According to some implementations communication between the working lumens 308 of the infusion shafts 300 and the working lumens of the main shaft 200 occurs via conduits formed in the hub 400. A detailed description of various implementations of the hub 400 is provided below.

Figure 8A:
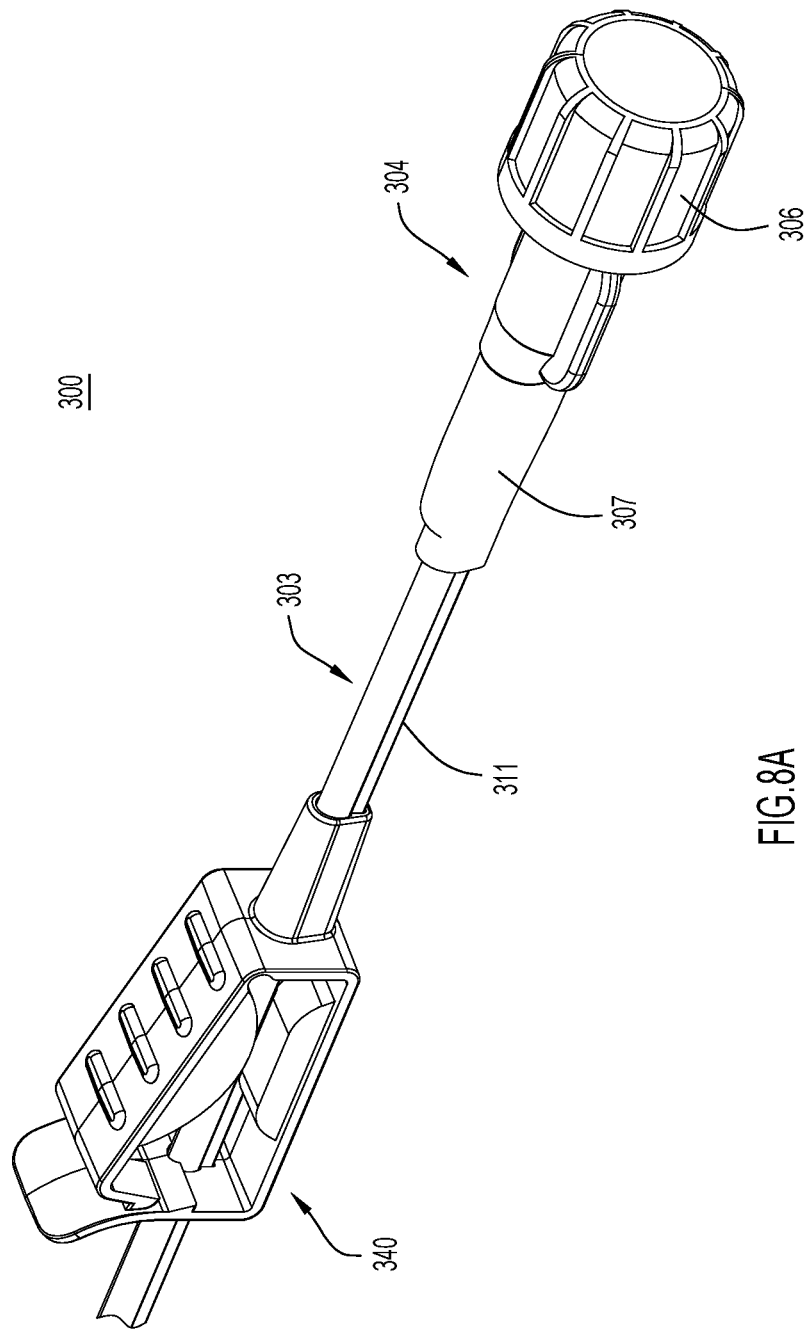
FIG. 8A is an external perspective view of an infusion shaft according to one implementation.

FIG. 8A illustrates an external perspective view of an infusion shaft 300 according to one implementation. FIG. 8A also depicts an infusion clamp 340 disposed on the infusion shaft 300 that is used to clamp down on the tubular body 303 of the infusion shaft 300 to occlude flow through the infusion shaft. A more detailed description of the infusion clamp 340 is provided below.

Figure 8B:
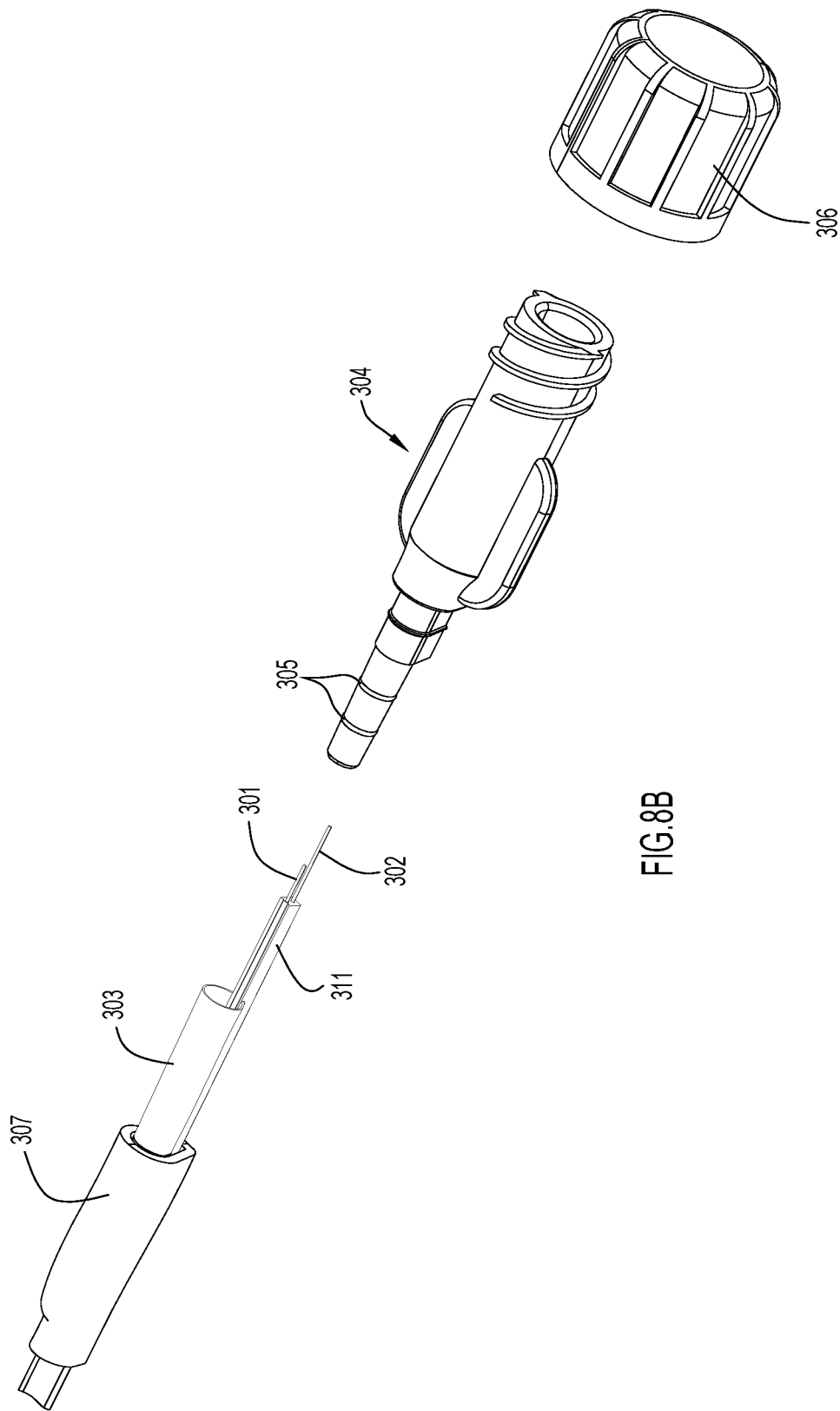
FIG. 8B is an exploded view of the infusion shaft of FIG. 8A.

FIG. 8B is an exploded view of the infusion shaft 300 of FIG. 8A (without the infusion clamp 340) that shows a partial view of a radially emitting fiber 301 and an end emitting fiber 302 that extend along at least a portion of the length of the infusion shaft. As will be discussed in more detail below, the radially emitting fiber 301 and end emitting fiber 302 are used to deliver disinfecting light, such as blue light, to the infusion shaft 300 and/or proximal connector 304.

According to some implementations the infusion shaft 300 possesses only one of a radially emitting fiber 301 and an end emitting fiber 302. According to other implementations the infusion shaft possesses neither a radially emitting fiber nor an end emitting fiber.

In the example of FIGS. 8A and 8B the infusion shaft 300 includes the tubular body 303 that is connected at its proximal end to a connector 304. According to some implementations radially extending barbs 305 are provided on the distal end portion of the connector 304 to facilitate an attachment of the tubular body 303 to the connector 304. A removable cap 306 is connected to a proximal end of the connector 304 via a threaded connection. As used herein, the cap 306 is considered to be a part of the proximal connector 304. A strain relief element 307 may also be provided at the junction of the tubular body 303 and the connector 304.

Figure 9A:
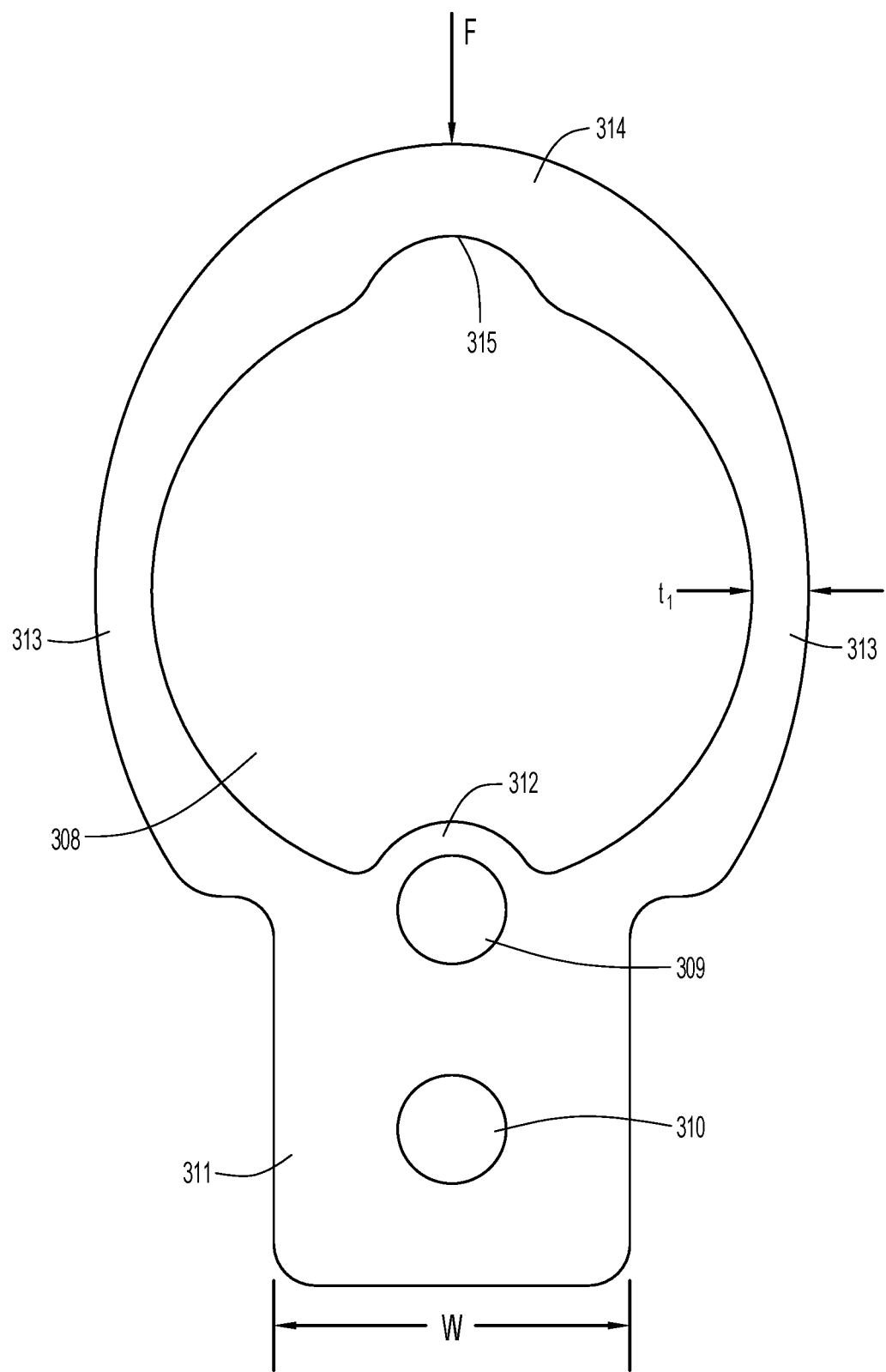
FIGS. 9A and 9B are cross-section views of a tubular body of an infusion shaft according to one implementation.

FIG. 9A is a cross-section view of the tubular body 303 according to one implementation. The tubular body 303 comprises an extruded polymeric structure having walls that define a working lumen 308, a radially emitting fiber lumen 309 configured to house the radially emitting fiber 301, and an end emitting fiber lumen 310 configured to house the end emitting fiber 302. According to some implementations the radially emitting fiber lumen 309 and end emitting fiber lumen 310 are at least partially located in a key portion 311 of the polymeric structure of the infusion shaft 300 with the radially emitting fiber lumen 309 being located adjacent the working lumen 308. According to some implementations the radially emitting fiber lumen 309 is defined by a wall segment 312 that protrudes into the working lumen 308 as shown in FIG. 9A. According to such an implementation the radially emitting fiber lumen 309 may, but not necessarily, overlap with a portion of the working lumen 308 for the purpose of maximizing the dispersion of the disinfecting light inside the working lumen when the radially emitting fiber 301 is illuminated. This maximization occurs, at least in part, as the result of no shadows being cast into the working lumen 308 by virtue of the wall segment 312 protruding into the working lumen 308 and/or an overlapping of fiber lumen 309 with the working lumen 308.

As illustrated in the figures, according to some implementations the diameter and/or cross-sectional area of each of the radially emitting fiber 301 and end emitting fiber 302 is smaller than the diameter and/or cross-section area of the working lumens 308 of the infusion shaft 300. As also shown in the figures, according to some implementations no portion of the working lumen 308 is encircled by either of fibers 301 and 302.

As explained above, the core and cladding of an optical fiber are susceptible to breaking if excessively stressed. To address this issue, according to some implementations the diameter of the radially emitting fiber lumen 309 is sized to be larger than the outer diameter of the radially emitting optical fiber 301 so that the optical fiber is capable of sliding inside the radially emitting fiber lumen 309 when the infusion shaft 300 is bent. To this end, according to some implementations the radially emitting fiber lumen 309 has diameter that is up to 30% greater than the outer diameter of the radially emitting fiber 301.

To facilitate a closing off of the working lumen 308 by use of the clamp 340, portions 313 of the sidewalls that form the working lumen have a reduced thickness t1 as compared to the remaining portions of walls that define the working lumen 308. The reduced thickness portions 313 are engineered to act as hinges that promote a collapsing of the tubular body 303 on itself when the clamp 340 is caused to exert a force F against a compression wall 314 that is located opposite the key portion 311. According to some implementations the compression wall 314 includes a recess 315 that is configured to mate with the protruding wall segment 312. The mating of the parts 312 and 315 promotes an ordered closure of the working lumen 308 in a manner that assists in inhibiting a twisting of the tubular body 303 when the clamp 340 acts to close the working lumen.

The key portion 311 of the infusion shaft 300 serves a number of functions. It provides a region that is located outside, or substantially outside, the working lumen 308 for housing the radially and end emitting fibers 301, 302. This is important because if the fibers 301, 302 were to be located outside the key portion 311, they would be susceptible to breakage when the tubular body 303 is clamped to effectuate a closing of the working lumen 308. A further advantage of housing the fibers 301, 302 in the key portion 311 of the tubular body 303 is that accessibility to and through the working lumen 308 of the infusion shaft 300 remains the same or similar to that of conventional CVC systems.

As will be described in more detail below, the key portion 311 can also be configured to reside within a groove 346 of a lower pad 342 of the clamp 340 in order to maintain the tubular body 303 properly oriented in the clamp to ensure the upper pad 341 of the clamp properly acts on the compression wall 314 during the clamping procedure. This prevents or inhibits a twisting of the tubular body 303 during the clamping procedure that could otherwise result in a breaking of the fibers 301, 302.

As explained above, stresses produced within an optical fiber (e.g., a radially emitting optical fiber and/or an end emitting optical fiber) can be caused by a bending of the fiber. For this reason, according to some implementations the infusion shaft 300 is constructed to limit or prevent its bending beyond a minimum bending radius of one or both of the radially emitting fiber 301 and end emitting fiber 302.

As discussed above in conjunction with the description of the main shaft 200, optical fibers typically have a functional minimum bending radius beyond which the fibers are unable to properly function and a breakage minimal bending radius beyond which a breaking of the core and/or cladding occurs. The functional and/or breakage minimum bending radius may be specified by the manufacturer of the optical fiber. The functional and/or breakage minimum bending radius may alternatively be considered the actual bending radius of the optical fiber beyond which the optical fiber is unable to properly function or which a breaking of the core and/or cladding occurs. To achieve a desired minimum bending radius of the infusion shaft 300 the material used to construct the infusion shaft may be selected to have a durometer that impedes a bending of the shaft beyond the functional or breakage minimum bending radius of one or both of the radially emitting fiber 301 and the end emitting fiber 302. In conjunction with or independent from the material selection, the thickness and geometry of the various walls of the infusion shaft 300 may be selected to achieve, or assist in achieving, the desired function or breakage minimum bending radius. Moreover, a stiffening of the infusion shaft 300 may occur by embedding one or more stiffening elements (e.g. a coil, mandrel, braiding, etc.) inside the key portion 311 along a length of the tubular body 303. According to other implementations a stiffening jacket or other element may be attached to at least a portion of the outer surface of the tubular body to obtain a desired stiffness that resists against the fiber 301 and/or 302 bending beyond its/their minimum bending radius. Stiffeners (e.g. a coil, mandrel, braiding, etc.) may also be embedded in the main shaft or otherwise attached to the main shaft to achieve the same objective.

Because a majority of the walls of the tubular body 303 that form the working lumen 308 are engineered to be relatively flexible to accommodate a closing of the working lumen by the clamp 340, according to some implementations a majority of the stiffness attributed to the tubular body 303 is engineered to reside in the key portion 311. According to some implementations this is accomplished by the key portion 311 having an overall width dimension "w" that is greater than any of the thickness dimensions of the remainder of the walls that form the working lumen 308. The shape of the key portion 311, for example a rectangular shape, can also contribute to its stiffness.

Figure 9B:
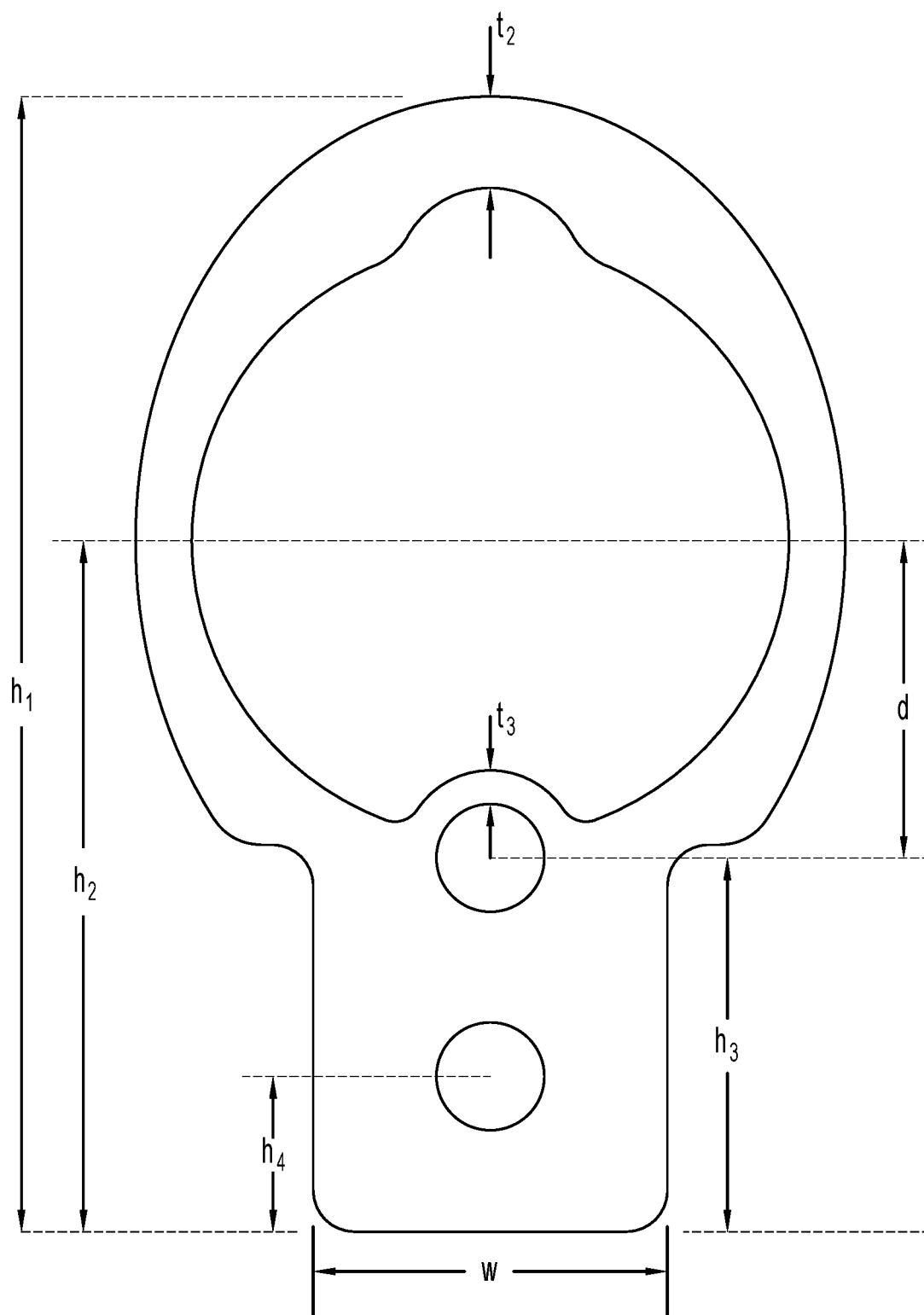

With reference to FIGS. 9A and 9B, according to one implementation the dimensions of the tubular body 303 are as follows. The overall height "h1" is 3.055 millimeters with a horizontal centerline of the working lumen 308 residing 1.850 millimeters above the bottom end of the tubular body as denoted by the reference "h2". The key portion 311 has a height "h3" and a width "w", each of which are 1.000 millimeters. The centerline of the end emitting fiber lumen 310 is located a height "h4" of 0.425 millimeters above the bottom end of the tubular body 303. Each of the walls of the tubular body that form the hinge portions 313 have a thickness "t1" of 0.125 millimeters. The wall thickness dimensions "t2" and "t3" are 0.250 millimeters and 0.100 millimeters, respectively. The distance "d" between the central axis of the radially emitting fiber lumen 309 and the horizontal centerline of the working lumen 308 is 0.850 millimeters. The diameter of each of the radially emitting fiber lumen 309 and end emitting fiber lumen 310 is about 0.280 millimeters. Furthermore, the width "w" of the key portion 311 is dimensioned to be smaller than the maximum width dimension of the working lumen 308.

According to some implementations the ratio of h3/h1 is less than 0.6. By limiting the size of the key portion 311 in this way, it limits the degree by which the infusion shaft 300 differs from traditional infusion shafts. In addition, according to some implementations the ratio of t1/t2 is less than 1.0 to yield the creation of hinge portions 313 that are configured to bend when a force is applied downward on the top end of the infusion shaft 300.

Figure 10A:
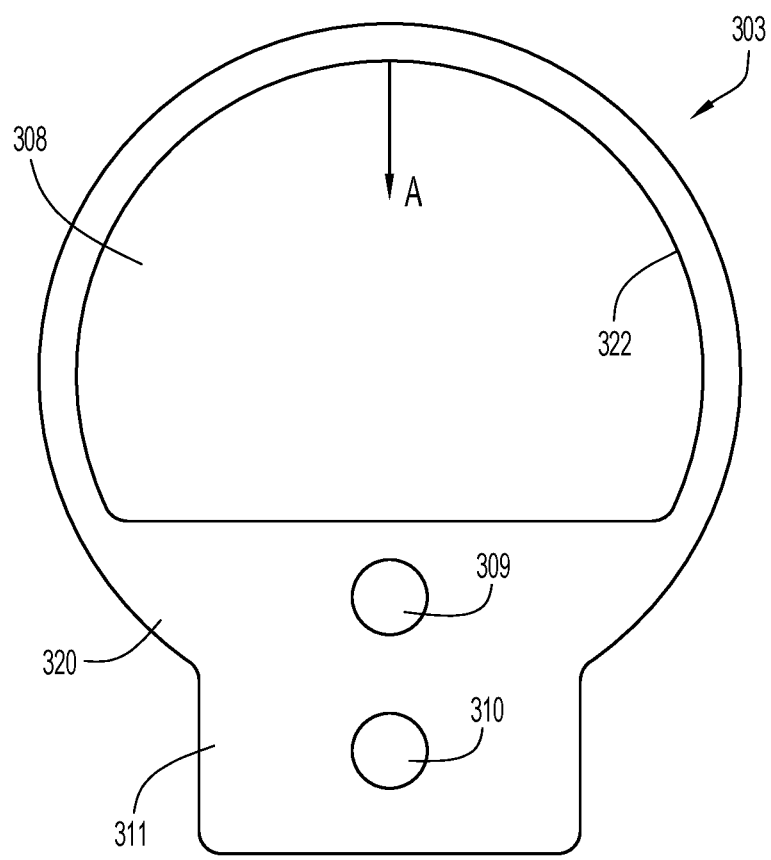
FIGS. 10A-C illustrate cross-section views of the main shaft according to other implementations.
Figure 10B:
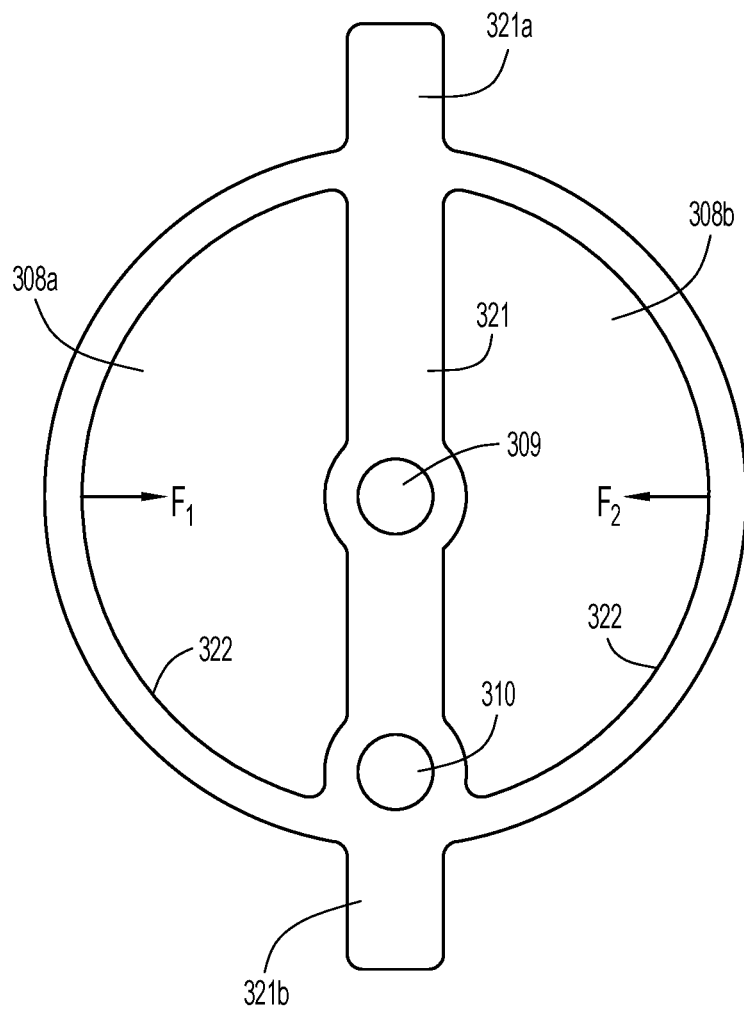
Figure 10C:
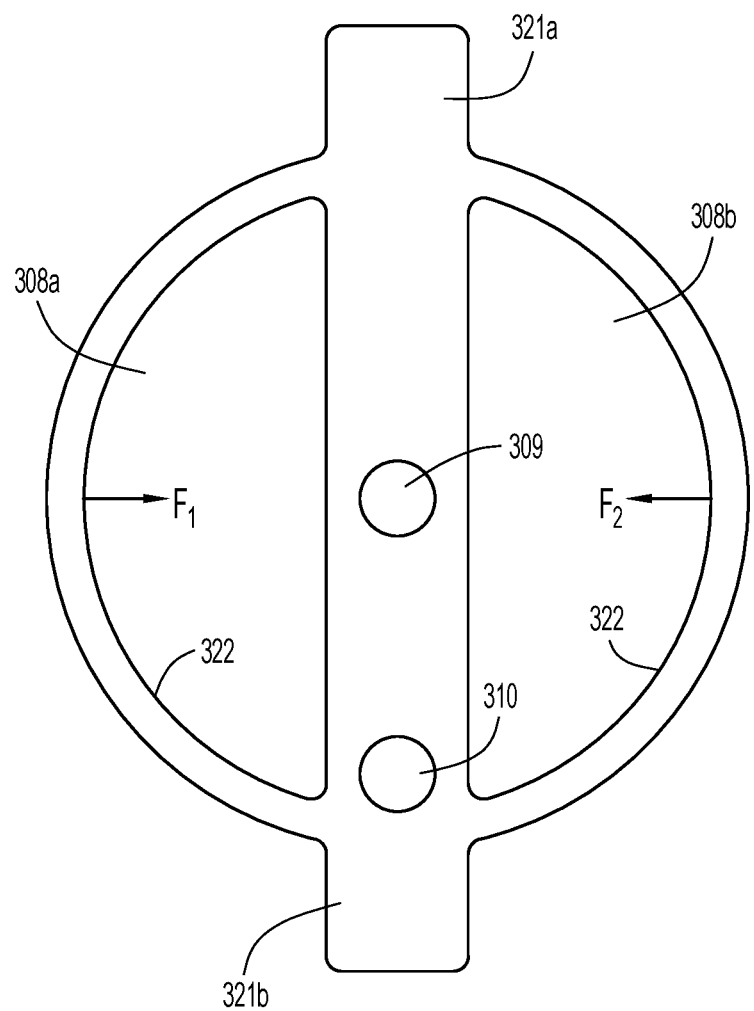

FIGS. 10A-C are cross-section views of example alternative infusion shaft tubular body designs. In the implementation of FIG. 10A the working lumen 308 of the tubular body 303 has a semi-circular configuration that is partially truncated by a structure 320 that houses the radially emitting fiber lumen 309. The structure 320 extends from the key portion 311 that houses the end emitting fiber lumen 310. Clamping the working lumen 308 shut in the direction of arrow A can occur in a manner like that described above in conjunction with the implementation of FIG. 9A.

In the implementations of FIGS. 10B and 10C each of the radially emitting fiber lumens 309 and end emitting fiber lumen 310 are suspended in the tubular body 303 by a septum/wall 321 with the radially emitting fiber lumen residing centered in the tubular body. In each of these implementations, the infusion shaft is provided with first and second lumens 308a and 308b that are separated by the septum 320. In each of these implementations the first and second working lumens 308a and 308b can be clamped shut by applying an inward force F1 and F2 to the walls of the tubular body, respectively. In each of the implementations of FIGS. 10A and 10B first and second wings 321a and 321b protrude from opposite sides of the tubular body and are used to align the tubular body 303 in a clamp (not shown) that is capable of applying the forces F1 and F2. According to some implementations the working lumen 308a is configured to transport a fluid and the working lumen 308b is configured to receive a treatment instrument, such as, for example, a guidewire.

As shown in FIG. 10B, the radial emitting fiber lumen 309 is partially formed of wall segments on each side of the fiber lumen that protrude into the respective first and second lumens 308a and 308b. Although not shown in FIG. 10B, according to some implementations the interior wall 322 of the working lumens 308a and 308b each comprise a recess that is configured to mate with the protruding wall segments of the fiber lumen. The mating of the parts promotes an ordered closure of the working lumens 308a and 308b in a manner that assists in inhibiting a twisting of the tubular body 303 when the clamp 340 acts to close the working lumens.

According to some implementations the infusion shaft 300 is a flexible extruded polymer that is transparent or translucent to the light emitted by the radially emitting fiber 301 so that light that emanates radially from the radially emitting fiber 301 is able to pass through the walls of the infusion shaft to disinfect the interior walls 322 of the working lumens 308a, 308b.

As stated above, according to some implementations the infusion shaft 300 is formed via an extrusion process. In such implementations one or both of the radially emitting fiber 301 and end emitting fiber 302 may be co-extruded with the infusion shaft so that at the end of the extrusion process fiber 301 resides in the radially emitting fiber lumen 309 and fiber 302 resides in the end emitting fiber lumen 310. According to a first co-extrusion process one or both of the radially emitting fiber lumen 309 and end emitting fiber lumen 310 is formed to have an inner diameter that is greater than the outer diameter of the radially emitting fiber 301 and end emitting fiber 302, respectively. This allows the fibers 301 and 302 to slide inside their respective lumens. This has an impact of reducing tensile and bending stresses produced within the fibers when the infusion shaft 300 is bent in comparison to stresses that would otherwise exist if the fibers were longitudinally fixed inside their lumens. According to some implementations one or both of the radially emitting fiber lumen 309 and end emitting fiber lumen 310 has diameter that is up to 30% greater than the respective outer diameter of the radially emitting fiber 301 and end emitting fiber 302.

According to some implementations the infusion shaft 300 is: 1) constructed so that one or both of the radially emitting fiber 301 and end emitting fiber 302 is able to slide within its respective lumen 309 and 310, and 2) constructed to limit or prevent the infusion shaft from bending beyond a minimum bending radius associated with one of the radially emitting fiber 301 and end emitting fiber 302.

Figure 11A:
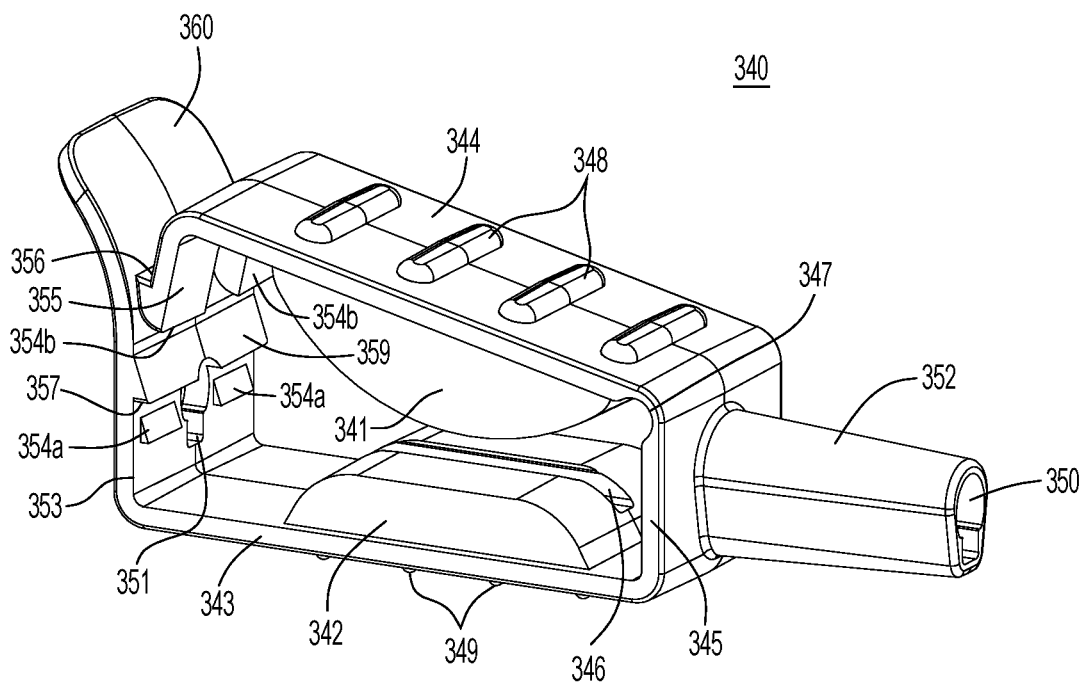
FIG. 11A illustrates an implementation of a clamp used to close off flow through an infusion shaft with the clamp being in the open position.
Figure 11B:
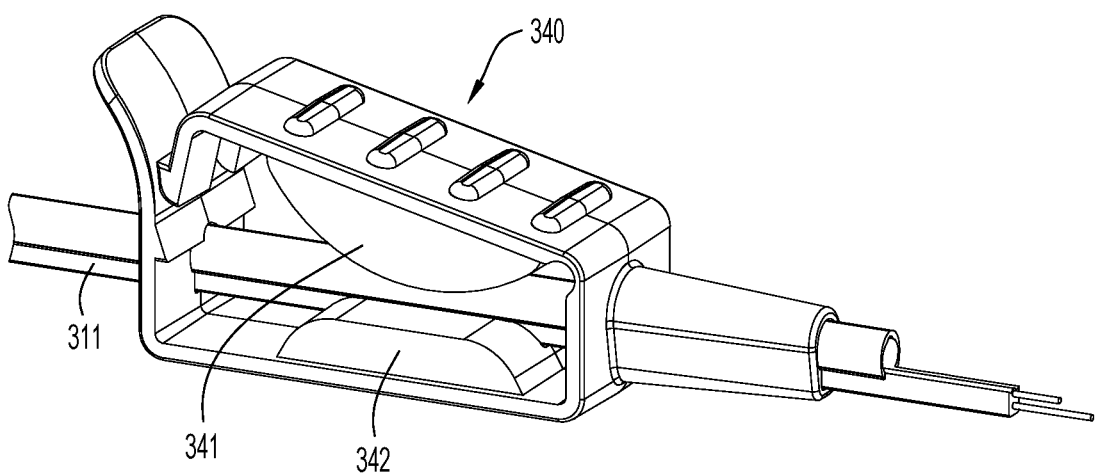
FIG. 11B illustrates the clamp of FIG. 11A being in the closed position.

FIG. 11A shows an implementation of the clamp 340 used to close off flow through the infusion shaft 300 with the clamp being in the open position. FIG. 11C illustrates the clamp of FIG. 11A being in the closed position. FIG. 11B illustrates the infusion shaft 300 running through the clamp of FIG. 11A with the clamp being in the open position.

Because the core and cladding of optical fibers 301 and 302 are susceptible to breakage when the infusion shaft is bent and/or twisted, according to some implementations the clamp 340 is keyed at its proximal and distal ends to the infusion shaft 300 as shown in FIG. 11B to prevent the shaft from twisting during a closing of the clamp onto the shaft. As discussed above, the groove 346 in the lower pad 342 serves the same function. To further guard against the breakage of the optical fibers 301 and 302 during and after the closure of the clamp 340, according to some implementations the upper and lower pads 341 and 342 of the clamp are compliant enabling them to at least partially conform to the outer profile of infusion shaft. This has the effect of distributing the force applied by the clamp 340 over a larger surface area of the infusion shaft 300. According to some implementations the upper pad 341 is assembled on a resilient arm 344 and is moved to the closing position by the application of a downward force at an end of the arm 344. According to some implementations the clamp 340 is equipped with a stop that engages the upper pad 341 and/or arm 344. The clamp 340 is configured with the stop to limit the amount by which the upper pad 341 may be moved downward against the tubular body 303 of the infusion shaft 300. The downward movement of the upper pad 341 is restrained sufficiently to limit the amount of force it is capable of applying to the tubular body 303 so as to inhibit or prevent a breaking of one or both of fibers 301 and 302 while at the same time accommodating a closing of the infusion shaft lumen 308. As shown in FIG. 11A, according to one implementation the stop 354 is in the form of one or more tabs that protrudes outward from the distal wall 353 of the clamp. The tabs 354a are configured to abut bottom portions 354b of the arm latch 355 to limit downward movement of the arm 344 and upper pad 341.

According to some implementations the clamp 340 includes a base 343 and an arm 344 that are connected by a vertically extending proximal wall 345. A hinge 347 provided between the proximal wall 345 and arm 344 enables the arm to be resiliently moved downward toward the base 343 when a force is applied to the top surface of the arm. Slip resistant grips 348 and 349 are respectively provided on both the top surface of the arm 344 and on the bottom surface of the base 343. According to some implementations the grips 348 and upper pad 341 comprise a unitary structure with the grips protruding upward from the upper pad into apertures formed in the arm 344. Likewise, according to some implementations the grips 349 and lower pad 342 comprise a unitary structure with the grips protruding downward from the lower pad into apertures formed in the base 343.

Keying the clamp 340 to the infusion shaft 300 occurs by a passing of the infusion shaft 300 through key openings 350 and 351 in the clamp having a same or similar profile of the shaft. In the implementation of FIGS. 11A-C key opening 350 extends through the proximal wall 345 and through a proximally extending protrusion 352. Although the proximally extending protrusion 352 is not required, it advantageously contributes to preventing a twisting of the infusion shaft in the clamp 340 by increasing the length of the infusion shaft 300 that is restrained. Key opening 351 is located in a distal wall 353 of the clamp.

A closing of the clamp 340 from an open position to a closed position occurs when a downward force is applied to the top surface of arm 344. A distal end of the arm 344 includes a latch 355 having an upward facing shelf 356 that is configured to engage with a downward facing shelf 357 on the distal wall 353 to lock the clamp in a closed position as shown in FIG. 11C. During the closing operation the latch 355 moves downward along the distal wall 353 over an outward sloping ramp 359 until the upward facing shelf 356 surpasses the bottom of the ramp and moves inward to rest against the downward facing shelf 357. As the latch 355 of the arm 344 passes along the ramp 359, the distal wall 353 of the clamp flexes slightly outward and then attempts to return to its original position when the upward facing shelf 356 surpasses the bottom of the ramp 359. The resilient nature and configuration of the arm 344 and distal wall 353 cause the shelves 356 and 357 to be pressed against one another to maintain the clamp 340 in a closed position as shown in FIG. 11C.

To return the clamp 340 to its open position a rearward force is applied to the curved latch release 360 that extends upward from the distal wall 353 to flex the distal wall in the direction A as shown in FIG. 11C. This has an effect of sliding the downward facing shelf 357 of the distal wall 353 off the upward facing shelf 356 of latch 355. When this occurs, the arm 44 returns to its biased open position as shown in FIGS. 11A and 11B.

According to some implementations the clamp 340 and the proximal connector 304 of the infusion shaft 300 comprise a unitary structure with the clamp protruding from the distal end of the proximal connector. According to such implementations the proximal connector 304 and clamp 340 may be injection molded as a single piece. The proximal connector is discussed in detail below.

Figure 12:
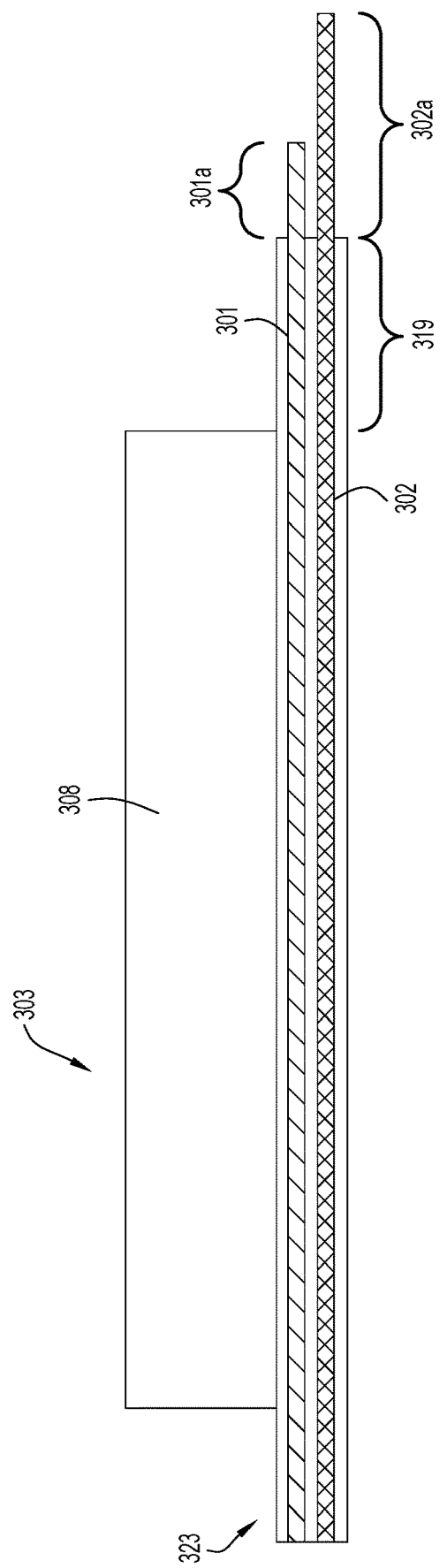
FIG. 12 is a cross-section side view of a tubular body of an infusion shaft according to one implementation.
Figure 13:
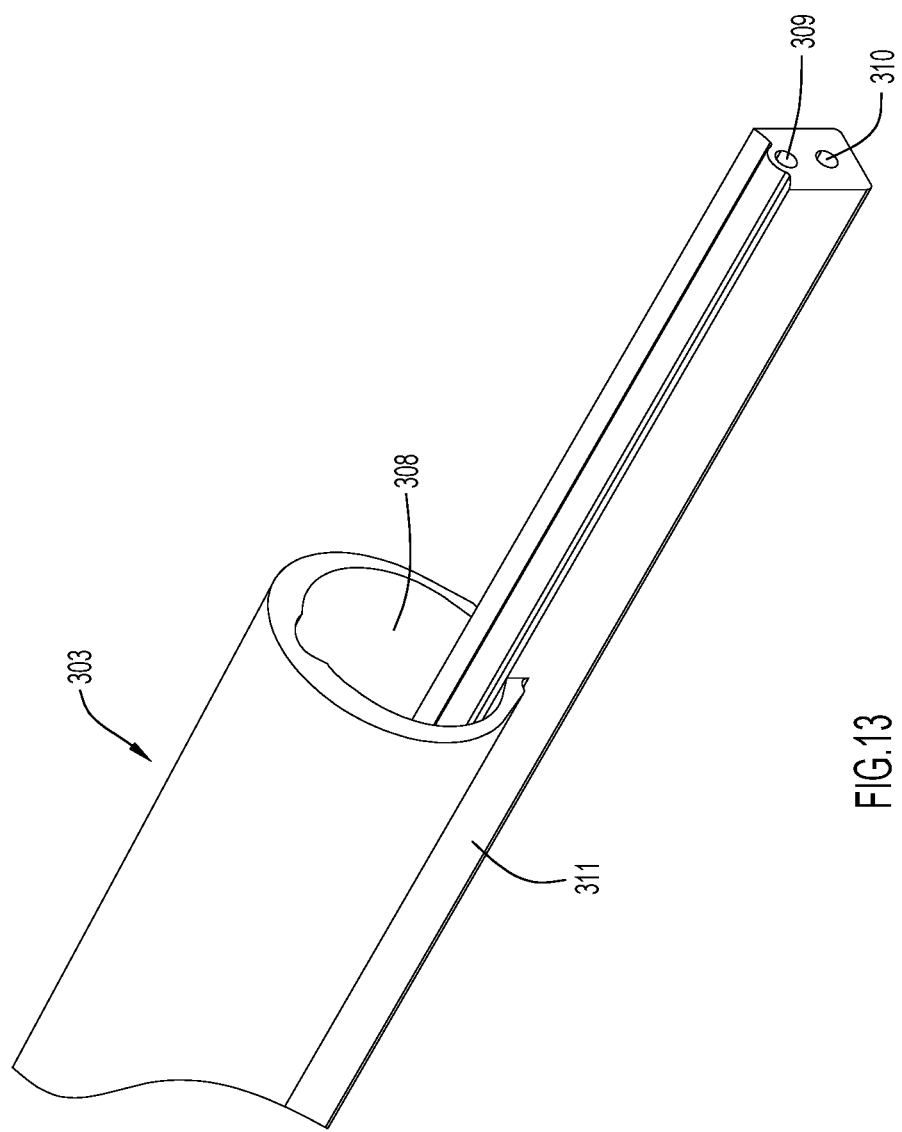
FIG. 13 is a perspective view of the proximal end portion of the tubular body of FIG.

As discussed above, the working lumen 308 of the infusion shaft 300 is coupled to a working lumen of the main shaft 200 through a connection that occurs inside the hub 400. A detailed description of the hub 400 is provided below. In addition, according to some implementations the radially emitting fiber 301 and end emitting fiber 302 are introduced into the key portion 311 of the infusion shaft 300 via the hub 400. Thus, according to some implementations both the radially emitting fiber 301 and end emitting fiber 302 run the entire length of the tubular body portion 303 of the infusion shaft 300 as shown in FIG. 12, while in other implementations the radially emitting fiber 301 runs less than the entire length of the tubular body. As discussed above, the tubular body 303 is connected to a proximal connector 304 through which therapeutic agents and/or medical instruments are introduced into the infusion shaft 300. FIG. 13 shows a perspective view of a proximal end segment 319 of the tubular body 303 according to one implementation.

Figure 14A:
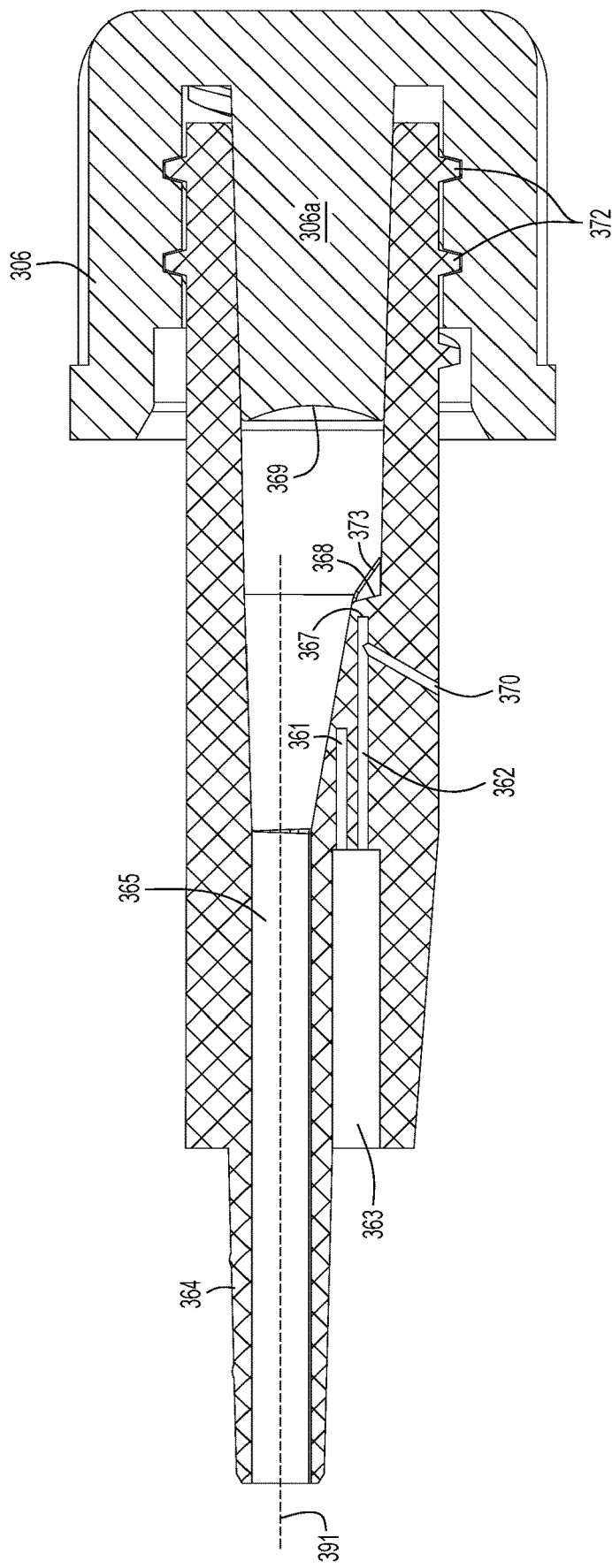
FIG. 14A is a cross-section side view of an infusion shaft proximal connector according to one implementation.
Figure 14B:
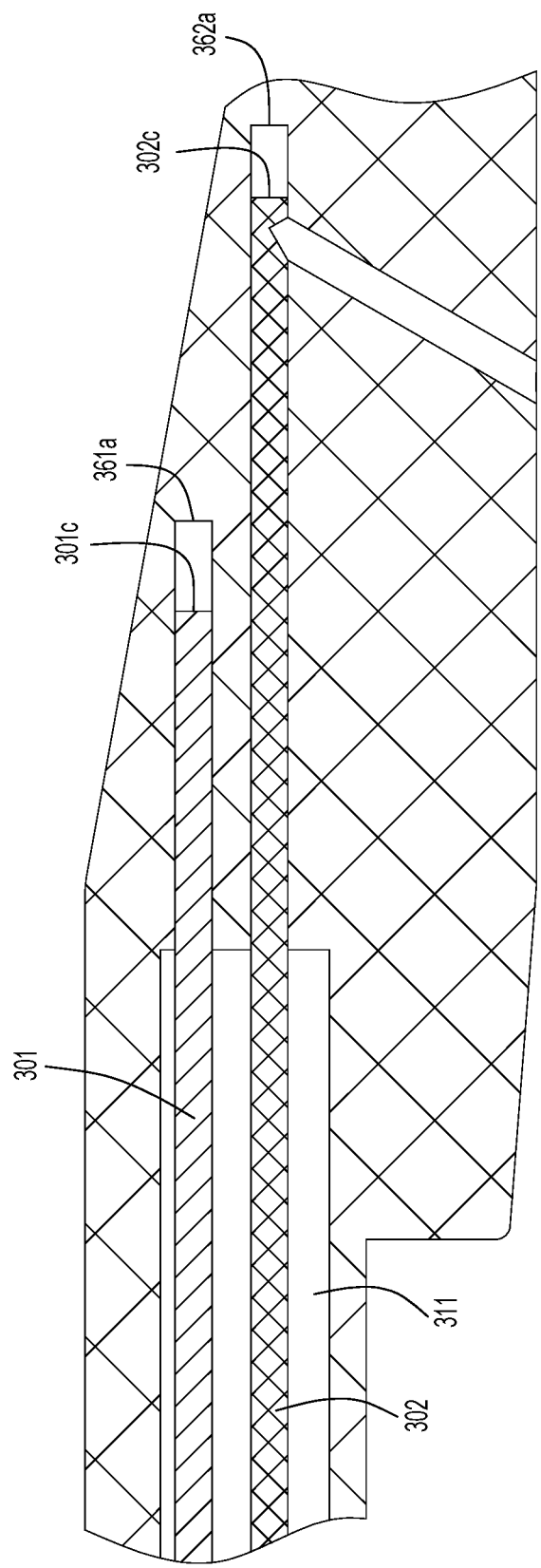
FIG. 14B is a cross-section view showing the proximal end segment of the key portion of the tubular body inserted into the receiving lumen of the proximal connector.
Figure 16:
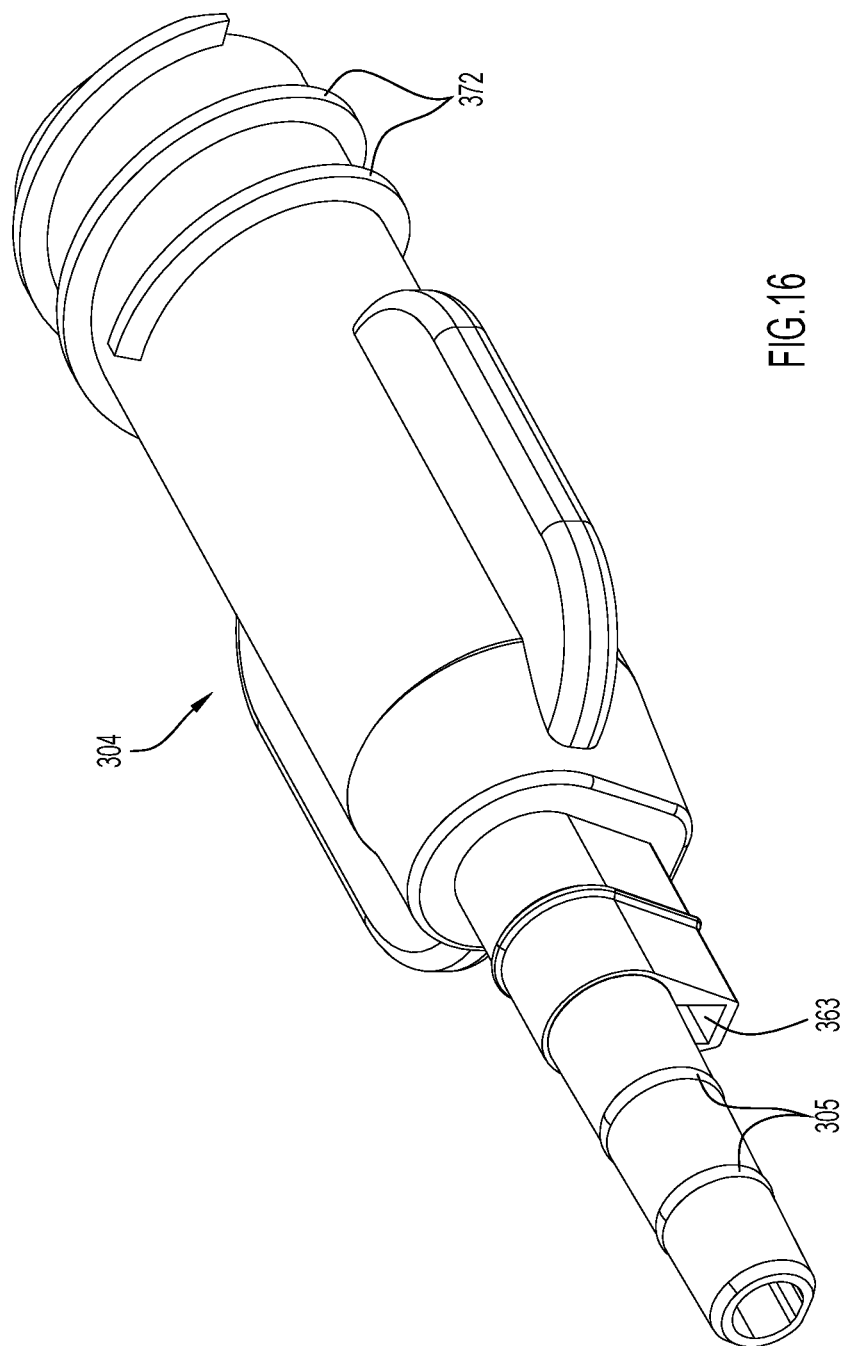
FIG. 16 is an external perspective view of an infusion shaft proximal connector according to one implementation.

FIG. 14A illustrates a cross-section side view of a proximal connector 304 to which the proximal end of the tubular body 303 of FIG. 12 is attached. FIG. 16 is an external perspective view of the proximal connector of FIG. 14A. FIG. 14B shows a partial cross-section view of the proximal connector 304 with the end segment 319 of the key portion 311 of the tubular body 303 fully inserted into a receiving lumen 363 of the proximal connector. According to some implementations the entirety of proximal connector is made of a material that is transparent or translucent to the light emitted by the radially emitting fiber 301. According to other implementations only selected portions of the proximal connector 304 located adjacent radially emitting fiber 301 is made of a material that is transparent or translucent to the light emitted by fiber 301. In either case, the contents and/or walls of at least a portion of the inner lumen 365 of the proximal connector 304 can be exposed to the disinfecting light emitted by the radially emitting fiber 301.

In the implementation of FIG. 12 the tubular body 303 comprises the working lumen 308 and the radially emitting and end emitting fibers 301, 302 residing in their respective lumens 309, 310 inside the key portion 311 of the tubular body. A proximal end section of the tubular body 303 is skived so that the end segment 319 of the key portion 311 extends proximal to the proximal end of the working lumen 308. The distal end 323 of the tubular body 303 that resides inside the hub 400 may also be skived. As shown in FIGS. 12, 14A, and 14B, an end portion 301a of the radially emitting fiber 301 and an end portion 302a of the end emitting fiber 302 protrude from the proximal end of the key portion 311 of the tubular body 303 and reside respectively within lumens 361 and 362 located in the proximal connector 304. In the implementation of FIG. 14B the end portions 301a and 302a of the fibers 301 and 302 are shorter than the respective lumens 361 and 362 they reside in. Although the length of the fibers 301 and 302 can be selected to cause their ends 301c and 302c to abut the end walls 361a and 362a of the lumens 361 and 362, the provision of gaps as shown in FIG. 14B advantageously allows for less restrictive tolerances (reducing manufacturing costs) and minimizes the risk of damaging the fibers 301 and 302 when the CVC 100 is assembled.

Figure 15:
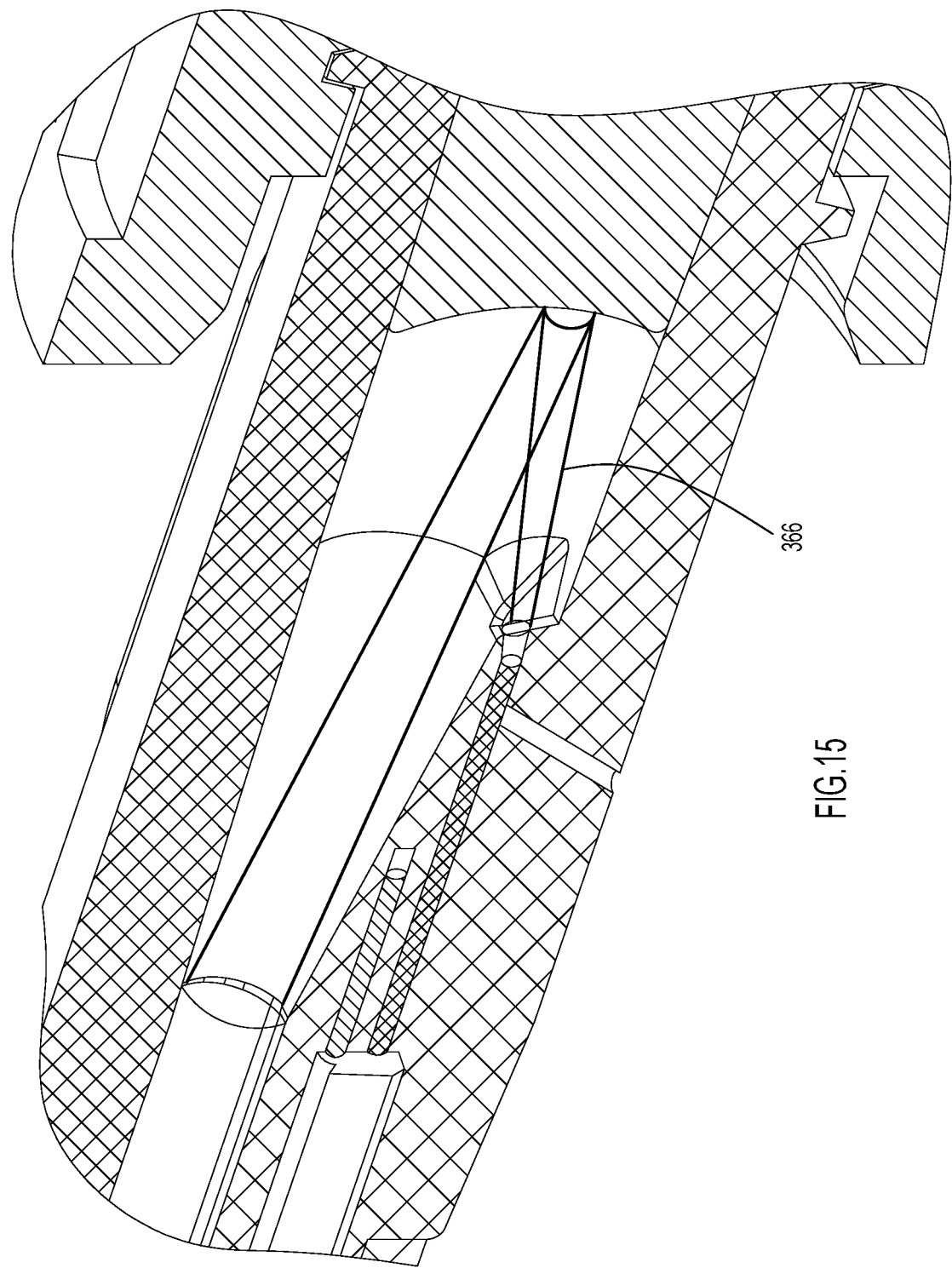
FIG. 15 illustrates a path of the light emitted by the end emitting fiber through the proximal connector of FIG. 13.

Again with reference to FIG. 14A, the proximal connector 304 further comprises features for directing the light 366 emitted from the end emitting fiber 302 into the internal space of the proximal connector. FIG. 15 shows a ray tracing of the light 366 dispersed inside the proximal connector 304 according to one implementation. The light emitted by the end emitting fiber 302 passes through a first optical surface/lens 367 and a second optical surface/lens 368 that act to alter the trajectory of the light so that it impinges on a light reflector 369 positioned on, or otherwise integrated into, a distal facing surface of a central portion 306a of the cap 306. According to some implementations the first and second optical surfaces 367 and 368 have an RMS surface roughness of less than 180 angstroms.

According to some implementations the trajectory of the disinfecting light is altered as a result of being refracted by each of the first and second optical surfaces 367 and 368. Optical surfaces of this type are also referred to herein as "refractive optical surfaces". (Refraction is a deflection from a straight path undergone by a light ray or energy wave in passing obliquely from one medium (such as air) into another (such as glass) in which its velocity is different.) That portion of the proximal connector 304 residing between the first and second optical surfaces is a material that is substantially transparent or at least translucent to the light emitted by the end emitting fiber 302. According to some implementations the material is a Teflon or a polycarbonate.

In the implementation of FIG. 15, the first and second optical surfaces/lenses 367, 368 and the light reflector 369 are arranged in the proximal connector 304 to cause the light emitted from the end emitting fiber 302 to flood at least a portion of the length of the inner lumen 365 of the proximal connector and/or at least a portion of the inner lumen 308 of the tubular body 303. According to some implementations this length of the inner lumen 365 is out of reach of the disinfecting light emitted by the radially emitting fiber 301. In the implementation of FIG. 15, however, there is an overlapping of the light paths that emanate from fibers 301 and 302 along at least a portion of the length of the inner lumen 365. Thus, when the fibers 301 and 302 are both illuminated this has an effect of providing not just one, but two doses of disinfecting light in the overlapping region.

According to some implementations an index matching material, such as a gel or adhesive, is positioned in the gap that separates the end 302c of the end emitting fiber 302 from the end wall 362a of lumen 362. The index matching material is selected to have a refractive index between that of the core of the end emitting fiber 302 and that of the first optical surface 367 formed in or located on the end wall 362a of lumen 362. During an assembly of the CVC 100 the index matching material may be introduced into the gap via a port 370 located in a side of the proximal connector.

The first optical surface/lens 367 resides at the inner surface of the end wall 362a of lumen 362. According to some implementations the inner surface of the end wall 362a is of optical quality that minimizes a scattering of the light emitted by fiber 302 so that the vast majority of the disinfecting light entering the surface/lens 367 is directed onto the second optical surface/lens 368. In a like manner, the second optical surface/lens 368 of optical quality so that a vast majority of the disinfecting light that enters the surface/lens 368 is transported to the cap light reflector 369 and then onto the contents and/or inner walls of the inner lumen 365 of the proximal connector.

Figure 19A:
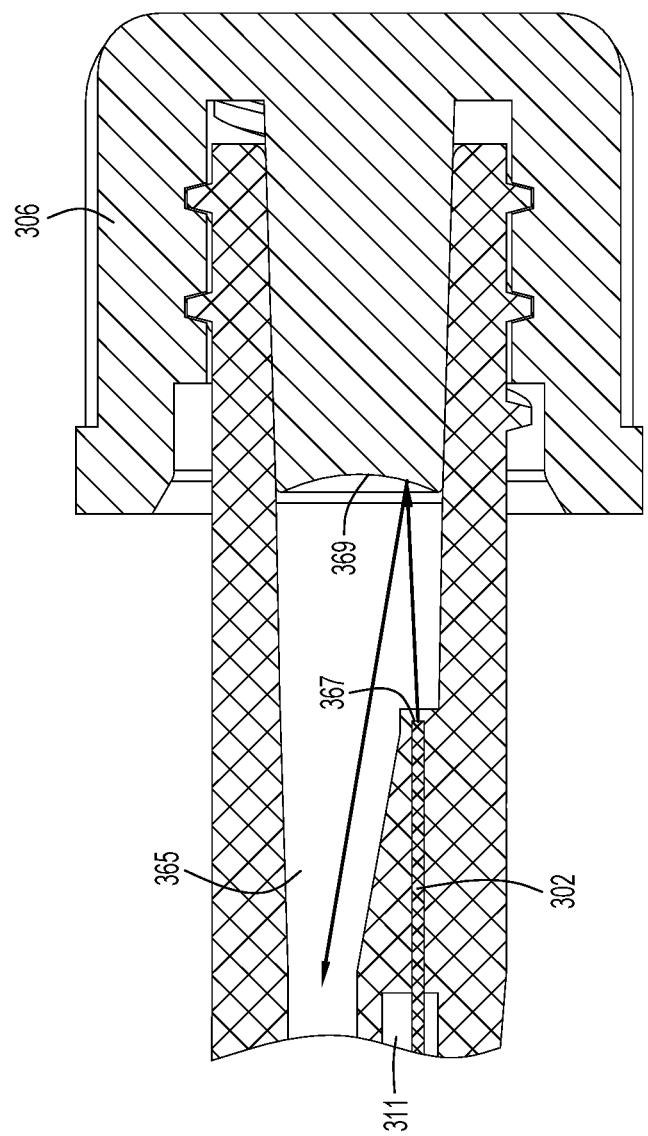
FIGS. 19A-D illustrate cross-section side views of a portions of an infusion shaft according to other implementations.

According to some implementations the first optic surface/lens 367 is arranged perpendicular to a longitudinal axis 373 of the proximal connector 304 and the second optical surface/lens 368 is positioned at an angle relative to the longitudinal axis. The angle by which the second optical surface/lens 368 if tilted with respect to the longitudinal axis 391 is selected to assist in diverting the light exiting the lens upward toward a selected portion of the cap reflector 369. According to some implementations the lens 368 is tilted an angle less than 20 degrees in relation to the plane orthogonal to the longitudinal axis 391. According to some implementations, like that shown in FIG. 19A, the second optical surface/lens 368 is dispensed with and the first optical surface/lens 367 is angled to assist in directing the light emitted by the end emitting fiber 302 to impinge on a location of the cap light reflector 369 that causes the light to flood at least a portion of the length of the internal lumen 365 of the proximal connector and/or at least a portion of the internal lumen 308 in the tubular body 303. An exemplary light path of such implementations is shown by the arrows in FIG. 19A. This can occur by bending the distal end portion of the lumen 362 upward so that it is not parallel to the longitudinal axis 391 of the proximal connector 304 as shown in FIG. 19A. In this way a direct optical path between the first optical surface/lens 367 and the reflector 369 may be established.

Figure 18:
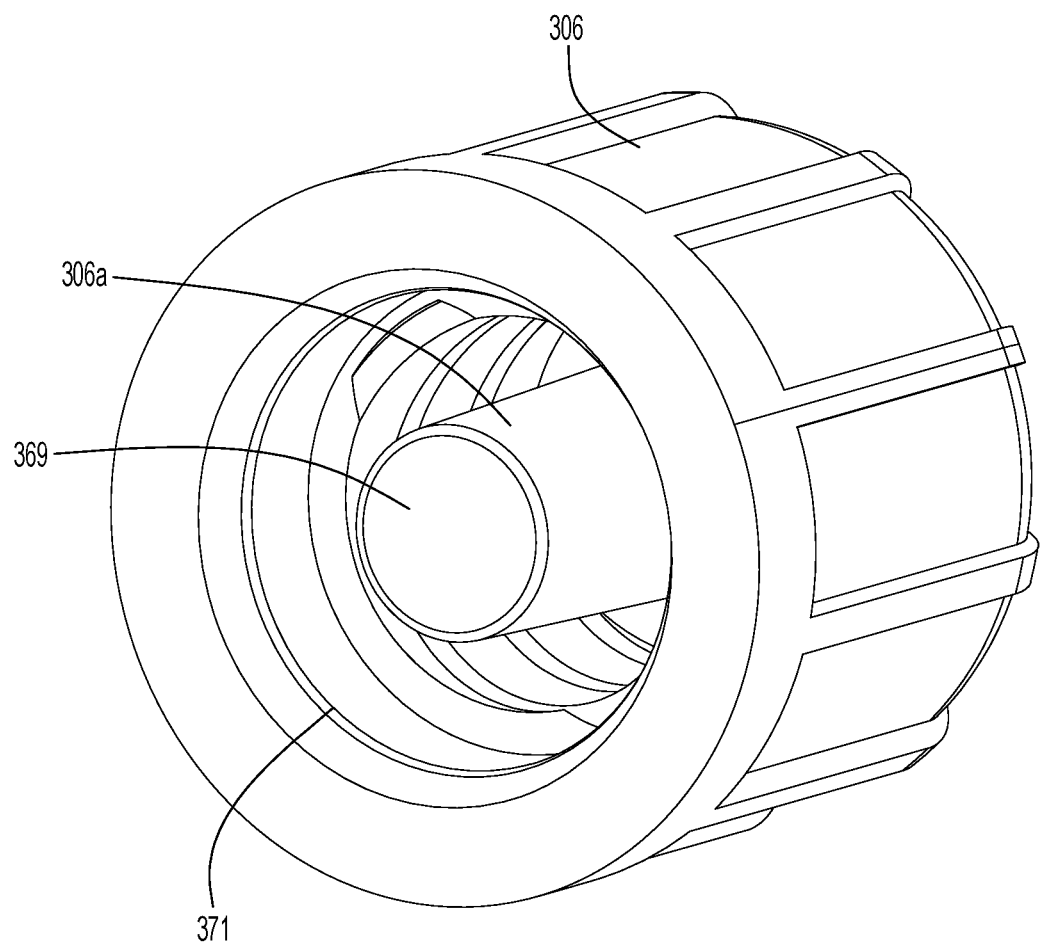
FIG. 18 is a perspective view of the cap of FIG. 13.

The cap light reflector 369 may comprise any shape that is capable of causing the light impinged upon it to be reflected down at least a portion of the inner lumen 365 of the proximal connector 304. According to some implementations the cap reflector 369 comprises a concave or convex surface having a radius of curvature suitable for establishing a desired light path down the inner lumen 365 of the proximal connector. According to other implementations the reflector 369 may comprise a flat surface that may or may not be oriented at an angle in relation to the longitudinal axis 373 of the proximal connector 304. FIG. 18 is a perspective view of the proximal connector cap 306 according to one implementation. As also shown in FIG. 14A, the cap 306 has internal threads 371 that mate with external threads 372 of the proximal connector that allow that cap to be fixed to and removed from the proximal connector.

Figure 17:
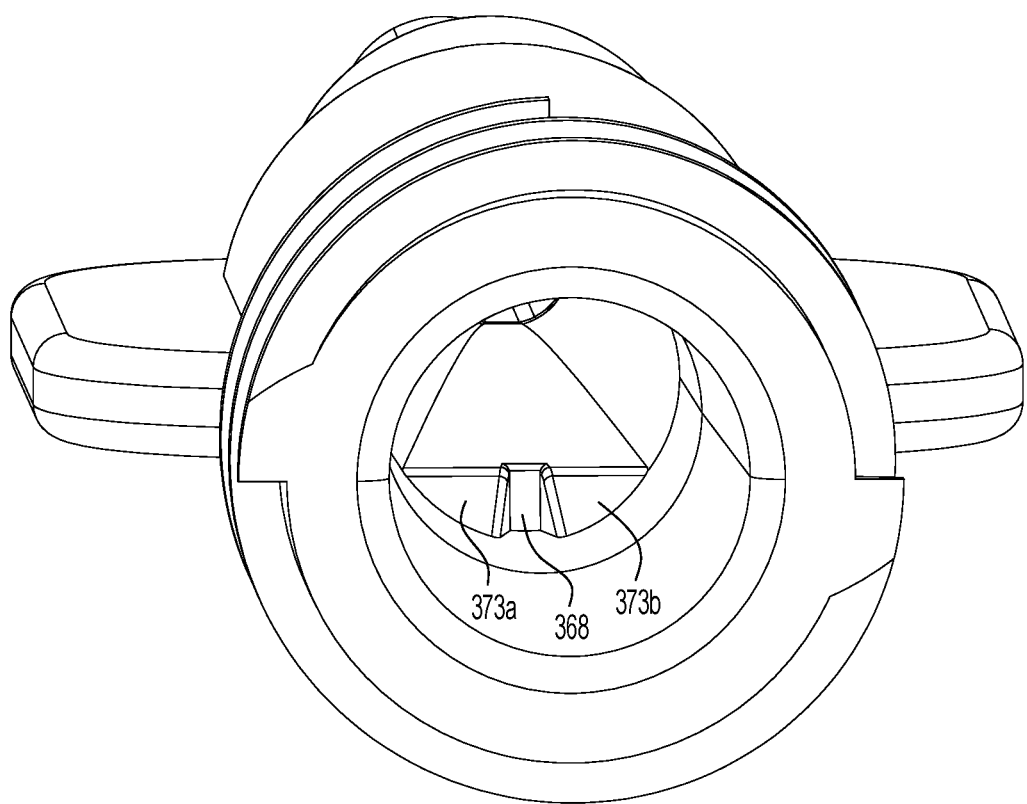
FIG. 17 is an internal view of the guidewire ramp and optical surface of FIG. 13.

As best seen in FIGS. 14A and 17, according to some implementations the proximal connector 304 is equipped with a ramp 373 that is configured to facilitate an advancement of a medical instrument through the lumen 365 of the proximal connector. The medical instrument may be, for example, a guidewire. In the implementation of FIG. 17 the ramp 373 comprises a first part 373a and a second part 373b that reside on opposite sides of the second optical surface 368 so that there exist a direct line of sight between the second optical surface/lens 368 and the cap reflector 369.

In accordance with some implementations disclosed herein each of the radially emitting fiber 301 and end emitting fiber 302 emits blue light at a wavelength of between 380-495 nm and an exposure of between 100-1,000 Joules/cm2 is employed to kill the unwanted bacteria. According to other implementations fibers 301 and 302 emit ultra-violet light at a wavelength of 100-400 nm and exposure up to 6 J/cm$^2$ to kill unwanted bacteria.

Figure 19B:
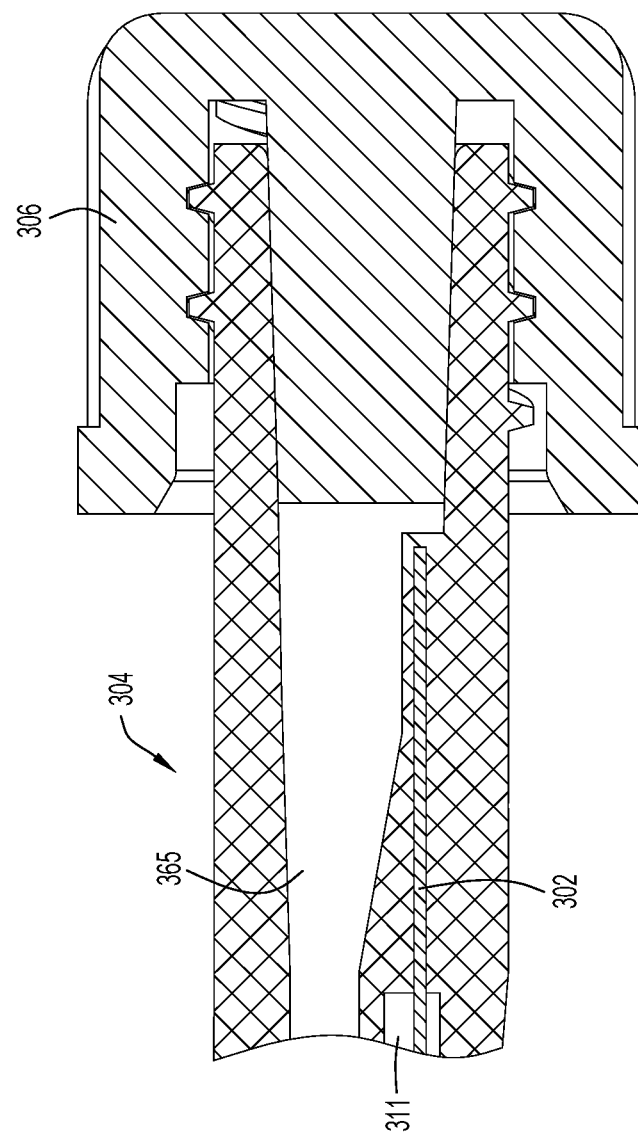

In the infusion shaft 300 implementations discussed above, both a radially emitting fiber 301 and an end emitting fiber 302 are used to effectuate a disinfection of the infusion shaft. However, according to other implementations only one of a radially emitting fiber and an end emitting fiber is used. For example, according to some implementations disinfection predominately occurs inside the proximal connector 304 by use of the end emitting fiber 302 and the radially emitting fiber 301 is dispensed with altogether as shown in FIG. 19A. According to other implementations the end emitting fiber 302 is dispensed with and the radially emitting fiber 301 alone is used to disinfect at least a portion of the tubular body 303 and at least a portion of the proximal connector 304 of the infusion shaft 300 as shown in FIG. 19B. According to implementations that do not include an end emitting fiber the radially emitting fiber 302 may extend proximally inside the proximal connector 304 to a location near or adjacent the distal end of the cap 306 when the cap is fully threaded onto the connector as shown in FIG. 19B. In this manner the radially emitting fiber 301 is capable of disinfecting a greater length of the proximal connector.

Figure 19C:
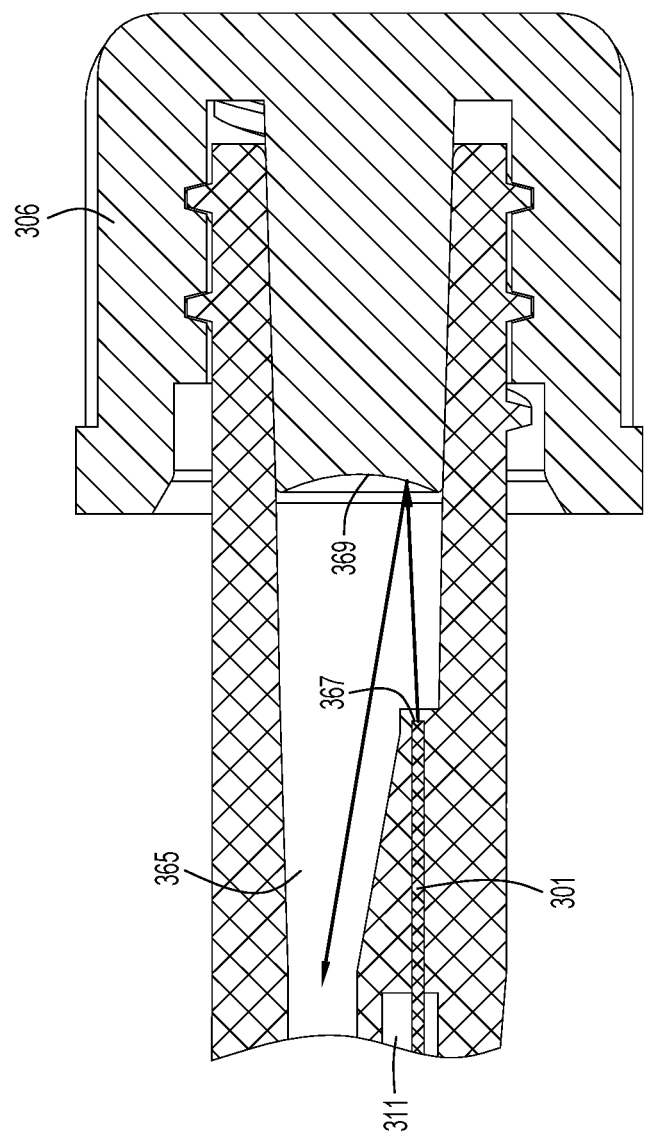

According to some implementations the radially emitting fiber 301 is also configured to emit light from an end thereof. According to such implementations the light emitted from the end of the radially emitting fiber 301 may be delivered to a target location inside the proximal connector 304 and/or a target location inside the tubular body 303 of the infusion shaft by the use of one or more optical surfaces and/or one or more reflectors similar to the concepts described above and below in conjunction with the examples of FIGS. 14A, 14B, 20A, 20B, 21A and 21B. For example, as shown in FIG. 19C, disinfecting the infusion shaft 300 may occur by use of a radially emitting fiber 301 that emits light radially along its length and also emits light from a distal end of the fiber. Like the implementation of FIG. 19A, an optical surface 367 and reflector 369 may be used to distribute the light emitted from the end of the radially emitting fiber 301 into the proximal connector.

A majority of the light transmitted by a radially emitting fiber is typically emitted radially from the fiber with a smaller amount being emitted from the end of the fiber. For example, the Fibrance® Light Diffusing Fiber manufactured by Corning® Incorporated has a diffusion length that is characterized by an emitting of 90% of its light radially along its length with the remaining 10% being emitted from its end. These percentages will vary among different radially emitting fibers and are typically established by the fiber manufacturer. Because it may be desirable to use the light emitted from the end of the radially emitting fiber to disinfect an object, like in the example of FIG. 19C, the percentage of light emitted through the end of the radially emitting fiber may be increased by cutting short the length of the fiber. For instance, a radially emitting fiber that has a given diffusion length that results in 90% of its light being radially emitted with the remaining 10% being emitted from its end can be cut short to cause a percentage increase in the amount of light being emitted from the end. For example, the radially emitting fiber may be cut by a certain length to cause a decrease in the amount of light that is radially emitted and an increase in the amount of light that is end emitted. According to some implementations the radially emitting fiber is cut short to cause 50-80% of the light to be radially emitted and correspondingly 50-20% of the light to be end emitted.

According to other implementations the radially emitting fiber may itself be engineered to obtain a desired distribution of light from its sides and end. This can be achieved, for example, by altering the amount of nano-sized structures doped within the fiber. According to some implementations the radially emitting fiber is engineered to cause 50-90% of the light to be radially emitted and correspondingly 50-10% of the light to be end emitted. According to other implementations the radially emitting fiber is engineered to cause 50-80% of the light to be radially emitted and correspondingly 50-20% of the light to be end emitted.

It is important to note that multiple radially emitting fibers and/or multiple end emitting fibers may be used to disinfect the infusion shaft 300.

In regard to both the main shaft 200 and the infusion shaft 300, when a radially emitting fiber that emits light from an end thereof is used, the end of the radially emitting fiber may be coated with a reflective material, such as gold, to direct the light that would otherwise be lost out the end of the fiber back into the fiber core. Alternatively, the end of the radially emitting fiber may be fitted within a cap that has an internal reflective surface that causes at least a portion of the light emitted from the end of the fiber back into the fiber. Reflecting the light back into the fiber advantageously increases the amount of light emitted along the length of the radially emitting fiber.

The laser induced damage threshold, or the ability to propagate light of a given power density, varies among material types. For example, a fiber optic core comprised of fused silica glass may have a higher tolerance to laser damage than a polymer. The power density of light emitted by a multimode type end emitting fiber can be high as a result of essentially the totality of the light input being emitted from the end of the small diameter core. The power densities of the light emitted by the multimode type end emitting fiber may exceed the capabilities of the materials selected for injection molded optics or casted hubs. To alleviate this problem, according to some implementations the end emitting fiber 302 is equipped with an end cap that reduces the power density of the light that leaves the end emitting fiber core.

Figure 48B:
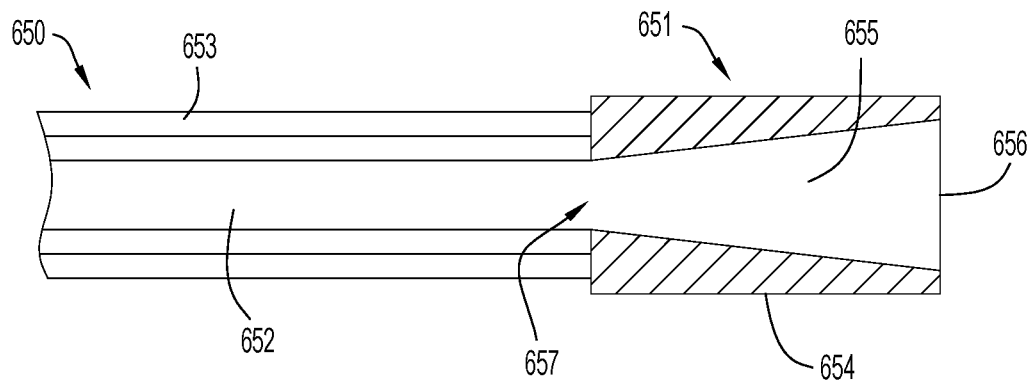
FIG. 48B is a cross-section view of the end emitting fiber of FIG. 48A.
Figure 48A:
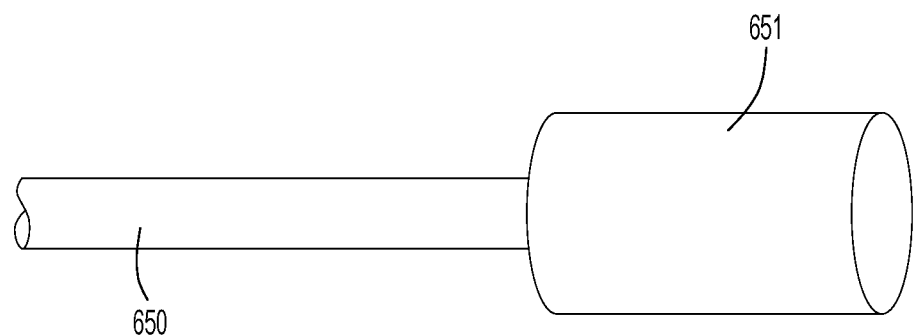
FIG. 48A is a perspective side view of an end emitting fiber having an end cap.

FIG. 48A shows a perspective side view of an end portion of an end emitting fiber 650 that has an end cap 651 attached to the end of the fiber 650. FIG. 48B shows a cross-section of the end cap according to one implementation. The fiber includes a glass or polymer core 652 and a cladding 653 disposed about the core. The end cap 651 includes a cylindrical body 654 that houses a medium 655 that is optically coupled to the fiber core 652. The medium is transparent to the light it receives from the core 652 and has an index of refraction that is the same or close to that of the fiber core 652. The medium is sized and shaped so that the light that exits the end 656 of the end cap 651 has a power density that is lower than the power density of the light when it leaves the fiber core 652. This is accomplished by widening the light beam received from the fiber core. The widening of the light beam occurs as a result of the medium having a greater diameter than that of the fiber core. In the example of FIG. 48B, the diameter of the medium 655 increases between its proximal and distal ends 657 and 656, respectively. However, according to other implementations the medium may be cylindrical or spherical in shape. Coupling of the end cap medium 655 to the fiber core 652 may occur in several ways. According to one method the proximal end of the medium is fused with the fiber core. According to other implementations the medium is formed from the fiber core.

Figure 9C:
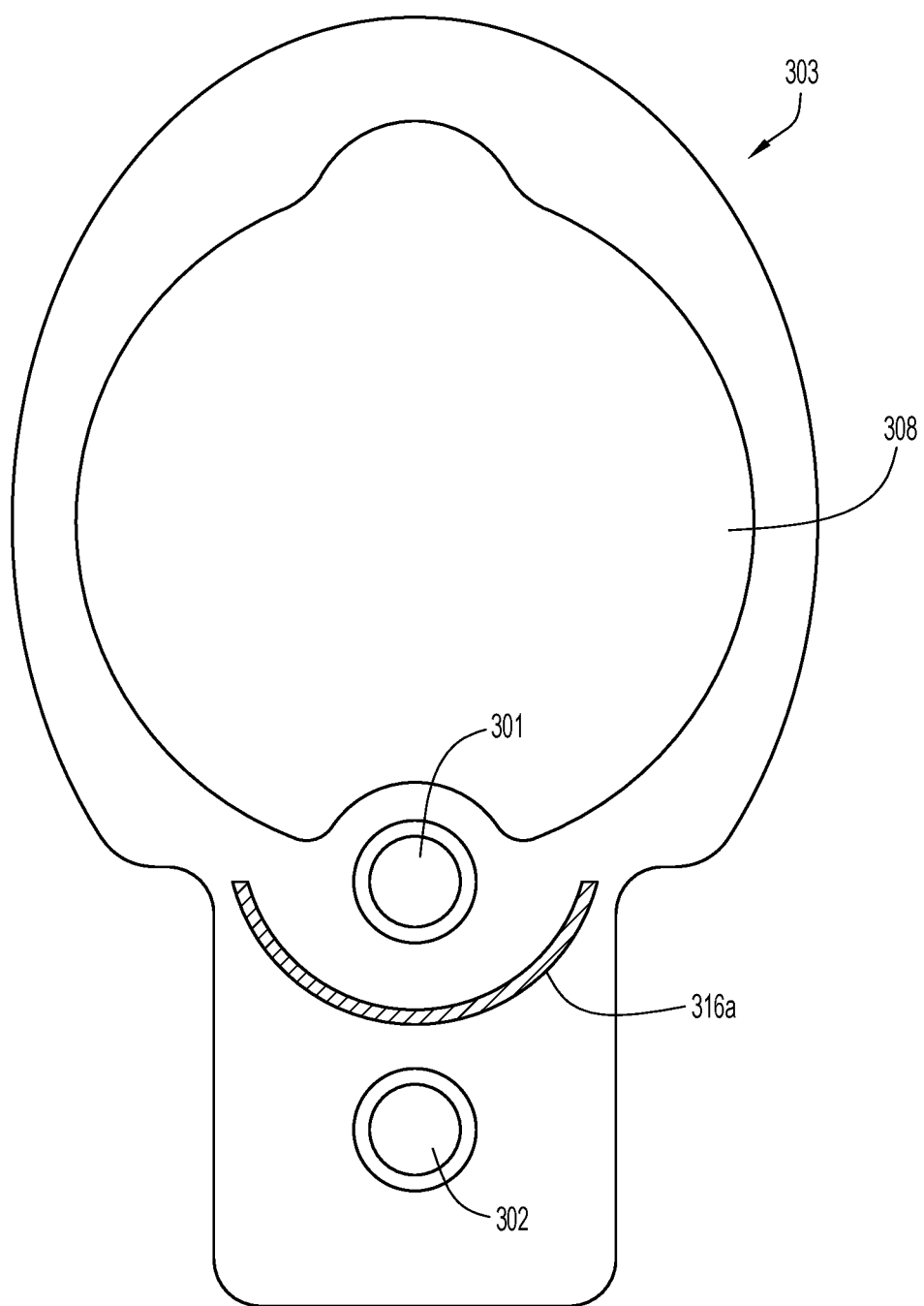
FIGS. 9C through 9F show alternative exemplary implementations of an infusion shaft having reflectors that guide the light emitted by the radially emitting fiber into the working lumen.
Figure 9D:
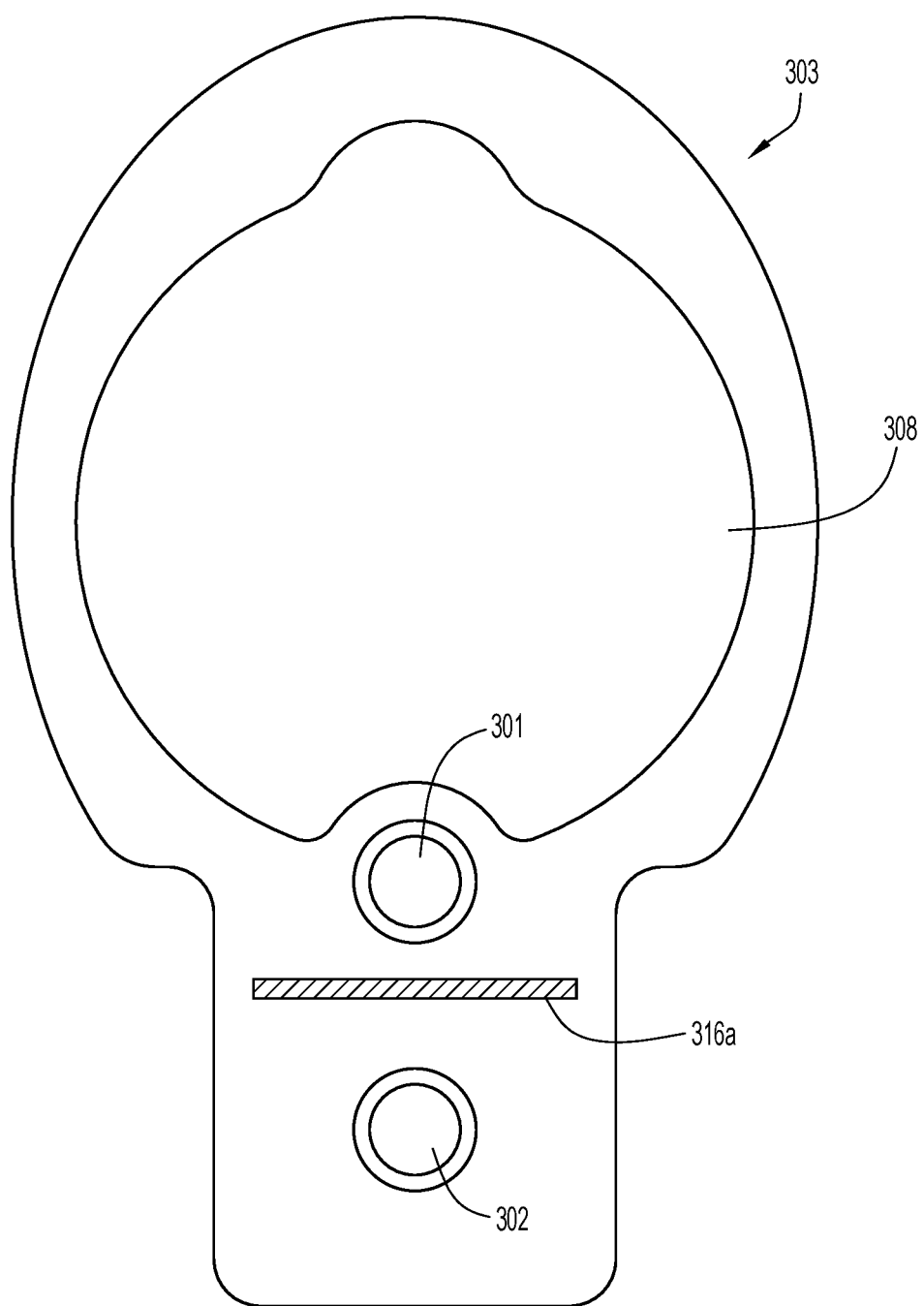

FIG. 9C illustrates a cross-section of the tubular body 303 of an infusion shaft whereby a curved reflector of light 316*a* is embedded partially surrounding the radially emitting fiber 301 to direct light emitted from the sides and bottom of the fiber 301 upward toward the internal lumen 308. FIG. 9D illustrates a similar configuration wherein the reflector 316*b* comprises a flat profile extending across at least a portion of the width of the key portion 311 of the tubular body 303. In implementations that also involve the use of an end emitting fiber 302, the reflector 316 may be located between the radially emitting fiber lumen 309 and the end emitting fiber lumen 310. According to some implementations the reflectors 316*a* and 316*b* are embedded into the tubular body 303 of the infusion shaft 300 while the tubular body is being extruded via co-extrusion process.

Figure 9E:
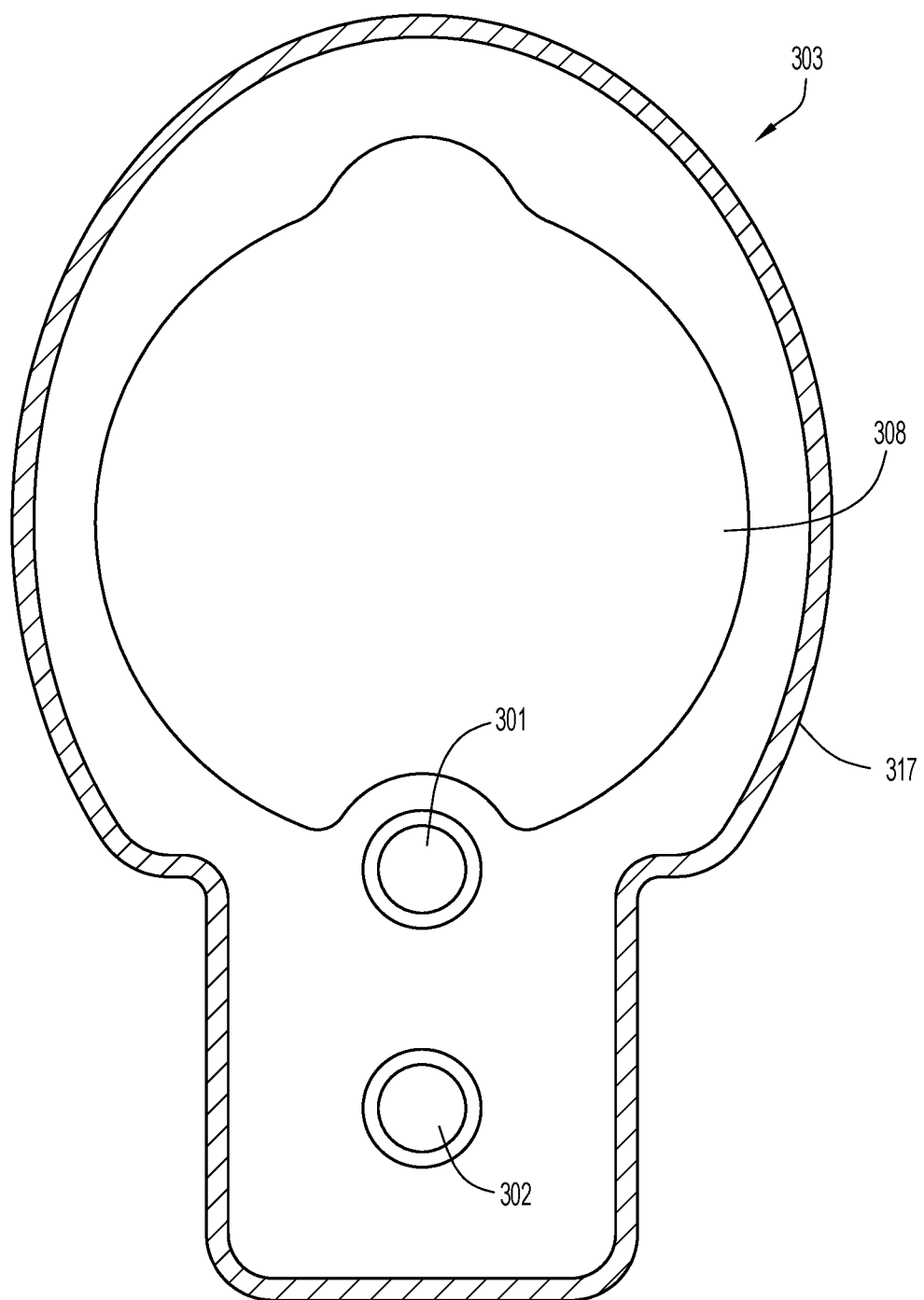
Figure 9F:
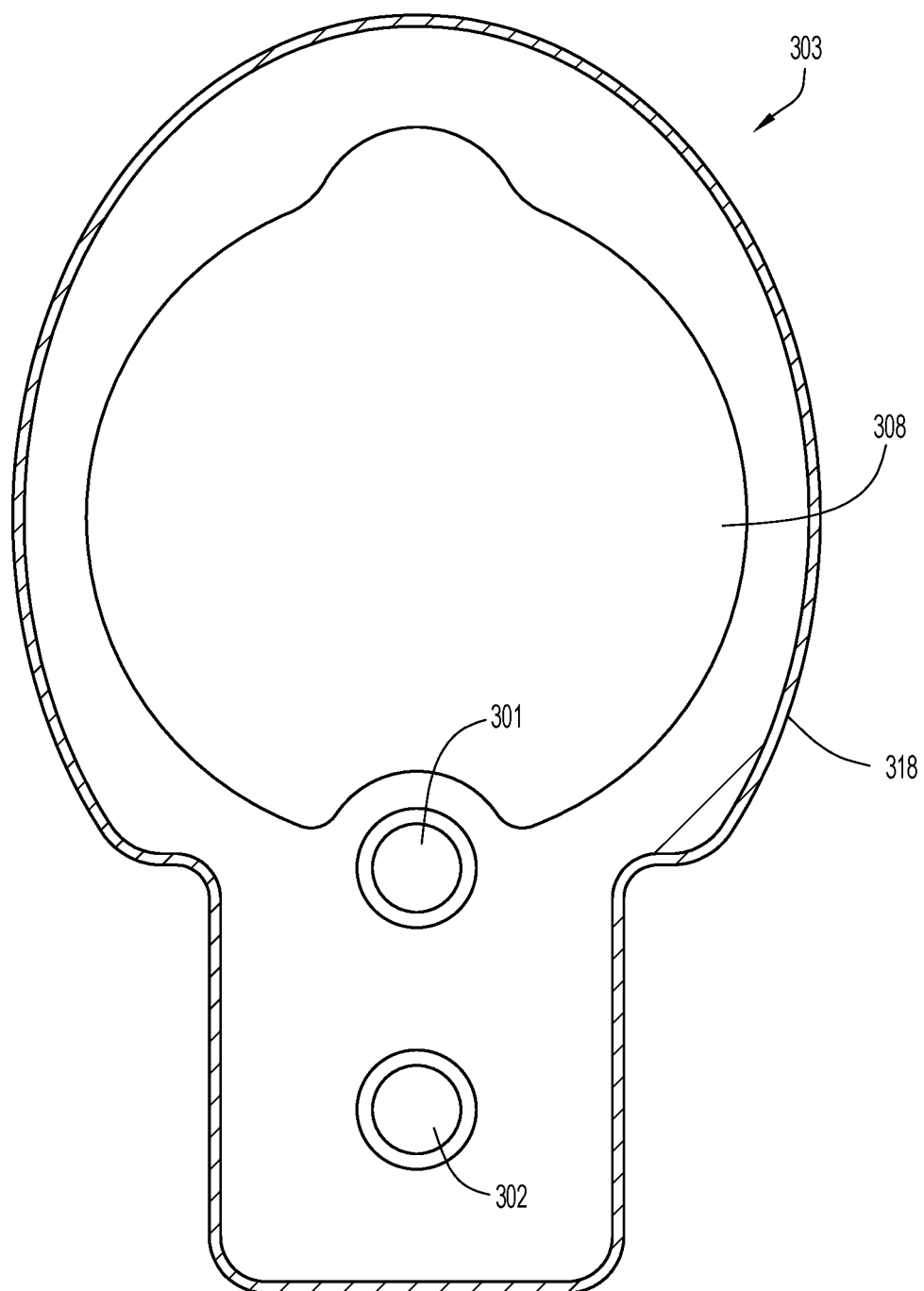

According to other implementations, that may or may not include a light reflector like that of reflector 316*a* or reflector 316*b*, at least a portion or all of the peripheral wall of the tubular body 303 is coated, wrapped or impregnated with a material that is light reflective. This advantageously results in light being reflected back into the tubular body 303 (that would otherwise escape), thereby increasing the light density within the tubular body when the radially emitting fiber is illuminated. In the implementation of FIG. 9E an outer thickness of the peripheral wall 317 of the tubular body 303 is impregnated with light reflective materials, such as, for example, aluminum particles. According to some implementations the light reflective material is impregnated into the peripheral wall during the extrusion of the tubular body 303. In the implementation of FIG. 9F the outer surface of the tubular body 303 is coated or wrapped with a light reflective material 318. According to implementations in which the outer surface of the tubular body 303 is wrapped, the wrapping may comprise a heat shrink having light reflective properties that is heat shrunk onto the outer surface. The outer surface of the tubular body 303 may also comprise a reflective film, such as a layer of light reflective paint.

According to some implementations at least a portion of the external surface of the proximal connector 304 is coated or wrapped with a light reflective material so that at least a portion of the disinfecting light delivered into the internal lumen 365 is reflected back into the lumen when the light impinges on the light reflective material. Like the tubular body 303, the proximal connector 304 may be tightly wrapped with a heat shrink that possesses a light reflective material. The external surface of the proximal connector 304 may also comprise a reflective film, such as a layer of light reflective paint. The use of the light reflective material improves internal disinfection and acts to reduce or eliminate an impingement of the disinfecting light onto the skin of the patient that could otherwise result in patient discomfort in the form of heat.

Figure 20A:
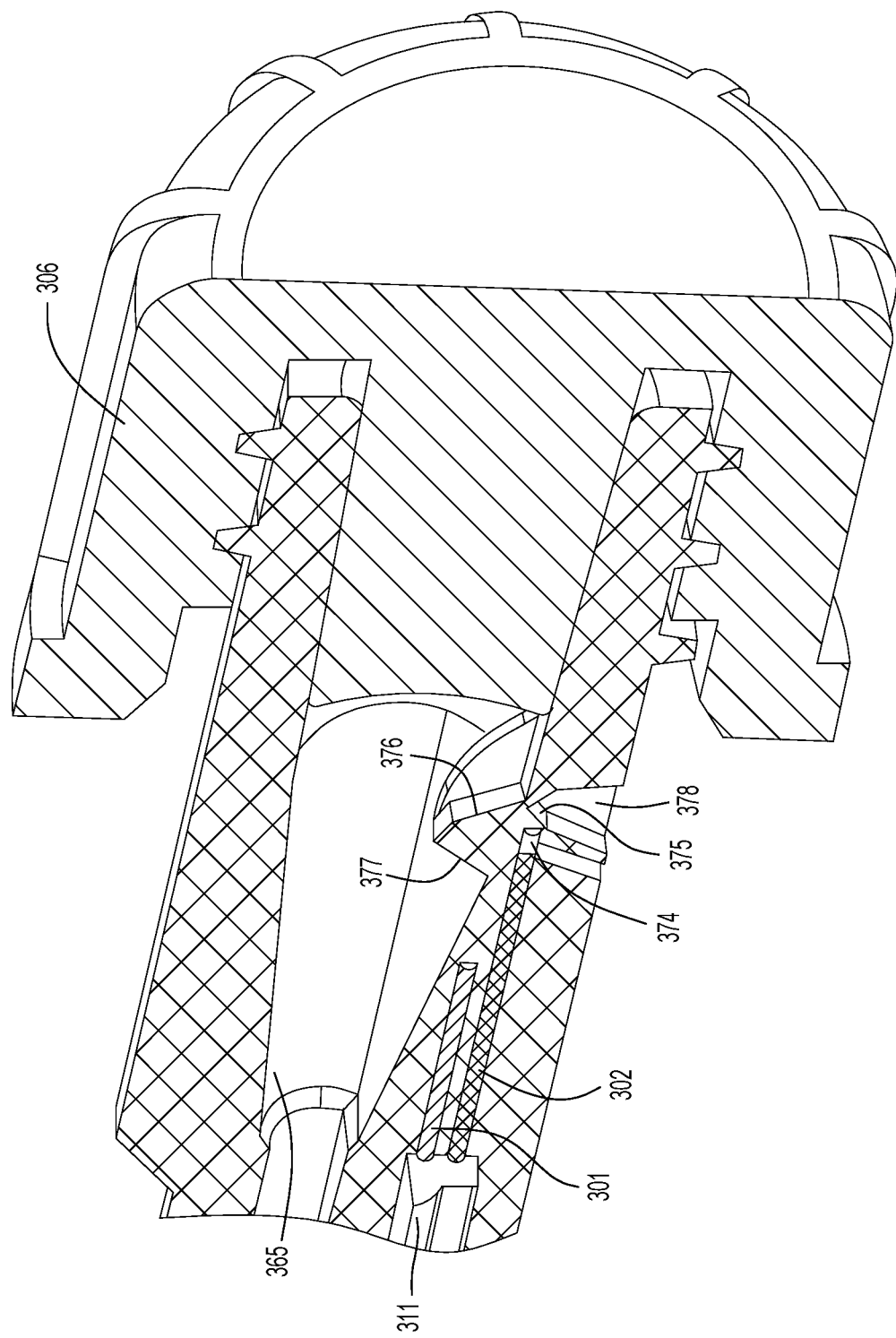
FIG. 20A is a cross-section side view of an infusion shaft proximal connector according to one implementation.

In the implementation of FIG. 14A optical surfaces 367 and 368 were used in conjunction with a light reflector 369 to direct light emitted from the end emitting fiber 302 to a target location inside the proximal connector 304. In addition, each of the optical surfaces 367 and 368 were internal to the proximal connector 304. In the implementations of FIGS. 20A and 21A optical surfaces are used to direct light emitted by the end emitting fiber 301 to its target location without the use of a light reflector. Moreover, in the implementation of FIG. 21A at least some of the optical surfaces reside on and/or in an insert residing in a side cavity of the proximal connector 304. According to some implementations one or more or all of the optical surfaces has an RMS surface roughness of less than 180 angstroms.

In each of the implementations disclosed and contemplated herein, when an end emitting fiber is used to deliver bacterial disinfecting light to a target location the end emitting fiber may be equipped with an end cap.

Figure 19D:
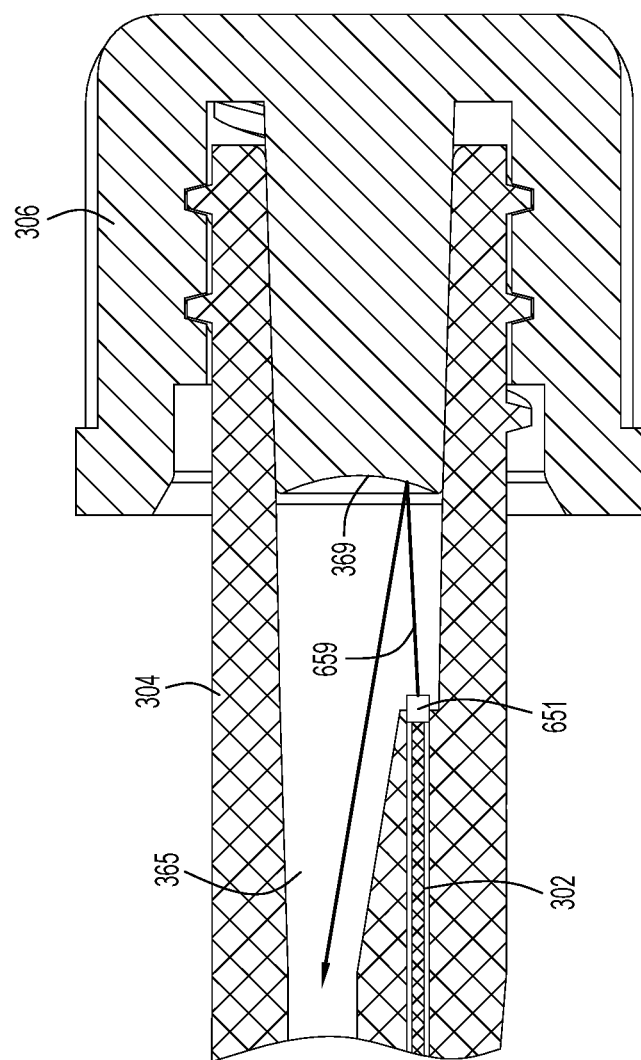

FIG. 19D illustrates an implementation in which an end cap 651 is attached to the end of an end emitting fiber 302 and used to deliver light 659 directly to the light reflector 369 of end cap 306 without the use of an optical surface. That is, no structure exits between the end of the end cap and the light reflector 369 of the end cap 306. This arrangement results in a more simple design and can increase the efficiency by which light is delivered to its target location inside the proximal connector 304 and/or tubular body 303 of the infusion shaft.

Each of the implementation of FIGS. 20A and 21A is similar to that of FIG. 14A except that no light reflector 369 is provided on the cap 306. Instead, to reflect the light these implementations use one or more optical surfaces on which total internal reflection occurs. These types of optical surfaces are also referred to herein as "total internal reflection optical surfaces".

Total internal reflection is the phenomenon which occurs when a propagated wave strikes a medium boundary at an angle larger than a particular critical angle normal to the incident surface. If the refractive index is lower on the opposing side of the boundary and the incident angle is greater than the critical angle, the wave cannot pass through and is entirely internally reflected. The critical angle is the angle of incidence above which the total internal reflection occurs. This is particularly common as an optical phenomenon, where light waves are involved.

When a wave reaches a boundary between different materials with different refractive indices, the wave will in general be partially refracted at the boundary surface, and partially reflected. However, if the angle of incidence is greater (i.e. the direction of propagation is closer to being parallel to the boundary) than the critical angle—the angle of incidence at which light is refracted such that it travels along the boundary—then the wave will not cross the boundary, but will instead be totally reflected back internally. This can only occur when the wave in a medium with a higher refractive index reaches a boundary with a medium of lower refractive index. For example, it will occur with light reaching air from plastic, but not when reaching plastic from air.

In the context of the present application, the term "reflector" and "light reflector" do not encompass a total internal reflection optical surface, but instead include polished surfaces, mirrors, metals and the like that reflect light regardless of the incident angle.

Like the implementation of FIG. 14A, in the implementation of FIG. 20A the proximal connector 304 may be made of a plastic material. Generally, plastics have an index of refraction of between about 1.4 to about 1.7 as compared to air that has an index of refraction of 1.0 and saline that has an index of refraction of 1.33. In the implementation of FIG. 20A there are first, second, third and fourth optical surfaces 374-377 used to direct light from the end emitting fiber 302 to a target location inside the infusion shaft 300.

The second and third optical surfaces 375 and 376 are each bounded on one side by the plastic material that forms the proximal connector 304 and on the other side by air in the proximal connector's manufactured state. In use, however, the internal cavity of the proximal connector may be occupied by a sterile saline solution. Thus, according to some implementations sterilization with the bacterial disinfecting light occurs when the proximal connector is filled with a saline solution. In such instances, the third optical surface 376 is bounded on one side by the plastic material (incidence medium) that forms the proximal connector 304 and on the other side by a saline solution. In regard to the second optical surface 375, a cavity 378 that is partially defined by the second optical surface is provided in a side of the proximal connector and filled with air. In addition, the angle of inclination of each of the optical surfaces 375 and 376 is chosen so that the incident angle at which light impinges on the surfaces is greater than the critical angle, the critical angle being the inverse sine of the ratio of the index of refraction of air or saline over the index of refraction of the plastic that forms the proximal connector. With the index of refraction of plastics ranging between about 1.4 to about 1.7, according to implementations where the optical surface is bounded on one side by air, the critical angle is greater than about 36 degrees to greater than about 46 degrees depending on the specific index of refraction of the plastic that is used in the construction of the proximal connector. According to implementations where the optical surface is bounded on one side by saline, the critical angle is greater than about 51 degrees to greater than about 72 degrees depending on the specific index of refraction of the plastic that is used in the construction of the proximal connector. Thus, according to some implementations optical surface 375 is configured to be impinged upon by the end emitted bacterial disinfecting light at an incident angle that is greater than about 36 degrees to about 46 degrees, and optical surface 376 is configured to be impinged upon by the end emitted bacterial disinfecting light at an incident angle that is greater than about 51 degrees to about 72 degrees.

With reference to FIG. 20B, the path traveled by the light emitted by the end emitting fiber is shown. Like the implementation of FIG. 14A, a gap may exist between the end of fiber 302 and the end wall of the end emitting fiber lumen 310. In any event, the end wall 362a of lumen 362 constitutes the first optical surface 374 through which the light emitted by the fiber 302 passes. The gap may be filled with an index matching gel or adhesive that has an index of refraction between that of the core of fiber 302 and that of the plastic that forms the proximal connector 304. The light path 379 between the end of the fiber 302 and its target location involves a passing of the light through the first and fourth optical surface 374 and 377 and a total internal reflection on each of optical surfaces 375 and 376 as shown in FIG. 20B. In the context of the implementation of FIGS. 20A and 20B, each of optical surfaces 374 and 377 is a refractive optical surface and each of optical surfaces 375 and 376 is a total internal reflection optical surface.

As explained above, a cavity 378 filled with air is formed in a side of the proximal connector 304. According to some implementations the cavity is open to the environment as shown in FIGS. 20A and 20B, whereas in other implementations the cavity 378 is closed to prevent any contaminates from entering the cavity after the cavity has been filled with purified air. According to some implementations closure of the cavity 378 is achieved by wrapping the outer surface of the proximal connector 304 with a heat shrink and then heat shrinking it tightly about the outer surface. According to some implementations, the heat shrink wrapping has light reflective properties that act to contain disinfecting light inside the proximal connector in a manner like that described above.

The formation of the optical surfaces internal to the proximal connector 304 can be difficult. This is because pins with ends having optical quality finishes are used in the formation of the optical surfaces during a molding process. During the molding process the end of the pins are strategically located so that the molten plastic forms over the ends of the pins. Because the end of the pins have an optical quality finish, the plastic surfaces formed by the pins will also have an optical quality finish when the plastic solidifies.

A problem associated with this method of forming the optical surfaces is that the desired location of the ends of the pins is not always easily accessible, and at times is not accessible at all. The implementation of FIGS. 21A and 21B addresses this issue with the use of an insert 380 that is manufactured separately from the proximal connector 304. As shown in the figures, the insert 380 is affixed inside a cavity 381 located in a side of the proximal connector 304. The system includes first, second, third and fourth optical surfaces 382-385, of which the first, second and third optical surfaces 382-384 are located in or on the insert 380 and total internal reflection occurs at the second and third optical surfaces 383 and 384. The end of the end emitting fiber 302 is located inside a lumen 388 of the insert 380, and according to some implementations the insert 380 is constructed of the same material that forms the proximal connector 304. The end wall of the insert lumen 388 constitutes the first optical surface 382 through which light passes toward the second optical surface 383. Optical surfaces 383 and 384 are each bounded on one side by the plastic material that forms the insert 380 and on the other side by air 386. In addition, the angle of inclination of each of the optical surfaces 383 and 384 is selected so that the incident angle at which the light impinges on these surfaces is greater than the critical angle, which in this case is the inverse sine of the ratio of the index of refraction of air over the index of refraction of the plastic that forms the insert 380.

Figure 21B:
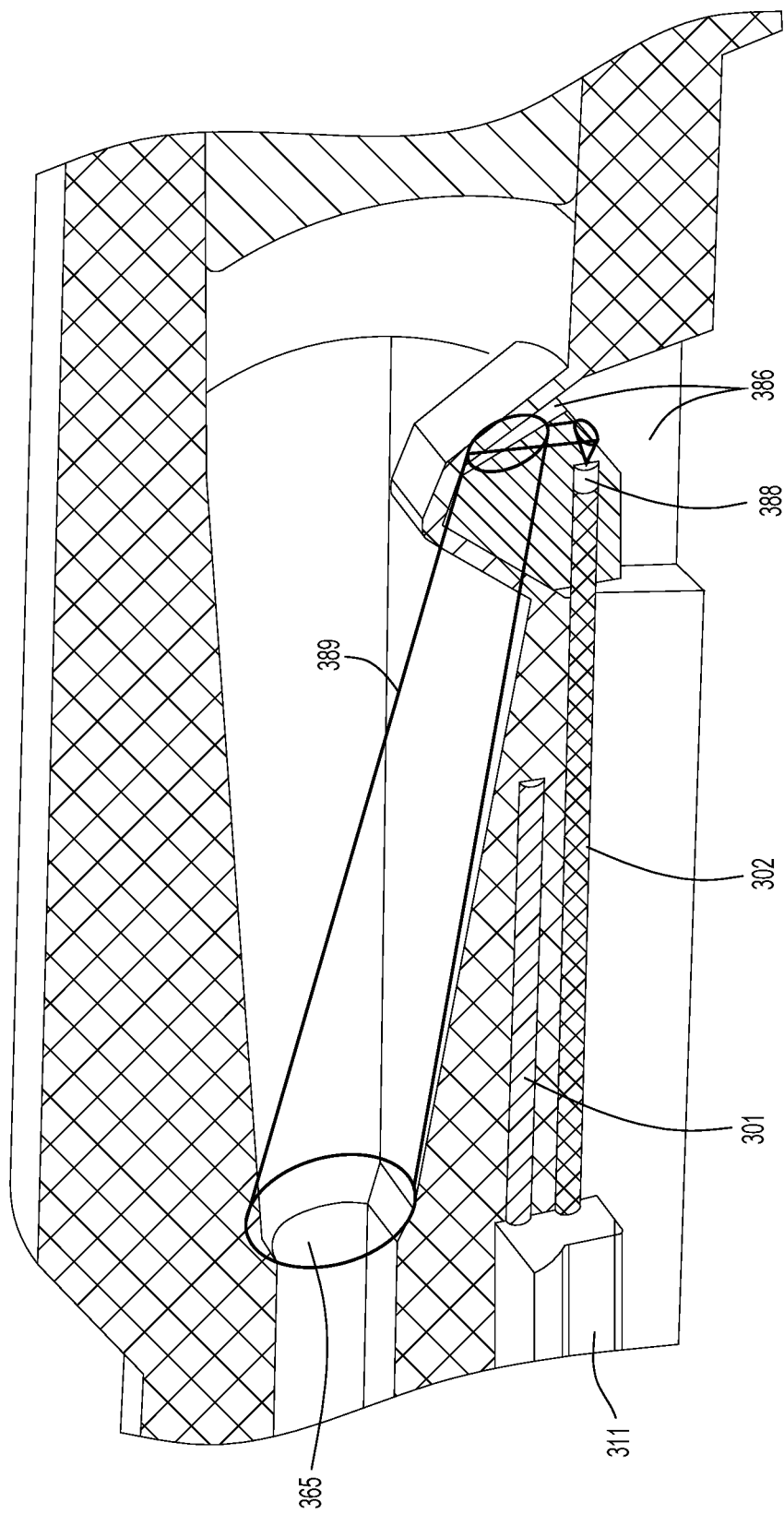
FIG. 21B illustrates a path of the light emitted by the end emitting fiber through the proximal connector of FIG. 21A.

With reference to FIG. 21B, the path 388 traveled by the light emitted by the end emitting fiber 302 is shown. Like the implementations of FIGS. 14A and 20A, a gap may or may not exist between the end of fiber 302 and the end wall of the insert lumen 388. When a gap is provided it may be filled with an index matching gel or adhesive that has an index of refraction between that of the fiber core and that of the material that forms the proximal connector 304. The light path 389 between the end of the fiber 302 and its target location involves a passing of the light through the first and fourth optical surface 382 and 385 and a total internal reflection on each of optical surfaces 383 and 384 as shown in FIG. 21B. As shown in FIGS. 21A and 21B, the insert 380 resides inside a cavity 381 formed in the side of the proximal connector 304. The shapes of the insert 380 and cavity 381 are selected so that air gaps 386 exists at the boundary of each of the second optical surface 383 and third optical surface 384. According to some implementations the cavity 381 is open to the environment as shown in FIGS. 21A and 21B, whereas in other implementations the cavity 381 is closed to prevent any contaminates from entering the cavity after the cavity has been filled with purified air.

In the context of the implementation of FIGS. 20A and 20B, each of optical surfaces 382 and 385 is a refractive optical surface and each of optical surfaces 383 and 384 is a total internal reflection optical surface.

In the exemplary implementation of FIG. 3 there exits eight optical fibers. These include the radially emitting fiber 205 and imaging fiber 207 of the main shaft 200 and also the radially emitting fibers 301 and end emitting fibers 302 associated with each of the three infusion shafts 300. As noted above, there may be fewer or more than three infusion shafts 300. In addition, according to some implementations one or more of the infusion shafts 300 may possess only one of a radially emitting fiber 301 and an end emitting fiber 302 as exemplified above in the description of FIGS. 19A and 19B. Further, according to some implementations the main shaft 200 may include only one of a disinfecting radially emitting fiber 205 and an imaging fiber 207. Moreover, one or more of the main shaft 200 and infusion shafts 300 may not be provided with any type of optical fiber. As such, it is evident that any of a variety of implementations contemplated herein may include any combination of fewer or more than eight optical fibers. With this in mind, the forthcoming description is directed to the implementation of FIG. 3.

Figure 22A:
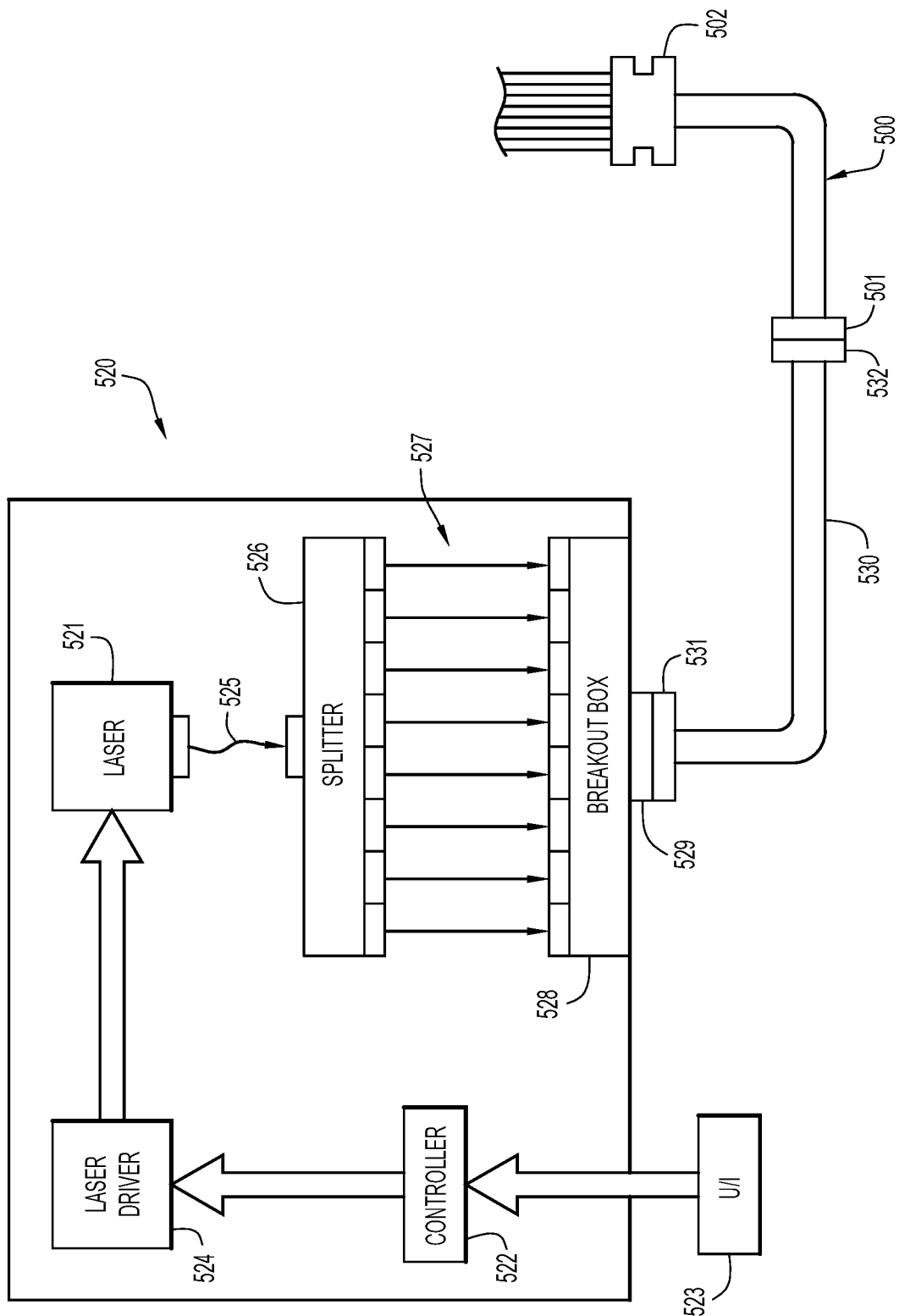
FIG. 22A illustrates a laser system that delivers light from a single laser to eight optical fibers of a central venous catheter according to one implementation.
Figure 22B:
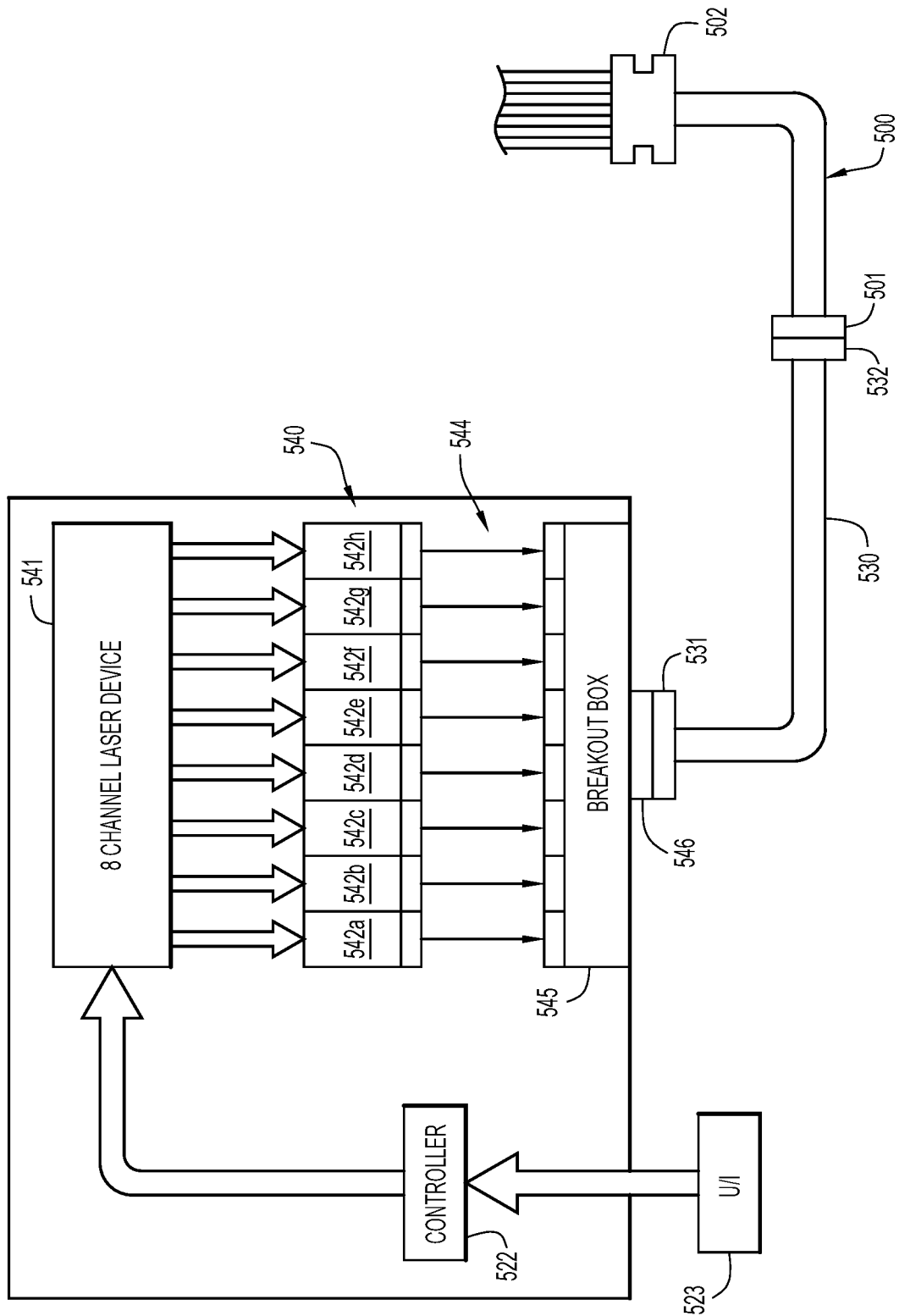
FIG. 22B illustrates a laser system that delivers light from eight lasers to a respective eight optical fibers of a central venous catheter according to one implementation.
Figure 22C:
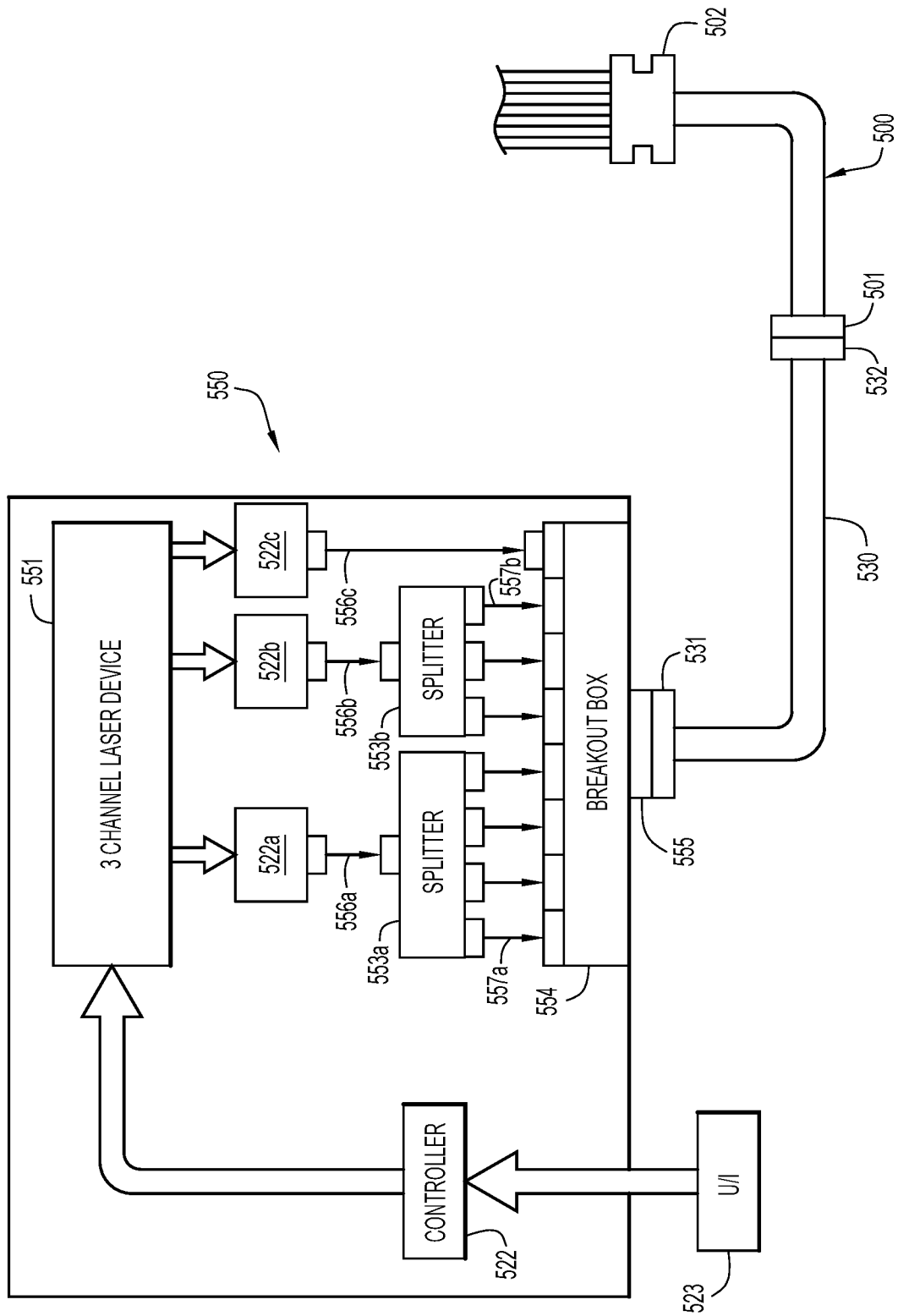
FIG. 22C illustrates a laser system that delivers light from three lasers to eight optical fibers of a central venous catheter according to one implementation.

Light may be delivered to the various optical fibers residing in the main shaft 200 and infusion shafts 300 in a number of ways. For example, the disinfecting radially emitting fibers 205 and 301 may each be optically coupled to a common first laser, the disinfecting end emitting fibers 302 may each be optically coupled to a common second laser, and the imaging fiber 207 may be optically coupled to a third laser as shown in FIG. 22C. In this manner, the type of light delivered to each of the three types of fibers may be tailored to its intended function. The types of light may be distinguished, for example, by their wavelength and optical power. However, according to some implementations all of the optical fibers may be optically coupled to a single common laser as shown in FIG. 22A, while in other implementations each optical fiber is optically coupled to its own individual laser as shown in FIG. 22B. In this latter case the type of light delivered to each of the optical fibers may be individually tailored to its intended function like that discussed above in the implementation of FIG. 22C.

In the description that follows light is routed to the optical fibers residing in the main shaft 200 and infusion shafts 300 via the CVC hub 400. However, in other implementations one or more or all of the optical fibers enter their respective lumens inside the main shaft and infusion shaft without having passed through the hub 400. An advantage of running the optical fibers through the hub 400 as shown in FIG. 3 is that, other than the umbilical cord 500, there are no other optical fibers residing outside the CVC 100 to interfere with a health care clinician's access to the various components of the CVC. As such, existing CVC clinical practices may be followed with little or no change.

Figure 23:
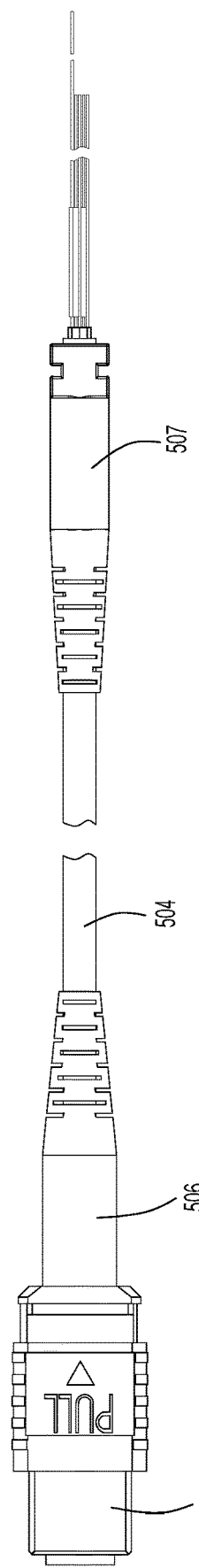
FIG. 23 shows a top view of an optical umbilical cord of a central venous catheter according to one implementation.
Figure 24B:
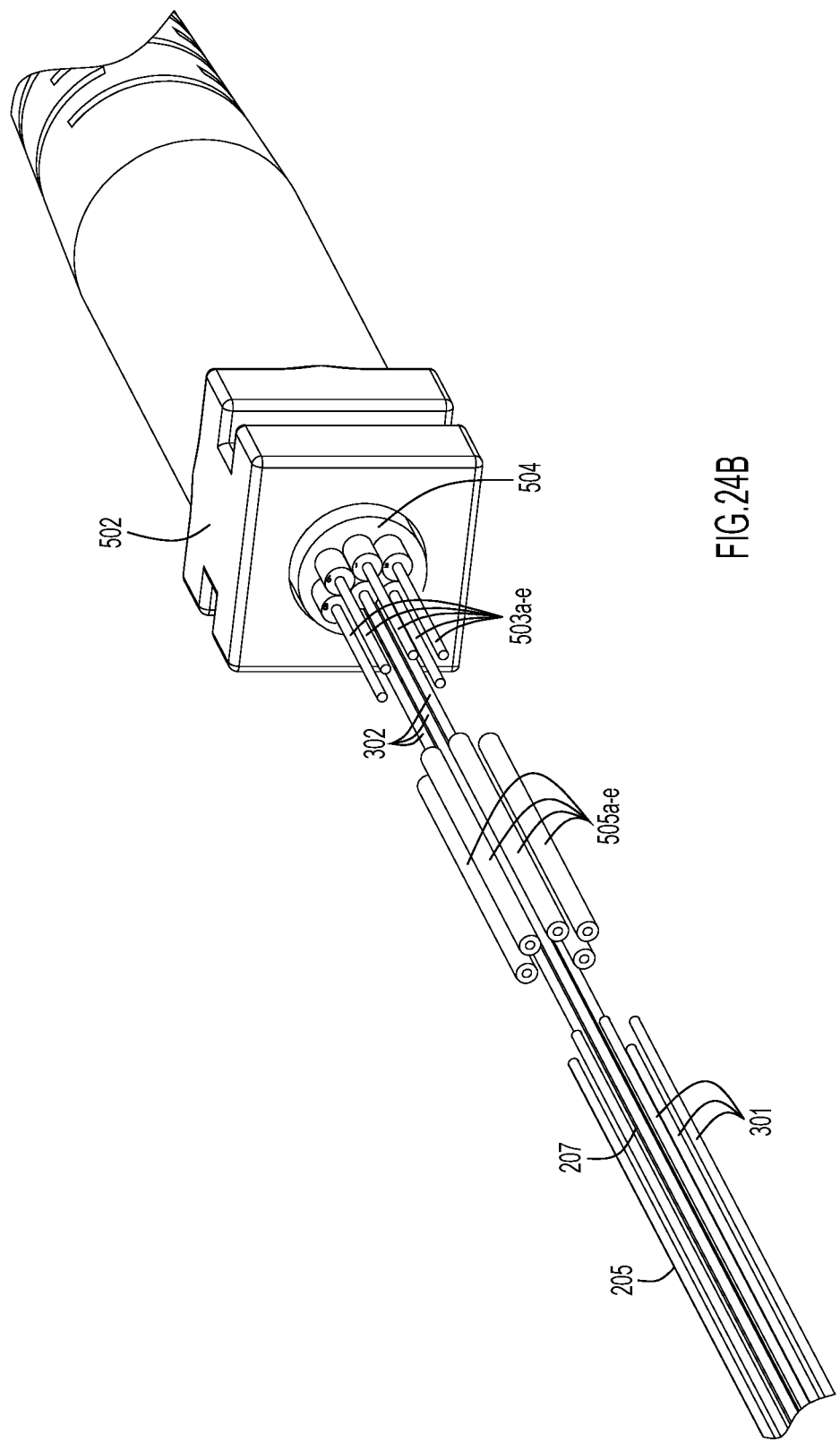
FIG. 24B is an exploded view of the component parts of the optical fibers shown in FIG. 24A.

FIG. 23 is a top view of an optical fiber umbilical cord 500 that is connectable to the hub 400 of the CVC 100. FIG. 24A is a perspective view of an end of the umbilical cord 500. FIG. 24B is an end view of the distal end of the umbilical cord. The umbilical cord 500 is configured to transport light that originates from a one or more lasers to each of the optical fibers residing in the main shaft 200 and infusion shafts 300 of the CVC 100. The umbilical cord 500 originates at a proximal optical connector 501 that has eight ports that receive and direct light to eight transport fibers 503 that run the length of the cord 500 with all but three of the transport fibers terminating at a location just distal to a hub connector 502. The hub connector 502 facilitates a physical connection of the distal end portion of the cord 500 to the hub 400 which will be discussed in more detail below. In the implementation of FIGS. 23 and 24A-B, the transport fibers 503 located inside the cord 500 comprise outer jackets and are disposed within the lumen of an elastomeric sheath. According to some implementations the fibers are located in Kevlar strength members located inside the sheath 504. The sheath 504 originates at the distal end of connector 501 and terminates at or just distal to the hub connector 502.

In the implementation of FIG. 3, five of the optical fibers that reside in the main shaft 200 and infusion shafts 300 are radially emitting fibers. These are fibers 205 and 207 of the main shaft 200 and fiber 301 in each of the three infusion shafts 300. The remaining three optical fibers are the end emitting fibers 302 residing in the three infusion shafts 300.

Distal to the hub connector 502 each of the transport fibers 503 is devoid of an outer jacket.

Five of the transport fibers 503 terminate a short distance distal to the hub connector 502 and are subsequently physically and optically coupled to respective radially emitting fibers 205 and 207 of the main shaft 200 and radially emitting fibers 301 of the three infusion shafts 300 by the use of fiber optic couplers 505. In the implementation of FIGS. 23 and 24A-B the end emitting fibers 302 of the infusion shafts 300 are contiguous with the transport fibers 503, but without the outer jacket. As will be explained in detail below, fibers 205, 207, 301 and 302 are routed to their respective lumens 204, 206, 309 and 310 inside the main shaft 200 and infusion shafts 300 via channels located in the hub 400.

As shown in the figures, according to some implementations, all or a majority of the fibers 205, 207, 301 and 302 extending from the umbilical 500 into the hub 400 are devoid of a jacket and comprise only a core/cladding in the radial emitting case and a core/cladding/buffer in the end emitting case. This arrangement significantly reduces the profile of the optical fibers and also the profile of the components into which they are incorporated.

Proximal and distal strain reliefs 506 and 507 are respectively provided at the junction of the connector 501 with sheath 504 and at the junction of the hub connector 502 with sheath 504 to guard against the transport fibers 503 from breaking inside the umbilical cord at these junctions. In conjunction with or in lieu of providing strain reliefs, the sheath 504 may be structured and/or made of a material that prevents the sheath from bending beyond a minimum bending radius of one or more of the transport fibers 503. The material may be, for example, a high durometer elastomer and/or a reinforced elastomer embedded with one or more stiffening elements (e.g. a coil, mandrel, braiding, Kevlar strength members etc.).

FIG. 22A illustrates an implementation of a laser system 520 that is configured to deliver light from a single laser 521 to the proximal optical connector 501 of the fiber optic umbilical cord 500. The system includes a controller 522 that is connected to a user interface 523. The system includes a laser driver 524 under the control of the controller 522. In response to instructions received from the controller 522, the driver 524 controls the operation of the laser 521. A user interface 523, such as a keypad or touchscreen, may be provided to communicate to the controller 522 user input instructions. The user input instructions may cause the controller 522 and driver 524 to operate the laser 521 in a user desired manner. For example, the user input instructions may be used to alter the wavelength and/or optical power of the light emitted by the laser 521. According to some implementations the power level delivered to an optical fiber is regulated to provide a dose of disinfecting light that both kills bacteria and generates an amount of heat that does not result in patient discomfort (e.g. maintaining the CVC components that contact the patient below 104° F.). According to some implementations the power level of the light delivered is maintained constant whilst the power is turned on and off to provide the desired dose of disinfecting light. According to some implementations the optical power level of the light emitted from laser 521 is sufficient to deliver a desired dose like those discussed above. Patient comfort is maintained by ensuring the maximum irradiance impingent upon the skin is less than 200 mW/cm$^2$.

Light emitted by the laser 521 is transported by an optical fiber 525 (e.g. multimode fiber) to a beam splitter 526 that splits the laser beam emitted by the laser 521 into eight separate laser beams. The eight laser beams are individually transported via optical fibers 527 (e.g. multimode fibers) to a breakout box 528 that is configured to direct each of the eight laser beams into eight separate ports of an optical connector 529. The optical connector 529 is in turn connected to a proximal connector 531 of an eight channel patch cord 530 that possesses eight transport fibers (e.g. multimode fibers). The transport fibers of the patch cord 530 deliver the eight laser beams to the proximal optical connector 501 of the fiber optic umbilical cord 500 via a distal connector 532.

According to some implementations the optical power of each of the laser beams transported by optical fibers 527 is sufficient to deliver a desired dose like those discussed above. In instances when light is to be delivered to both radially emitting fibers and end emitting fibers, each of the radially emitting fibers receive a larger proportion of the optical power than each of the end emitting fibers.

According to some implementations two or more lasers (e.g. three lasers) may be combined to generate a common laser beam that passes through optical fiber 525.

According to each of the laser systems disclosed herein, when light is to be delivered to an imaging fiber, the laser system may possess a separate laser dedicated to delivering light only to the imaging fiber as in laser system 550 of FIG. 22C.

FIG. 22B illustrates an implementation of a laser system 540 that is configured to deliver light from eight individual lasers 542a-h to the proximal optical connector 501 of the fiber optic umbilical cord 500. The system includes a controller 522 that is connected to a user interface 523. The system includes an eight channel laser driver 541 that is under the control of the controller 522. In response to instructions received from the controller 522 the eight channel driver 541 individually controls the operation of the lasers 542a-h. A user interface 523, such as a keypad or touchscreen, may be provided to communicate to the controller 522 user input instructions. The user input instructions may cause the controller 522 and eight channel driver 541 to operate the laser 521 in a user desired manner. For example, the user input instructions may be used to separately alter the wavelength and/or optical power of the light emitted by the lasers 542a-h, or to turn the lasers on and off. The ability to separately control the lasers allows them to be activated at different times and/or with different power levels in a way that optimizes the efficacy of the disinfecting process and/or control the amount of heat generated in the CVC to prevent patient discomfort. To this end, different parts of the CVC may be disinfected at different times and/or at different power levels. According to some implementations the delivery of disinfecting light to an optical fiber is triggered by an event. For example, one or more components of the CVC may be equipped with a motion or temperature sensor that detects when a part of the CVC has been moved or touched. According to such implementations the sensor may communicate with the controller 522 to cause one or more of the lasers to be activated upon the occurrence of an event.

Light emitted by the lasers 542a-h is transported by optical fibers 544 (e.g. multimode fibers) to a breakout box 545 that is configured to direct each of the eight laser beams into eight separate ports of an optical connector 546. The optical connector 546 is in turn connected to a proximal connector 531 of an eight channel patch cord 530 that possesses eight transport fibers (e.g. multimode fibers). The transport fibers of the patch cord 530 deliver the eight laser beams to the proximal optical connector 501 of the fiber optic umbilical cord 500 via a distal connector 532.

FIG. 22C illustrates an implementation of a laser system 550 that is configured to deliver light from three lasers 552a-c to the proximal optical connector 501 of the fiber optic umbilical cord 500. The system includes a controller 522 that is connected to a user interface 523. The system includes a three channel laser driver 551 under the control of the controller 522. In response to instructions received from the controller 522 the driver 551 controls the operation of the three lasers 552a-c. A user interface 523, such as a keypad or touchscreen, may be provided to communicate to the controller 522 user input instructions. The user input instructions may cause the controller 522 and driver 551 to individually operate the lasers 552a-c in a user desired manner. For example, the user input instructions may be used to individually alter the wavelength and/or optical power of the light emitted by each of the lasers 552a-c, or to turn the lasers on and off. As stated above, the ability to separately control the lasers allows them to be activated at different times and/or with different power levels in a way that optimizes the efficacy of the disinfecting process and/or control the amount of heat generated in the CVC to prevent patient discomfort.

Light emitted by the laser 552a is transported by an optical fiber 556a (e.g. multimode fiber) to a beam splitter 553a that splits the laser beam emitted by the laser 552a into four separate laser beams to be associated with the disinfecting radially emitting fiber 205 of the main shaft 200 and the disinfecting radially emitting fibers 301 of the three infusion shafts 300. The four laser beams are individually transported via optical fibers 557a (e.g. multimode fibers) to a breakout box 554 that is configured to direct each of the four laser beams into four separate ports of an optical connector 555. Light emitted by the laser 552b is transported by an optical fiber 556b (e.g. multimode fiber) to a beam splitter 553b that splits the laser beam emitted by the laser 552b into three separate laser beams to be associated with the disinfecting end emitting fibers 302 of the three infusion shafts 300. The three laser beams are individually transported via optical fibers 557b (e.g. multimode fibers) to a breakout box 554 that is configured to direct each of the three laser beams into three separate ports of the optical connector 555. Light emitted by laser 552c, that is to be associated with the imaging fiber 207 of the main shaft 200, is transported by an optical fiber 556c (e.g. a multimode fiber) directly to the breakout box 554 which is configured to direct the laser beam into a port of the optical connector 555. The optical connector 555 is in turn connected to a proximal connector 531 of an eight channel patch cord 530 that possesses eight transport fibers (e.g. multimode fibers). The transport fibers of the patch cord 530 deliver the eight laser beams to the proximal optical connector 501 of the fiber optic umbilical cord 500 via a distal connector 532.

According to some implementations each of lasers 522a and 522b comprise blue lasers and laser 552c is a red laser.

Figure 25:
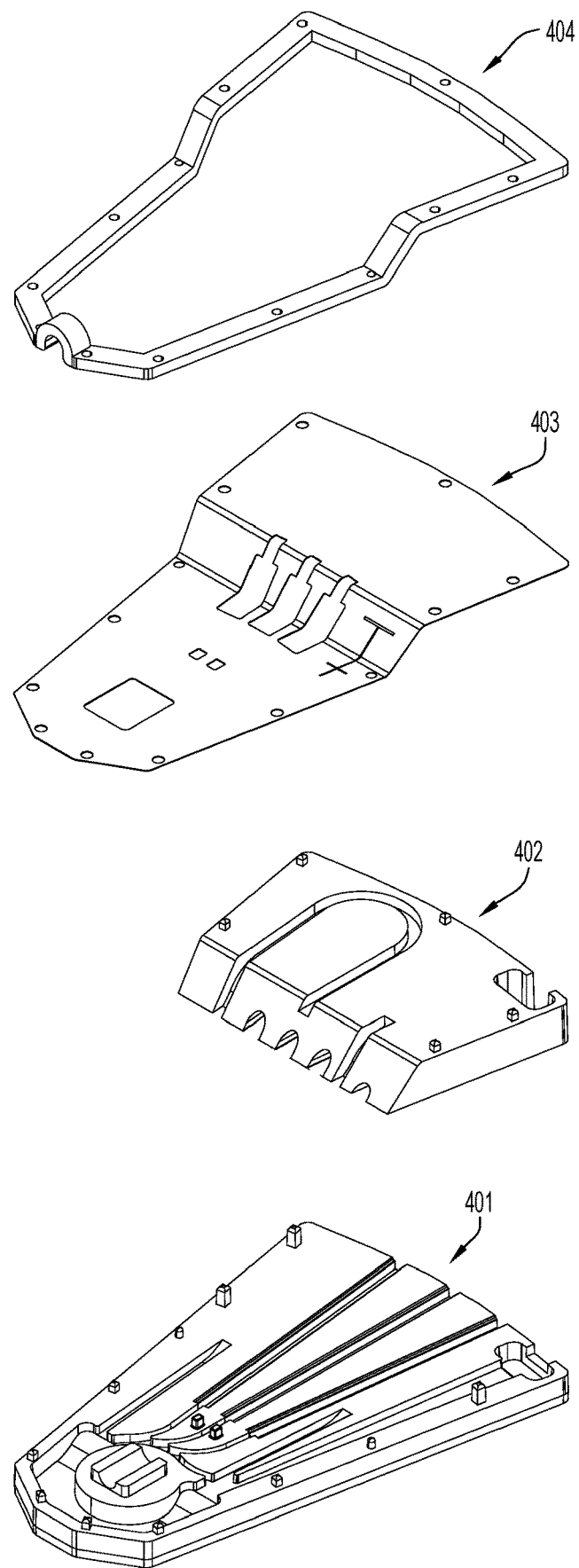
FIG. 25 show top perspective views of the components of a hub according to one implementation, the components including a bottom tray, a mid-tray, a cover and a gasket.

FIG. 25 shows a top perspective view of the various parts that from the hub 400 according to one implementation. The parts include a bottom tray 401, a mid-tray 402, a cover 403 and a top gasket 404, of which enlarged perspective views are respectively provided in FIGS. 26-29. The bottom tray 401 and mid-tray 402 include features for supporting the proximal end of the main shaft 200 and the distal ends of the infusion shafts 300 relative to one so that the working lumens 308 of the infusion shafts and the working lumens 201a-c of the main shaft may be connected with the use of conduits located inside the hub 400. The bottom tray 401 and mid-tray 402 also include features that define one or more channels for strategically routing the optical fibers through the hub 400 in a manner that protects the optical fibers against breakage. The channels that possess the radially emitting fibers may also run above, below or to the side of the conduits inside the hub that join the working lumens 308 of each of the infusion shafts 300 to the working lumens 201a, 201b and 201c of the main shaft 200. The fiber channels may be formed by any of a variety of structures including, but not limited to, continuous wall segments, spaced-apart posts, etc. In channels that have one or more bends along their length, to protect against breakage of the optical fibers, the bends are constructed to prevent a bending of the optical fiber housed therein beyond its minimum bending radius. For example, each of the one or more bends may have a radius of curvature that is equal to or greater than the minimum bending radius of the optical fiber.

Figure 26:
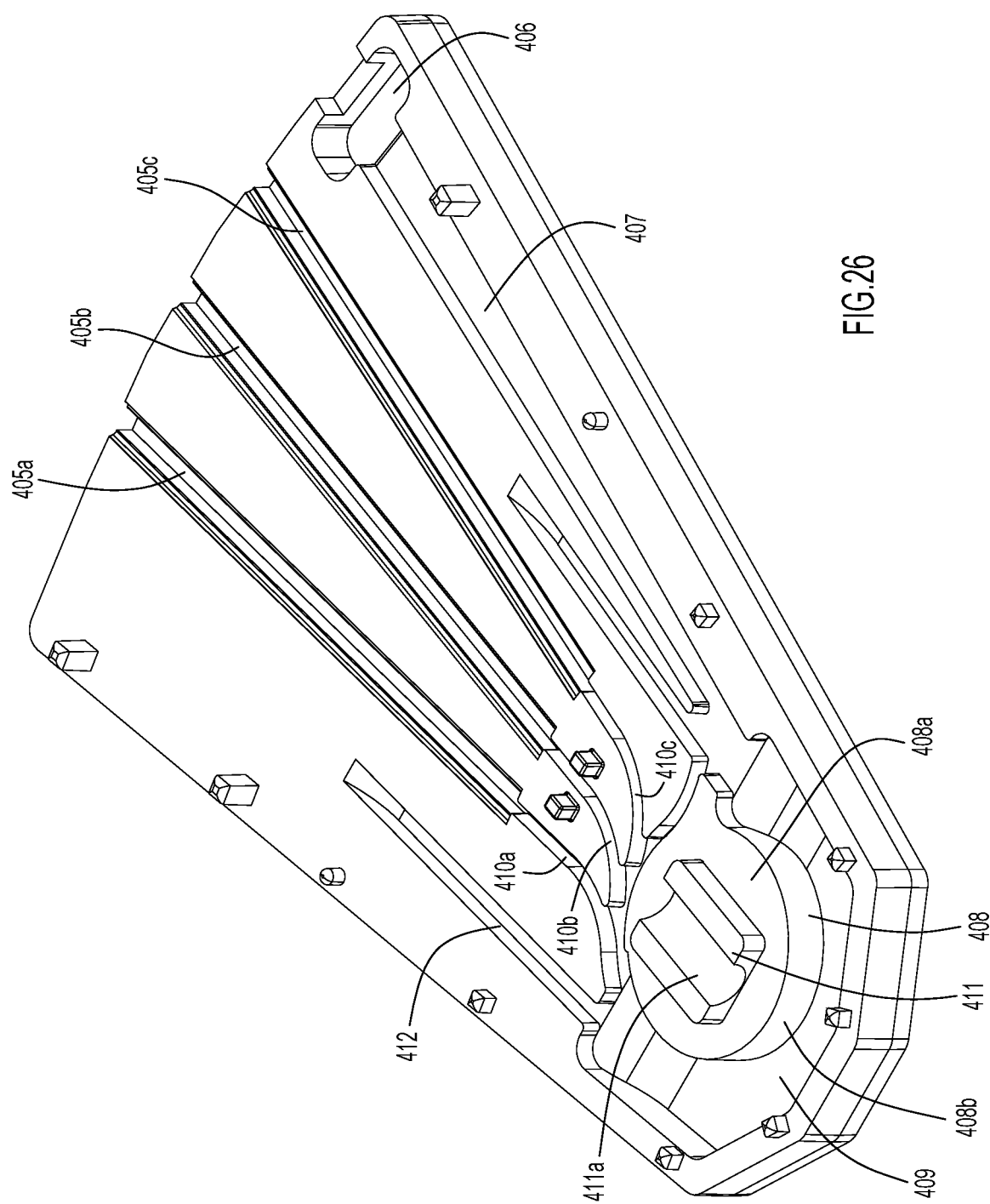
FIG. 26 is an enlarged view of the bottom tray of FIG. 25.

As shown in FIG. 26, according to some implementations the bottom tray 401 has a plurality of channels formed therein. Each of channels 405a-c is configured to hold one of the infusion shafts 300. The depth and width dimensions of the channels 405a-c may respectively correspond to the length and width dimensions of the infusion shaft key portions 311. A receptacle 406 in the bottom tray 401 is configured to accept the hub connector 502 of the optical fiber umbilical 500 in a manner that locks the proximal connector onto the bottom tray. Distal to the receptacle 406 is an elongate channel 407 that guides the optical fibers that emanate from the umbilical 500 into the hub 400. Distal to channel 407 there resides a raised platform 408 that includes a top surface 408a and a curved wall portion 408b. (It is important to note that the top surface 408a need not be a planar/level surface) A channel 409, which is at least partially formed by the curved wall portion 408b of the raised platform 408, communicates fiber channel 407 to fiber channels 410a-c. Each of fiber channels 410a-c is respectively located distal to channels 405a-c and assists in guiding the radially emitting fiber 301 and/or end emitting fiber 302 into their respective lumens 309 and 310 inside the key portions 311 of the infusion shafts 300.

FIG. 30 illustrates a perspective view of a partially assembled hub according to one implementation with the mid-tray 402 being attached to the bottom tray 401. A distal end 390a-c of each of the infusion shafts 300 extends distally from the mid-tray 402. In the implementation of FIG. 30 there exist eight optical fibers consistent with the embodiment of FIG. 3 described above. According to the implementation of FIG. 30 all of the fibers 205, 207, 301 and 302 extend through fiber channels 407 and 409 before they branch apart. Six of the fibers (that is fibers 301 and 302 for each of the three infusion shafts 300) pass to the infusion shafts 300 via fiber channels 410a-c while two of the fibers (that is fibers 205 and 207 of the main shaft 200) pass to the main shaft 200 via a fiber channels 412 and 413. As shown in FIG. 30, the various fiber channels may be disposed at different elevations within the hub 400. This provides greater flexibility in laying out the optical fiber pathways.

Figure 27A:
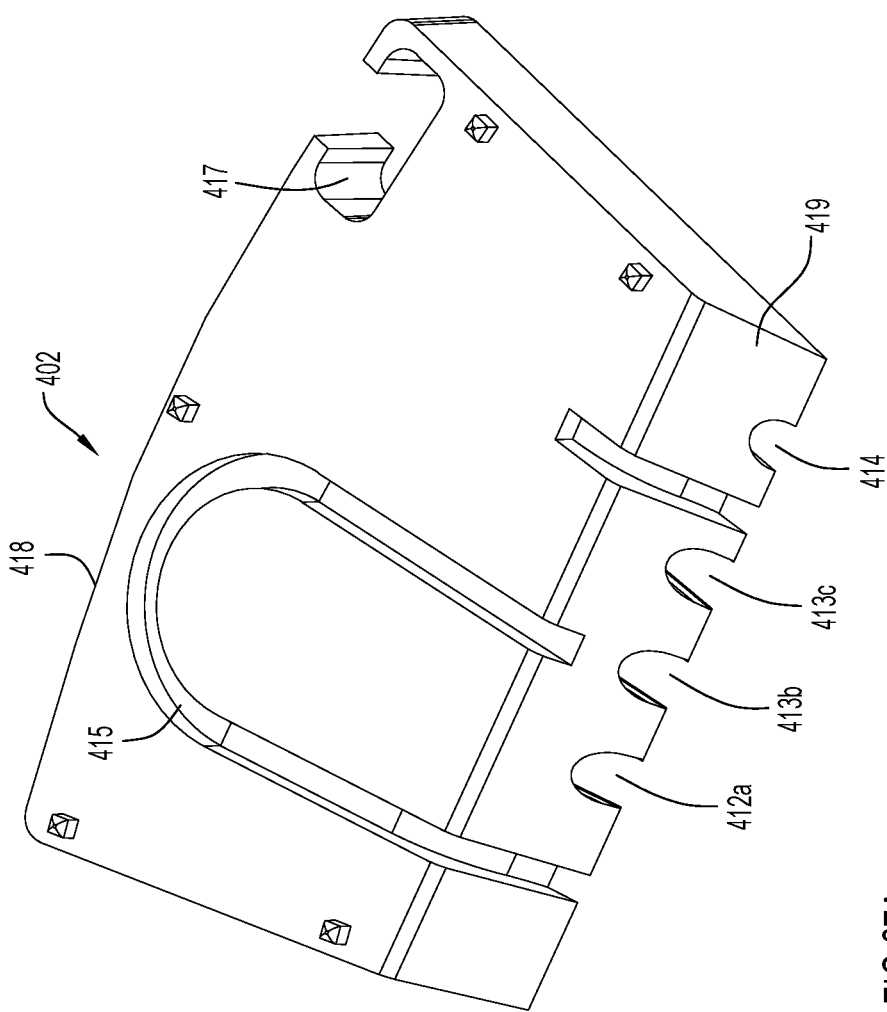

FIGS. 27A and 27B respectively show top and bottom perspective views of the mid-tray 402 according to one implementation. The mid-tray includes grooves 413a-c and 414 that each extend between its proximal and distal ends 418 and 419, respectively. As shown in FIG. 30, when the infusion shafts 300 are assembled on the bottom tray 401 and in the mid-tray 402 the distal end portion 390a-c of each of the infusion shafts protrudes distal to the distal side 419 of the mid-tray. According to some implementations the portions of the tubular body 303 of each of the infusion shafts that form the working lumens 308 (e.g. semi-circular region of the infusion shaft) fit tightly within their respective grooves 413a-c. In some instances the fit between the infusion shafts 300 and the grooves 413a-c produces a liquid-tight seal at their interface along at least a portion of the length of the grooves 413a-c. According to some implementations the mid-tray 402 also includes a receptacle 417 that houses at least a portion of the hub connector 502 of the optical fiber umbilical 500.

During an assembly of the hub 400 a portion of the main shaft 200 may be supported on a cradle 411 positioned atop the raised platform 408. According to some implementations the cradle 411 has a grooved external surface 411a that conforms to the external surface of the main shaft. When positioned on the cradle 411, as shown in FIG. 30, the elongate proximal end portion 220 of the main shaft 200 extends into the curved channel 413 of the mid-tray 402 where fibers 205 and 207 enter the proximal end 221 of the elongate proximal end portion 220.

Assembly of the CVC 100 may occur in any of a variety of steps to which the following assembly method represents only but one example. At step one the hub connector 502 of the fiber optic umbilical cord 500 is fixed inside the receptacle 406 of the bottom tray 401. The radially emitting fibers 301 and end emitting fibers 302 associated with the infusion shafts 300 are then placed inside the lumens 309 and 310 of their respective infusion shafts. This step may include fixing the distal end of the end emitting fibers 302 inside the proximal connectors 304 of the infusion shafts 300 with, for example, an index matching adhesive as discussed above. With the fibers 301 and 302 properly positioned inside their respective lumens inside the infusion shafts 300, the distal end portion of each of the infusion shafts is positioned on the bottom tray 401. According to some implementations this includes aligning each of the distal end portions of infusion shafts with channels 405a-c in the bottom tray 401 with each of their key portions 311 respectively residing in one of said channels. The key portions 311 may be pressed-fit into the channels 405a-c and/or secured inside said channels with the use of an adhesive.

With the proximal end portions of the infusion shafts 300 in place on the bottom tray 401 the six fibers 301 and 302 are routed through the bottom tray fiber channels 407, 409 and 410a-c.

With the infusion shafts 300 and fibers 301 and 302 in place, the mid-tray 402 is positioned over and attached to a proximal end portion of the bottom tray 401. When the mid-tray 402 is attached to the bottom tray 401 the distal end portions of the infusion shafts reside inside their respective grooves 413a-c inside the mid-tray 402 as depicted in FIG. 30. After the mid-tray 402 is positioned on the bottom tray 401, the radially emitting fiber 205 and imaging fiber 207 are routed through fiber channels 407, 409, 412 and 413 and into their respective lumens 204 and 206 in the main shaft 200.

As discussed above, according to some implementations one or more or all of the curves of the structures that form the fiber channels (e.g. channels 407, 409, 410a-c and 413) are endowed with a radius of curvature that is no less than the minimum bending radius of one or more of the fibers that pass through them.

Figure 31:
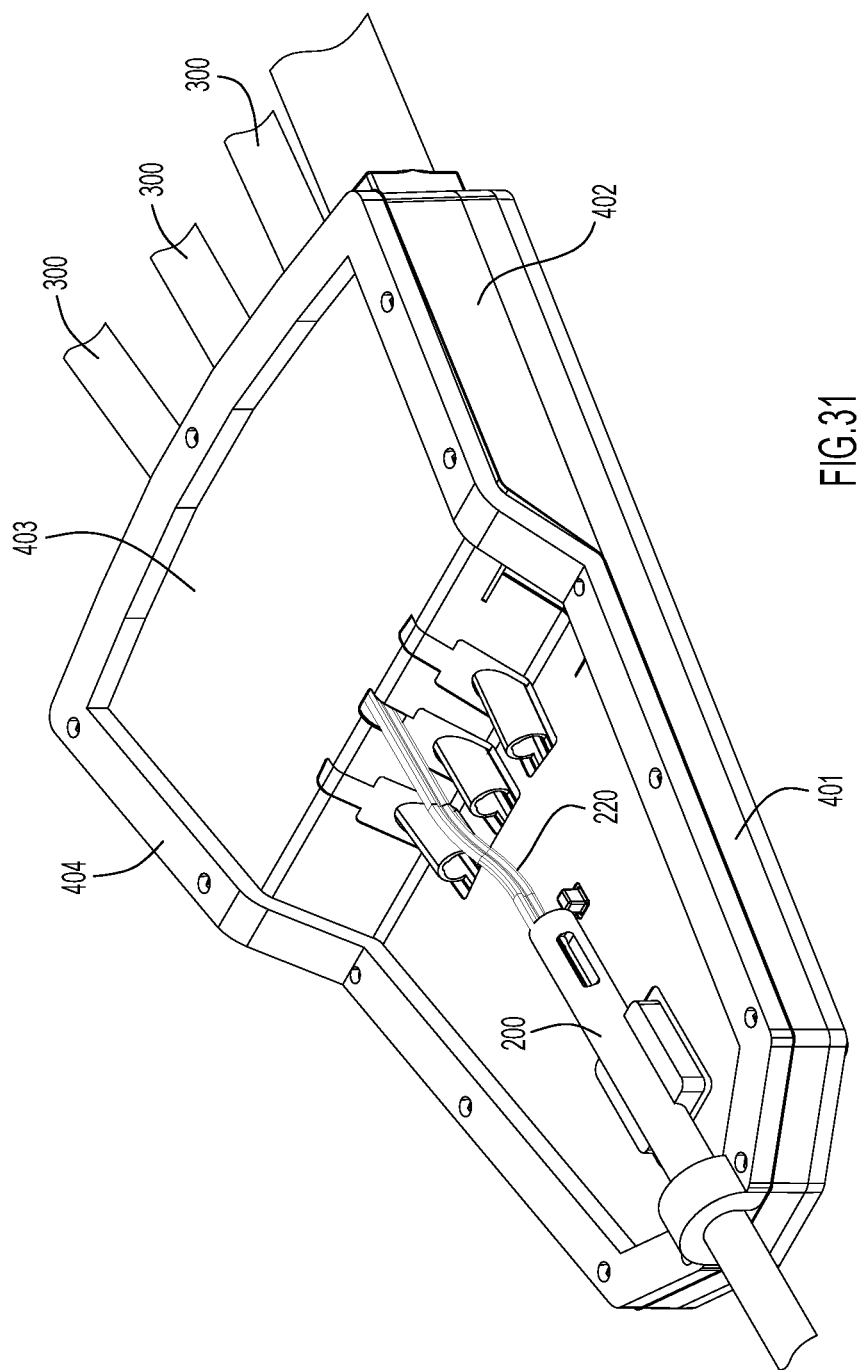
FIG. 31 is a perspective view of the hub of FIG. 30 with a cover positioned to protect the optical fibers running through the hub.

Because a later step involves a casting of a urethane or other polymeric material to encapsulate the hub, with the infusion shafts and optical fibers in place the cover 403 is situated to reside above the fiber channels 407, 409, 410a-c, 412 and 415 formed in the bottom tray 401 and mid-tray 402 as shown in FIG. 31. The cover 403 serves to isolate the optical fibers from the casting material so that the optical fibers maintain a freedom of movement inside the hub when the casting is complete. The cover 403 includes an opening 441 through which the cradle 411 of the bottom tray protrudes. The cover 403 also includes opening 442a-c through which the distal ends 390a-c of the infusion shafts 300 respectively protrude.

With the cover 403 in place to protect the optical fibers as shown in FIG. 31, the main shaft 200 is positioned on the cradle 411 atop the raised platform 408 with at least a portion of the length of its elongate proximal end portion 220 placed inside the fiber channel 413. According to some implementations the main shaft 200 is positioned on the cradle 411 so that the proximal opening of the working lumen 201a resides proximal to the raised platform 408 as shown in FIG. 30. Positioning the proximal end of the working lumen 201a of the main shaft proximal to the raised platform 408 advantageously shortens the path taken to couple the working lumens 308 of the infusion shafts to the infusion shafts 201a-c of the main shaft 200. This positioning also facilitates a routing of at least a portion of the length of the conduits that interconnect the infusion shafts to the main shaft above the fiber channels 410a-c so that these lengths of the conduits may be irradiated with bacterial disinfecting light emitted by the radially emitting fibers 301 that reside in fiber channels 410a-c.

As shown in FIG. 30, one or more or all of the fibers 205, 207, 301 and 302 is routed in the hub 400 so as not to be taut along at least a portion of the structures that form the fiber channels located in the bottom tray 401. This provision of slack in the one or more optical fibers inside the hub guards against excessive tensile forces being applied to the fibers when the main shaft 200 and infusion shafts 300 are bent or pulled in tension as a result of the slack being taken up inside the hub when the shafts are bent. This is particularly important where at least a portion of the optical fiber is longitudinally fixed inside the main shaft or infusion shaft, like with certain implementations of the imaging shaft 205 and end emitting fibers 302 discussed above.

With the cover 403 in place, the top gasket 404 is placed atop the periphery of the cover 403 to hold the cover in place prior to the casting step. The gasket 404 includes at its distal end a groove 445 through which the main shaft 200 passes. As shown in FIGS. 25-31, holes and posts located about the periphery of the bottom tray 401, mid-tray 402, cover 403 and top gasket 404 facilitate an aligning and coupling of the components prior to the casting step.

Figure 32:
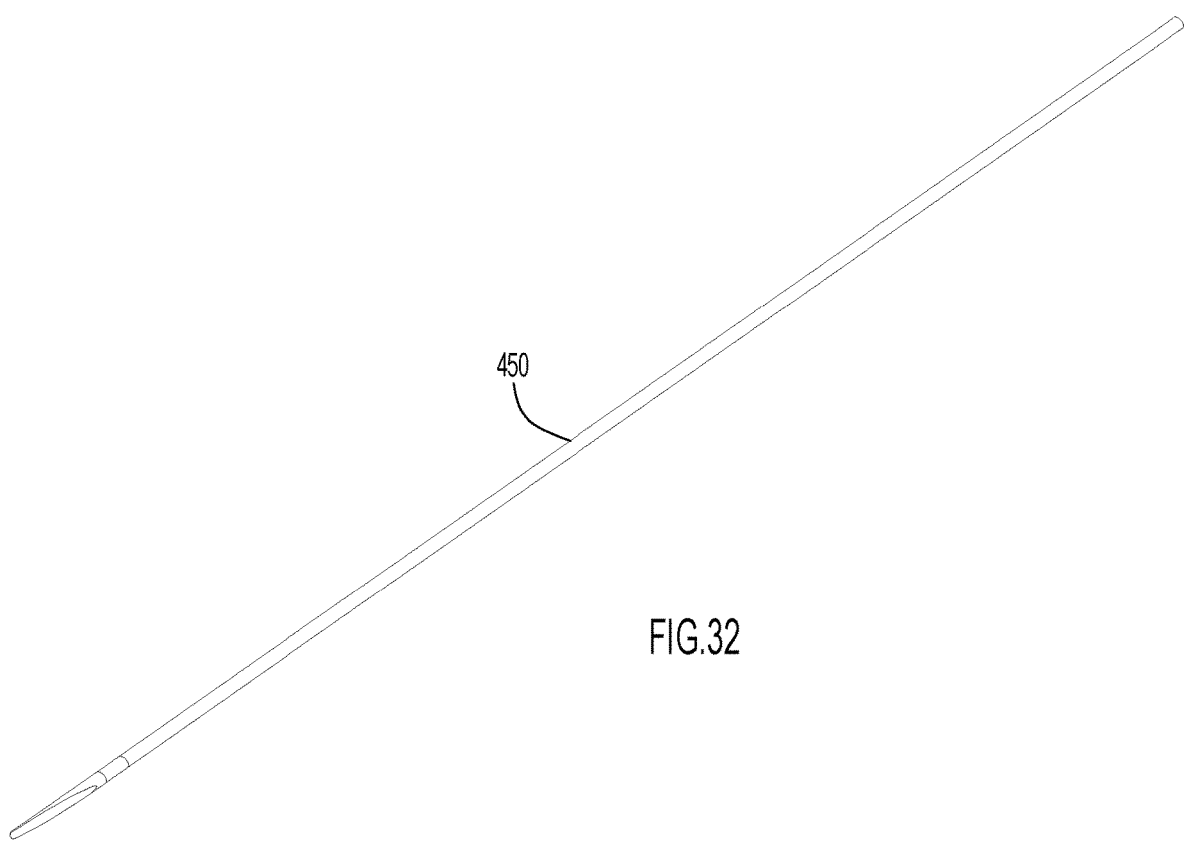
FIG. 32 shows an elongate beading used to form a conduit within the hub.

As discussed above, conduits are used to fluidly connect the working lumens 308 of the infusion shafts to the respective working lumens 201*a-c* of the main shaft 200. According to some implementations the conduits are formed during the casting process mentioned above. According to such implementations when the hub is in a partially assembled state as shown in FIG. 31, an elongate flexible beading/ mandrel 450 (see FIG. 32) is inserted through each of the working lumens 308 of the infusion shafts 300 and into the respective working lumens 201*a-c* of the main shaft 200. With the beadings in place the entirety of the assembly is cast with a polymeric material, such as a urethane. The casting is performed so that the casting material totally encapsulates those portions of the beadings 250 that extend between the distal end of the infusion shafts and proximal end of the main shaft. Upon the casting material having cured, the beadings 450 are removed so that flow channels encapsulated inside the casting exist between the working lumens of the infusion shafts 300 and main shaft 200. FIG. 3 shows the external surface of the hub 400 when the casting step is complete.

Figure 33:
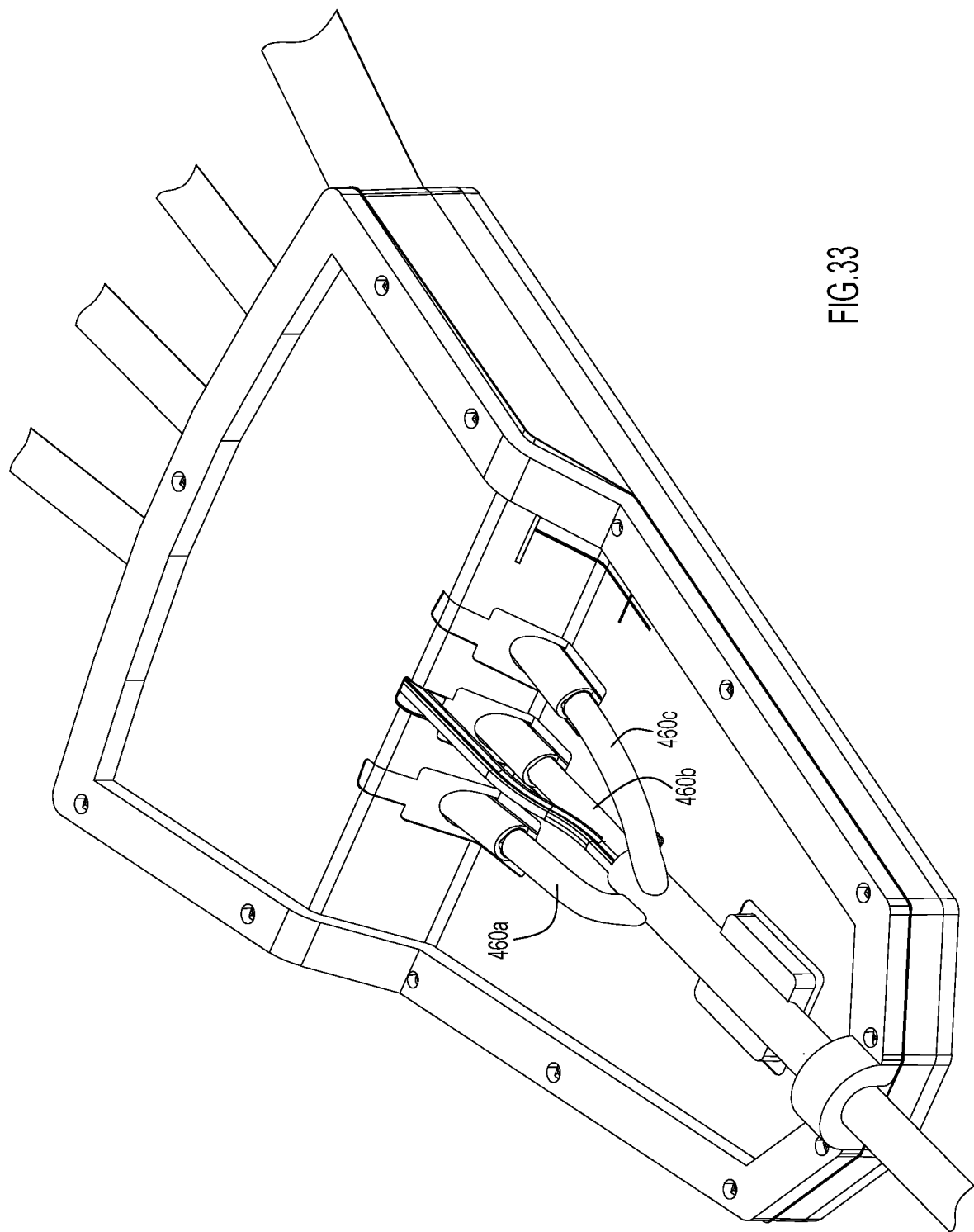
FIG. 33 is a perspective view of a partially assembled hub according to another implementation.

According to other implementations, as shown in FIG. 33, the conduits 460*a-c* that connect the working lumens of the infusion shafts and main shaft are not cast, but are instead physically and fluidly coupled to their respective working lumens before the casting step. According to such implementations the conduits 460*a-c* may be fluidly sealed to the working lumens of the infusion shafts and main shaft prior to the casting process. According to other implementations the interfaces between the conduits 460*a-c* and the working lumens of the infusion shafts and main shaft are sealed with the casting material during the casting process.

According to some implementations the casting material and the cover 403 of the hub 400 each comprises a material that is transparent or translucent to the light emitted by the disinfecting radially emitting fibers 205 and 301. According to other implementations the casting material, mid-tray 402 and cover 403 of the hub 400 each comprises a material that is transparent or translucent to the light emitted by the disinfecting radially emitting fibers 205 and 301. According to yet other implementations the casting material, bottom tray 401, mid-tray 402 and cover 403 of the hub 400 each comprises a material that is transparent or translucent to the light emitted by the disinfecting radially emitting fibers 205 and 301. By virtue of their transparency or translucence, these components of the hub enable light emitted by the light disinfecting radially emitting fibers to disinfect not only the infusion shaft 300 and main shaft 200 lumens, but to also internally flood the hub with bacterial disinfecting light to also effectuate a disinfecting of the hub itself, including its outer surfaces.

Figure 34:
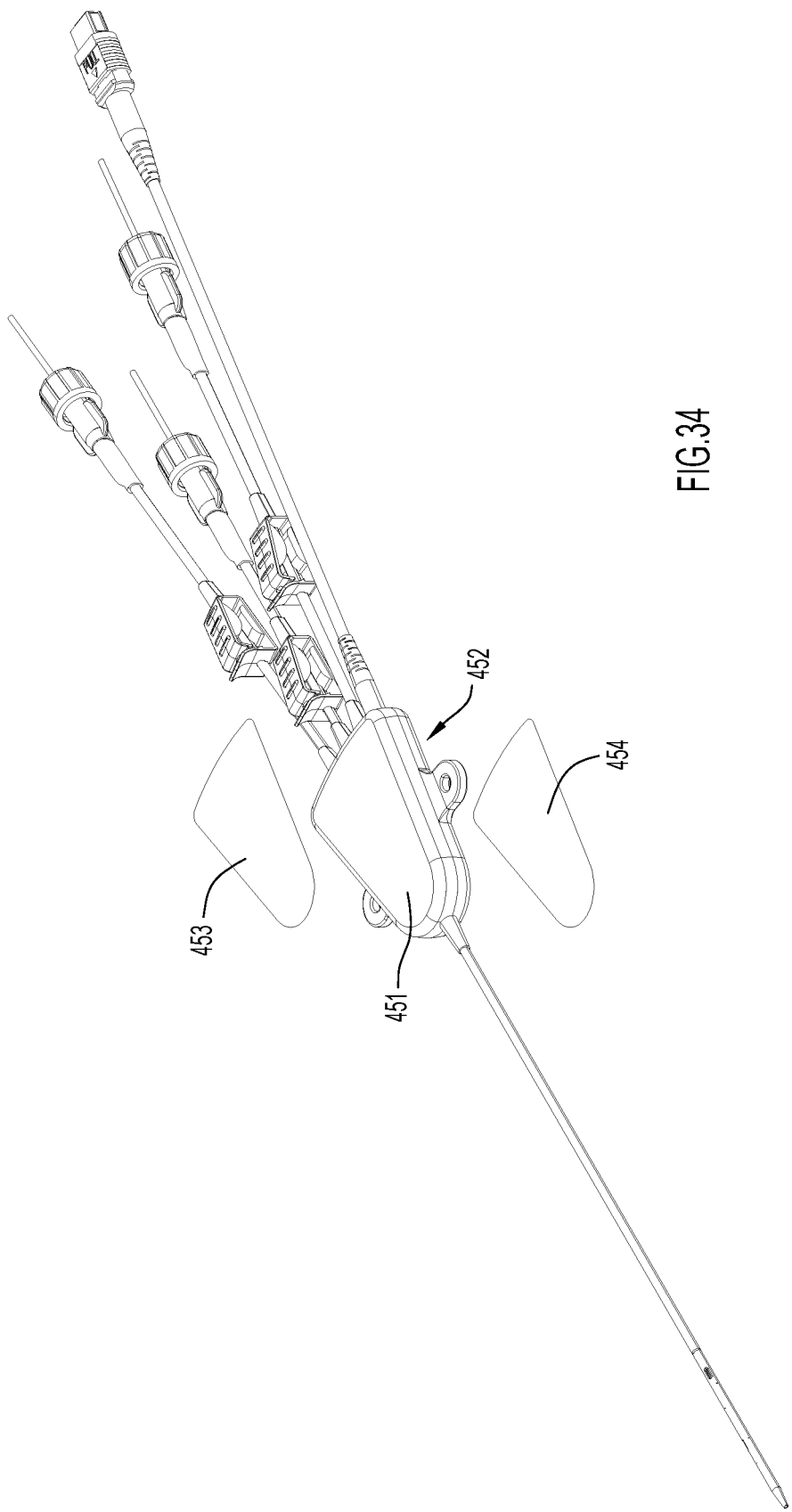
FIG. 34 is a perspective view of a central venous catheter with the hub containing one or more light reflectors on its outer surface.

As shown in FIG. 34, according to some implementations light reflectors 453 and 454 may be affixed to the top and bottom surfaces 451 and 452 of the hub 400 in order to minimize the loss of disinfecting light out of the hub. A trapping of the bacterial disinfecting light inside the hub enhances the light exposure on the internal components of the hub. This increases the bacteria killing effectiveness of the disinfecting light emitted into the hub. It also reduces the amount of time and/or the power needed to effectuate a disinfecting of the hub. According to other implementations, the casting material used to cast the hub may be impregnated with light reflecting elements that act to direct light into the hub. According to other implementations the casted hub 400 is wrapped with a material that has an internal light reflective surface. According to one implementation the material comprises shrink wrap that is shrunk about the external surfaces of the hub. According to yet other implementations, one or more of the fiber channels located in the bottom tray 401 have surfaces that are coated with a light reflective material, such as, for example, a light reflective paint.

According to some implementations disinfecting light is delivered into the CVC only by way of use of end emitting fibers. Thus, unlike the implementation of FIG. 30, each of the infusion shafts 300 and main shaft 200 of the implementation of FIGS. 35A-38 is devoid of a radially emitting fiber and a radially emitting fiber lumen.

In the implementation of FIGS. 35A-38 the disinfecting light is delivered into each of the infusion shafts 300 at two locations. The first location is in the proximal connector 304 of the infusion shaft 300 in which disinfecting light is delivered in a manner consistent with what has been described above with one or more optical surfaces and/or one or more light reflectors of the proximal connector being used to disperse disinfecting light emitted from an end emitting fiber 302 into at least a portion of the infusion shaft 300. The second location is inside the working lumen 308 of the infusion shaft 300 near its distal end. This second location is located inside the hub 400.

Although not shown in the figures, the CVC of FIGS. 35A-38 may also include an imaging fiber 207 that runs along a length of the main shaft 200 as previously described.

Figure 35A:
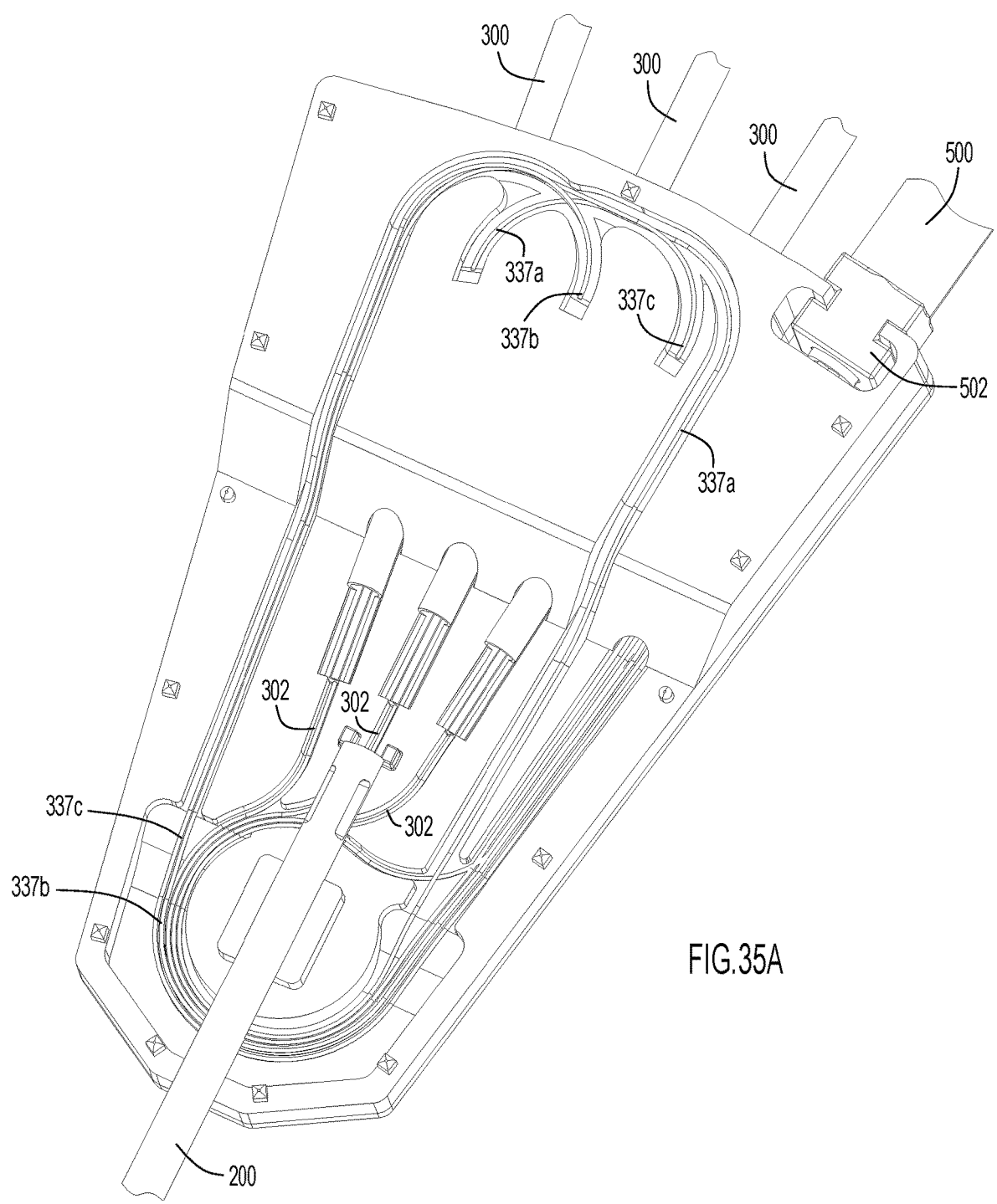
FIG. 35A is a top perspective view of a partially assembled hub according to one implementation.
Figure 36:
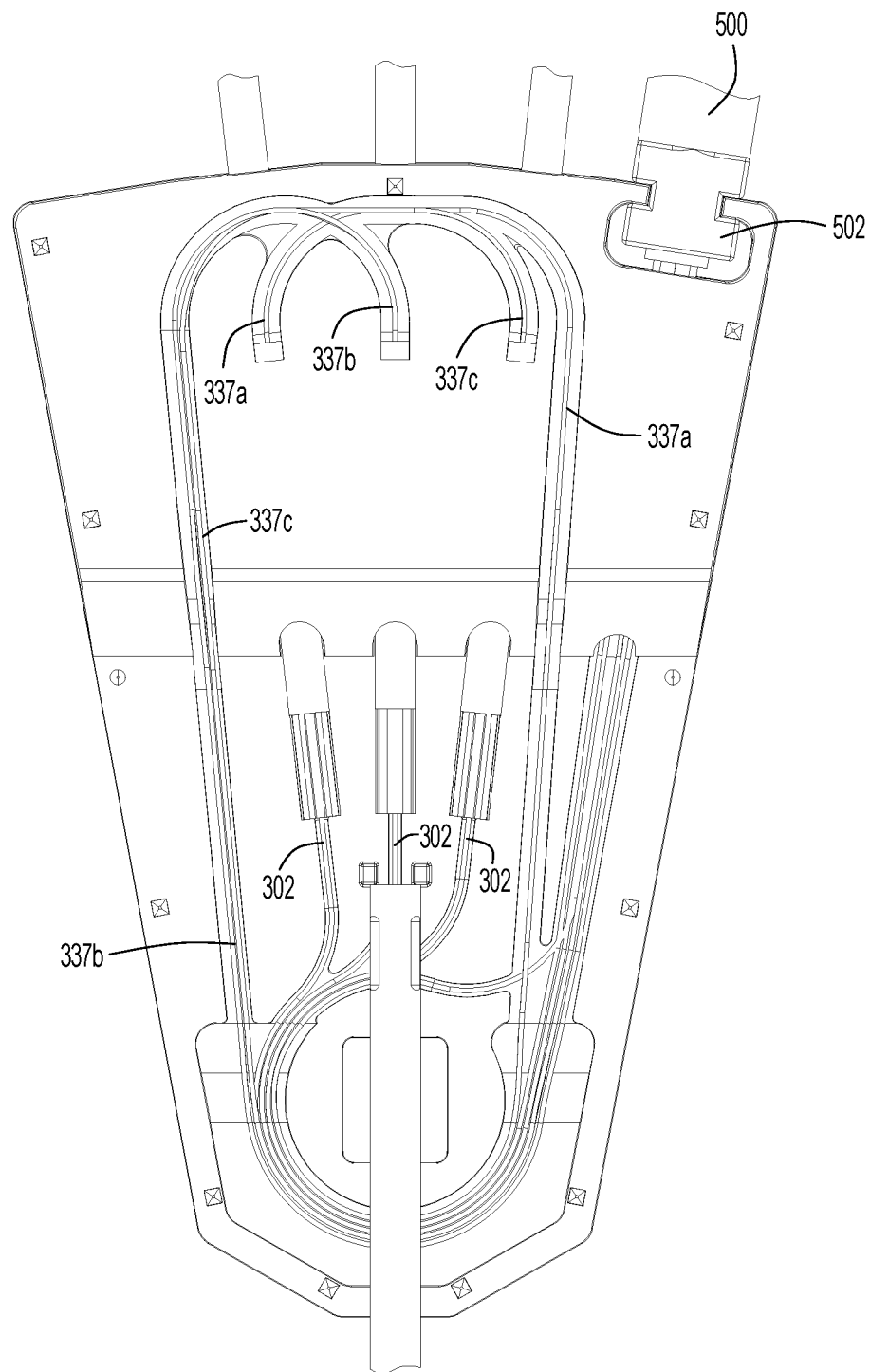
FIG. 36 is a top view of the hub shown in FIG. 35A.
Figure 37:
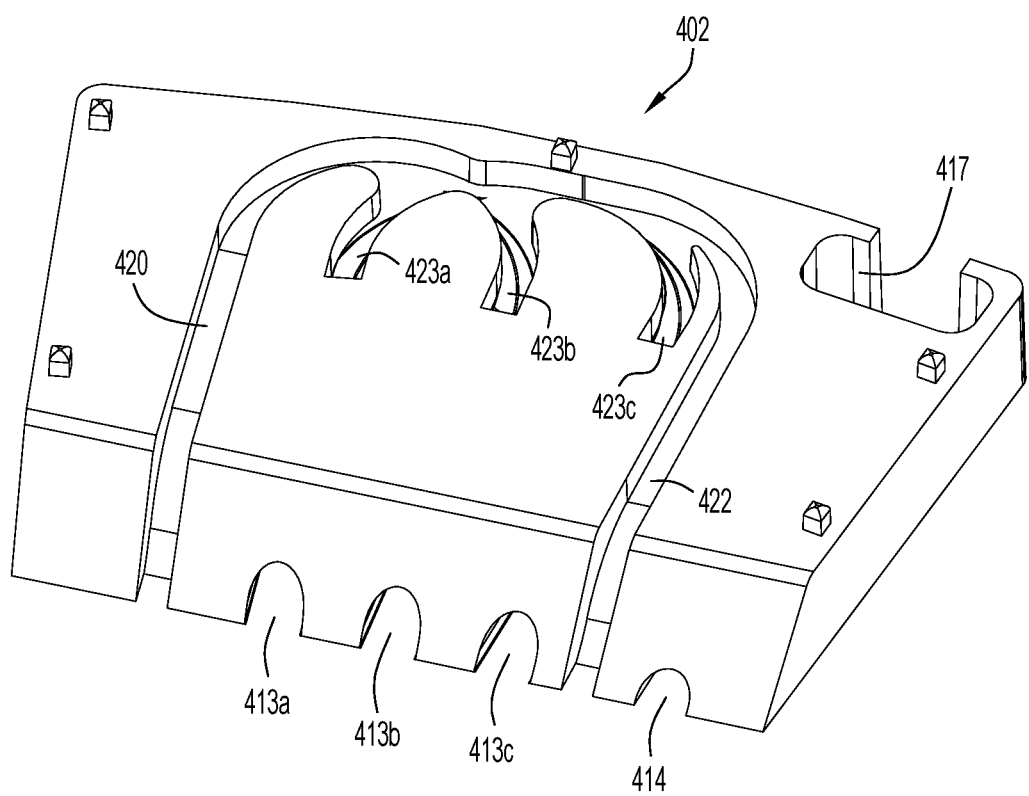
FIG. 37 is a top perspective view of a mid-tray according to one implementation.

In the implementation depicted in FIGS. 35A and 36 there are six optical fibers that extend from the fiber optic umbilical 500 into the hub 400. The six optical fibers are comprised of three end emitting fibers 302 that deliver light to the proximal connectors 304 of the infusion shafts and three end emitting fibers 337*a-c* that deliver light into the working lumens 308 of the infusions shafts inside the hub. The main shaft 200 and infusion shafts 300 are supported in the hub 400 in a manner consistent with that described above in conjunction with the implementation of FIG. 30.

Figure 35B:
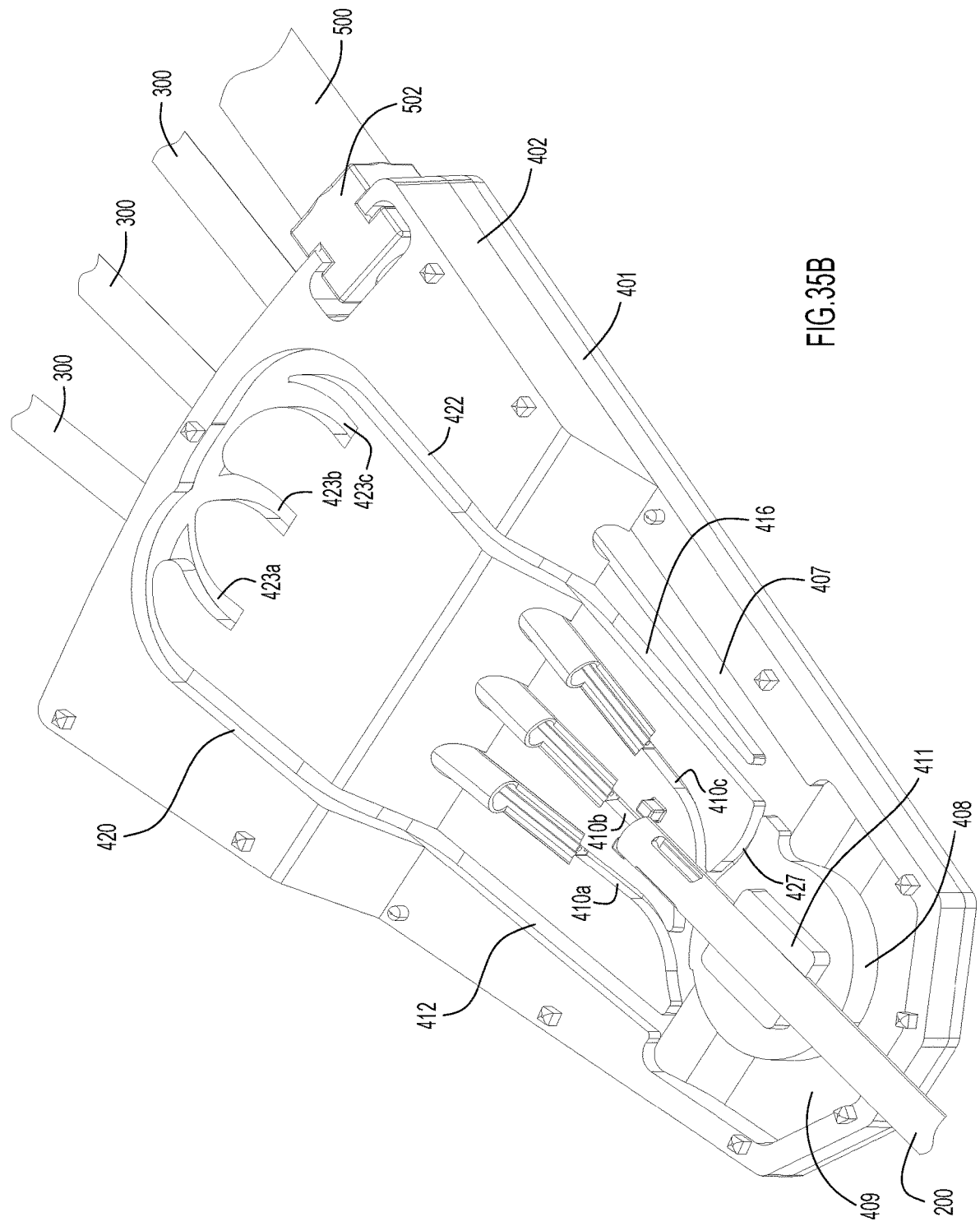
FIG. 35B shows the hub of FIG. 35A without the optical fibers.

FIG. 35B shows the hub of FIG. 35A without the optical fibers 302 and 337*a-c* to better identify the fiber channels 407, 409, 410*a-c*, 412, 416, 420, 422, 423*a-b* and 427 running through the hub 400. With reference to each of FIGS. 35A and 36, the end emitting fibers 302 that extend into the proximal connectors 304 of the infusion shafts 300 pass through the bottom tray 401 of the hub via fiber channels 407, 409 and a respective one of channels 410*a-c*. End emitting fiber 337*a* passes from the fiber optic umbilical 500 and into the fiber channel 423*a* in the mid-tray 402 via fiber channels 407, 409, 427, and 422. Each of end emitting fiber 337*b* and 337*c* passes from the fiber optic umbilical 500 and into its respective fiber channel 423*b* and 423*c* in the mid-tray 402 via fiber channels 407, 409 and 420. In the implementation of FIGS. 35A and 36 at least a portion of each of the end emitting fibers 337*a*, 337*b*, 337*c* overlaps with another one of the end emitting fibers 337*a*, 337*b*, 337*c* in one or both of the bottom tray 401 and mid-tray 402.

Figure 38:
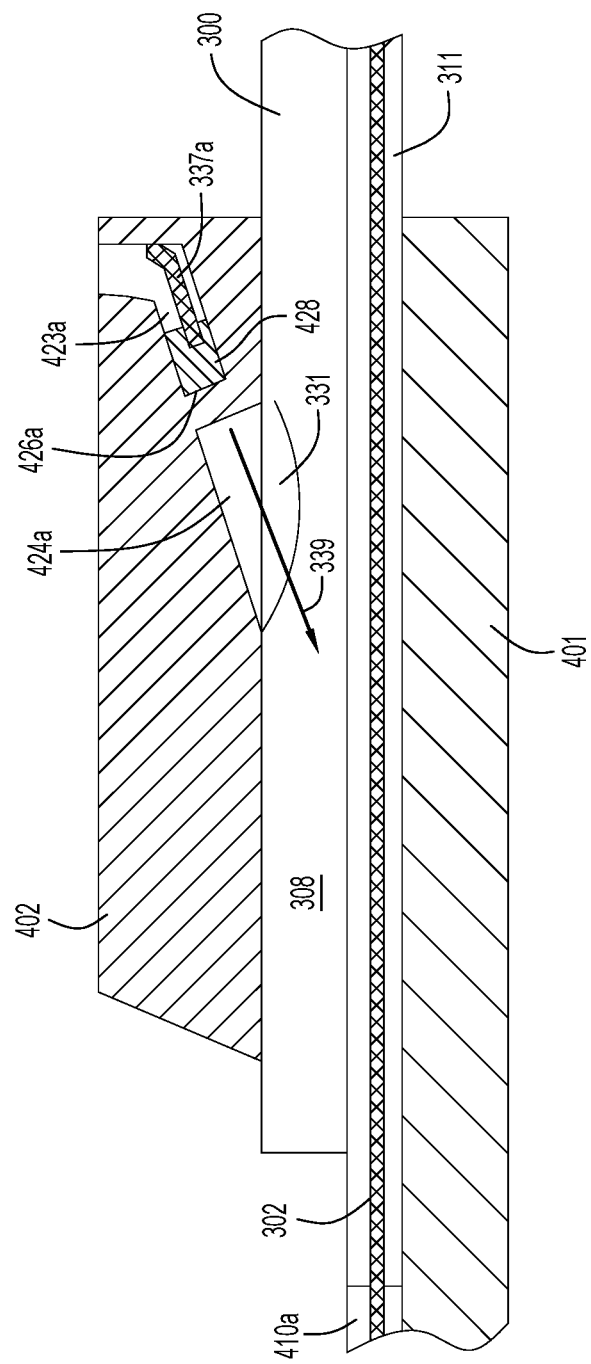
FIG. 38 is a cross-section side view of the hub shown in FIG. 35A.

FIG. 38 shows a cross-section view of the hub 400 with a first of the infusion shafts 300 secured between the bottom tray 401 and mid-tray 402. The end of the end emitting fiber 337*a* rests inside channel 423*a* facing an optical surface 426*a* formed on an inner surface of the mid-tray 402. In the implementation of FIG. 38, the end emitting fiber 337*a* is optically coupled with the optical surface 426*a* by use of an index matching gel or adhesive 428. According to one implementation an index matching adhesive is used to both secure the fiber 337*a* inside the downward sloping channel 423*a* and to optically couple the end emitting fiber to the optical surface 426*a*. A recess 424*a* inside the mid-tray 402 is positioned to reside over an opening 331 cut into the tubular body 303 of the infusion shaft 300. The arrangement of the end emitting fiber 337*a*, optical surface 426*a*, recess 424*a* and opening 331 results in bacterial disinfecting light 339 being transmitted from the end emitting fiber into the working lumen 308 of the infusion shaft 300 when disinfecting light is transmitted through the end emitting fiber. At least that portion of the mid-tray that resides between the distal end of optical fiber 337a and recess 424a is made of a material that is transparent or translucent to the disinfecting light 339. According to some implementations the entirety of the mid-tray 402 is made of a material that is transparent or translucent to the disinfecting light 339.

End emitting fibers 337b and 337c may be arranged similar to fiber 337a to effectuate a disinfecting of at least a portion of the working lumens 306 of the other infusion shafts 300.

Like with the implementation of FIG. 30, one or more or all of the fibers 302 and 337a-c is routed in the hub 400 so as not to be taut along at least a portion of the structures that form the fiber channels located in the bottom tray 401. This provision of slack in the one or more optical fibers guards against excessive tensile forces being applied to the fibers when the infusion shafts 300 are bent. This is particularly important where at least a portion of the optical fiber is longitudinally fixed inside infusion shaft, like with certain implementations of the end emitting fibers 302 discussed above.

Fluidly connecting the working lumens 308 of the infusion shafts 300 to the working lumens 201a-c of the main shaft 200 may be accomplished in a manner similar to that described above in conjunction with the implementation of FIG. 30. Like with the implementation of FIG. 30, when the casting process is complete, the entirety of the hub 400 may be encapsulated by the casting material and assume an appearance like that shown in FIG. 3.

To protect against breaking the end emitting fibers, the bends of the fiber channels that contain them are constructed to prevent a bending of the optical fibers beyond their minimum bending radius. For example, one or more or all of the bends may have a radius of curvature that is equal to or greater than the minimum bending radius of the optical fiber. Also, as shown in FIG. 36, the path of the optical fibers about the raised platform 408 may be selected to ensure that the optical fibers do not bend beyond their minimum bending radius. For this purpose some of the optical fibers may travel in a clockwise direction about the raised platform 408, while others travel in a counter-clockwise direction about the raised platform. In the Implementation of FIGS. 35A-38 all the end emitting optical fibers travel in a clockwise direction about the raised platform 408 (as viewed from above the bottom tray 401) except fiber 337a that travels in a counter-clockwise direction about the raised platform. The provision of alternate pathways for the optical fibers to travel around the raised platform 408 increases design freedom, particularly in the layout of the bottom tray 410 and mid-tray 402 fiber channels. The provision of alternate pathways can also facilitate a smaller hub design to provide it with a footprint that is more comparable to the foot print of a traditional CVC hub. As discussed above, by maintaining the disinfecting CVC design similar to traditional CVC designs established clinical practices may be followed.

Light reflectors may be incorporated into, attached to or coated on the hub 400 in a manner consistent with that described above in conjunction with the implementation of FIG. 30.

Figure 39A:
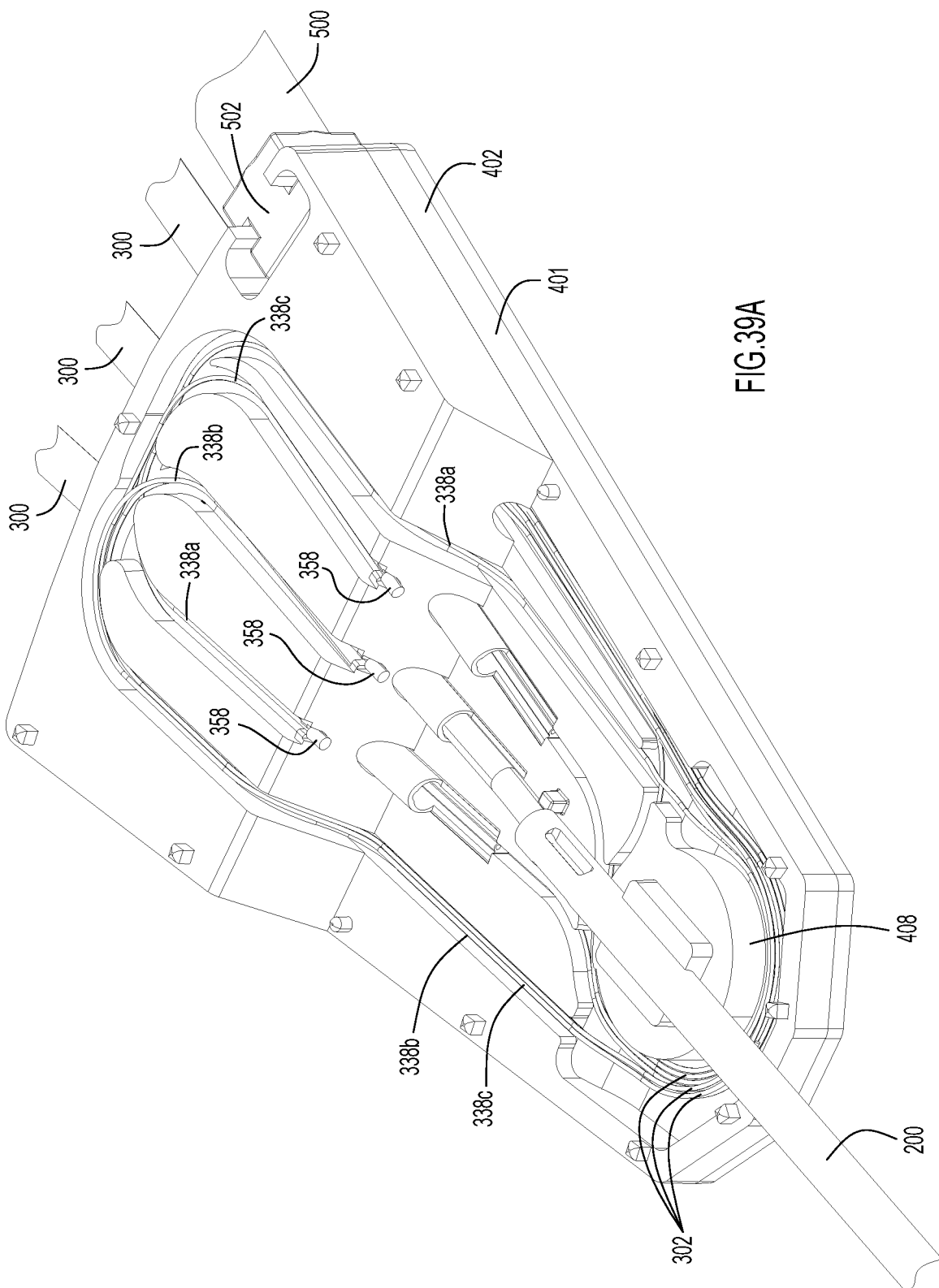
FIGS. 39A-D are perspective views of a partially constructed hub of a central venous catheter according to other implementations.

FIG. 39A illustrates a partially constructed hub 400 of a CVC according to another implementation. Like with the previously described implementations, the hub is configured to fluidly connect the working lumens 308 of the infusion shafts 300 to the working lumens 201a-c of the main shaft 200. The conduits that connect the working lumens may be like those discussed above in conjunction with the implementation of FIG. 30.

According to some implementations disinfecting light is delivered into the CVC only by way of use of end emitting fibers. As a result, according to some implementations each of the infusion shafts 300 and main shaft 200 is devoid of a radially emitting fiber and a radially emitting fiber lumen.

In the implementation of FIG. 39A the disinfecting light is delivered into one or more of the proximal connectors 304 of the infusion shafts 300 in a manner consistent with what has been described above with one or more optical surfaces and/or one or more light reflectors of the proximal connector being used to disperse disinfecting light emitted from an end emitting fiber 302 into at least a portion of the infusion shaft. Disinfecting light is also delivered out the ends 358 of other end emitting fibers 338a-c to flood at least that region of the hub that contains the conduits connecting the working lumens of the infusion shafts 300 and main shaft 200.

According to some implementations the ends of end emitting fibers 338a-c comprise end caps 358 that are optically coupled to the cores of the end emitting fibers. When the hub is fully constructed the ends of the end emitting fibers 336a-c will reside in the casting material that envelops the hub. The use of the end caps 358 provides at least two advantages. The advantage is that by lowering the power density of the light that exits the fibers the light will be below the damage threshold of the casting material.

Figure 39B:
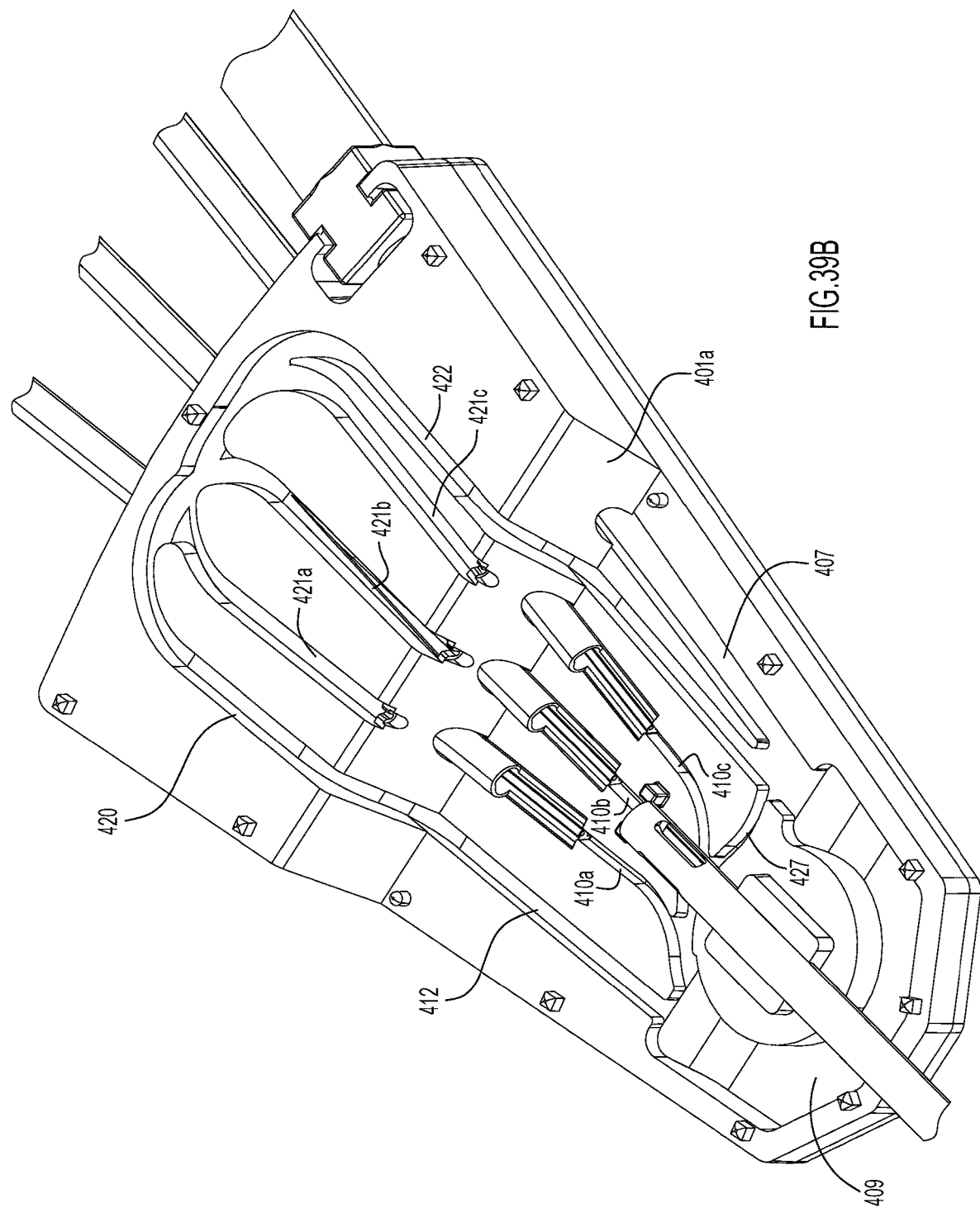
Figure 39C:
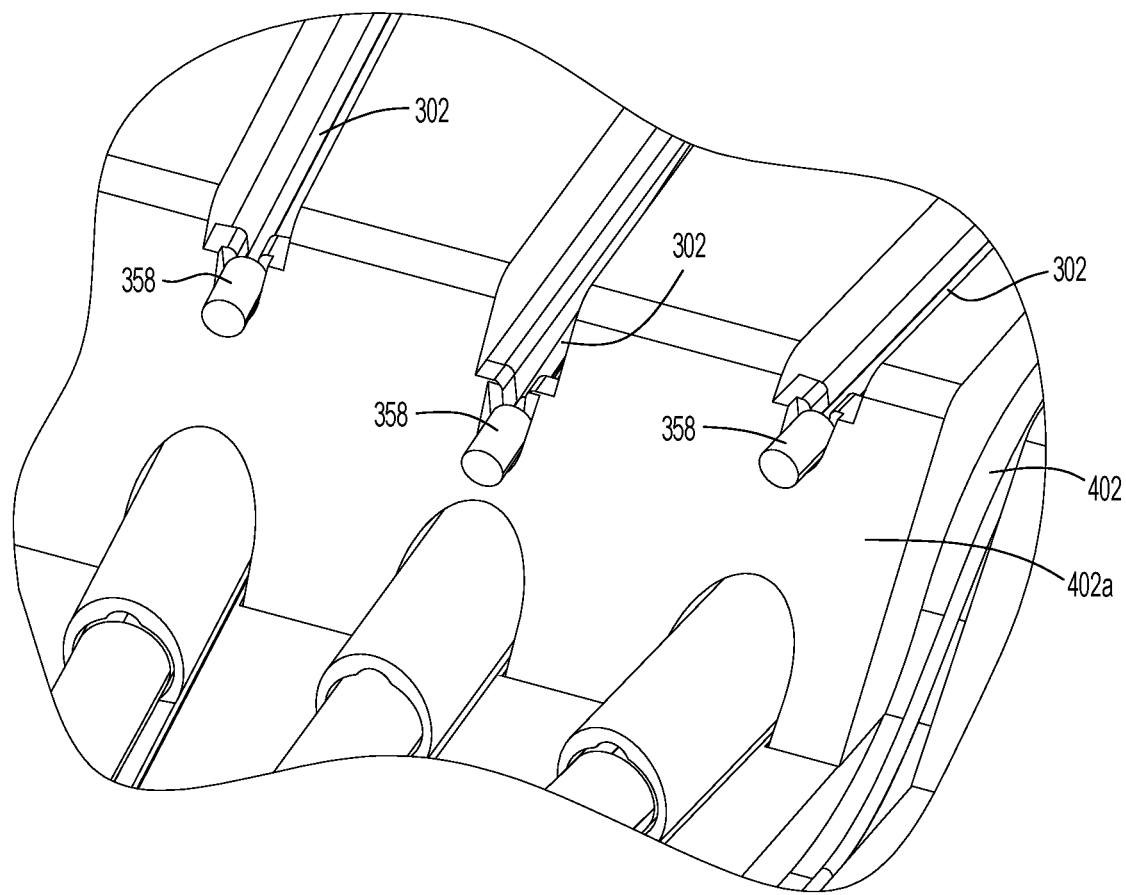
Figure 39D:
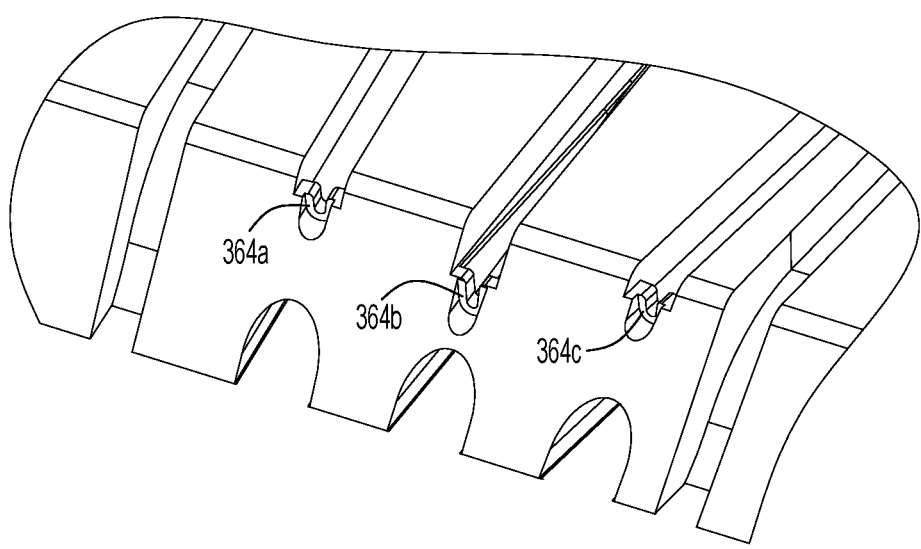

As shown in FIG. 39D, according to some implementations support fixtures 364a-c are provided at or near the distal end of channels 421a-c to assist in respectively fixing the ends of the end emitting fibers 338a-c on the hub. As illustrated in FIGS. 39A and 39C, according to some implementations the core and cladding portion of the end emitting fibers 338a-c are clamped inside the support fixtures 364a-c with the end caps 358 being positioned to protrude from the face 402a of the mid-tray 402. According to other implementations the end caps 358 are instead held fixing inside the support fixtures 364a-c.

Although not shown, the CVC of FIG. 39A may also include an imaging fiber 207 that runs along a length of the main shaft 200 as described above.

In the implementation depicted in FIG. 39A there are six optical fibers that extend from the fiber optic umbilical 500 into the hub 400. The six optical fibers are comprised of three end emitting fibers 302 that deliver light to the proximal connectors 304 of the infusion shafts 300 and three end emitting fibers 338a-c that deliver light into the region of the hub that contains the conduits connecting the aforesaid working lumens of the infusion shafts 300 and main shaft 200. The main shaft 200 and infusion shafts 300 are supported in the hub 400 in a manner consistent with that described above in conjunction with the implementation of FIG. 30.

FIG. 39B shows the hub of FIG. 39A without the optical fibers 302 to better identify the fiber channels 407, 409, 410a-c, 412, 416, 420, 421a-c, 422 and 427 running through the hub 400. The end emitting fibers 302 that extend into the proximal connectors 304 of the infusion shafts 300 pass through the bottom tray 401 of the hub via fiber channels 407, 409 and a respective one of channels 410a-c. End emitting fiber 338a passes from the fiber optic umbilical 500 and into the fiber channel 421a in the mid-tray 402 via fiber channels 407, 409, 427, and 422. Each of end emitting fiber 338b and 338c passes from the fiber optic umbilical 500 and into its respective fiber channel 421b and 421c in the mid-tray 402 via fiber channels 407, 409 and 420. In the implementation of FIG. 39A at least a portion of each of the end emitting fibers 338a, 338b, 338c overlaps with another one of the end emitting fibers 338a, 338b, 338c in one or both of the bottom tray 401 and mid-tray 402.

As shown in FIG. 39A, the distal end of each of the end caps 358 of the end emitting fibers 338a-c faces distally toward the region where the conduits that join the working lumens of the infusion shafts and main shaft are to reside. Accordingly, disinfecting light emitted by the end emitting fibers 302 is directed on and through the conduits to effectuate a disinfecting of the same. For this purpose, the casting material that is ultimately used to encapsulate the hub and to form the connecting conduits inside the casting is transparent or translucent to the disinfecting light.

Like with the implementation of FIG. 30, one or more or all of the fibers 302 and 338a-c is routed in the hub 400 so as not to be taut along at least a portion of the structures that form the fiber channels located in the bottom tray 401. This provision of slack in the one or more optical fibers guards against excessive tensile forces being applied to the fibers when the infusion shafts 300 are bent. This is particularly important where at least a portion of the optical fiber is longitudinally fixed inside the infusion shaft, like with certain implementations of the end emitting fibers 302 discussed above.

Fluidly connecting the working lumens 308 of the infusion shafts 300 to the working lumens 201a-c of the main shaft 200 may be accomplished in a manner similar to that described above in conjunction with the implementation of FIG. 30. Like with the implementation of FIG. 30, when the casting process is complete, the entirety of the hub 400 may be encapsulated by the casting material and assume an appearance like that shown in FIG. 3.

To protect against breaking the end emitting fibers, the bends of the fiber channels that contain them are constructed to prevent a bending of the optical fibers beyond their minimum bending radius. For example, one or more or all of the bends of the fiber channels may have a radius of curvature that is equal to or greater than the minimum bending radius of the optical fiber. The path of the optical fibers about the raised platform 408 in the bottom tray 401 may also be selected to ensure that the optical fibers do not bend beyond their minimum bending radius. For this purpose some of the optical fibers may travel in a clockwise direction about the raised platform 408, while others travel in a counter-clockwise direction about the raised platform. In the implementation of FIG. 39A all the end emitting optical fibers travel in a clockwise direction about the raised platform 408 (as viewed from above the bottom tray 401) except fiber 358a that travels in a counter-clockwise direction about the raised platform. The provision of alternate pathways for the optical fibers to travel around the raised platform 408 increases design freedom, particularly in the layout of the bottom tray 401 and mid-tray 402 fiber channels. The provision of alternate pathways can also facilitate a smaller hub design to provide it with a footprint that is more comparable to the foot print of a traditional CVC hub. As discussed above, by maintaining the disinfecting CVC design similar to traditional CVC designs established clinical practices may be followed.

Light reflectors may be incorporated into, attached to or coated on the hub 400 in a manner consistent with that described above in conjunction with the implementations of FIG. 30. For example, the casting material that surrounds the connecting conduits when the hub is encapsulated may have embedded therein one or more light reflecting elements that assist in directing the disinfecting light toward the conduits.

As mentioned above, in certain instances radially emitted disinfecting light and end emitted disinfecting light may be delivered to certain parts of the CVC by use of a single optical fiber. In the implementations of both FIGS. 35A and 39A one or more of the end emitting fibers may be substituted with such a fiber to increase the surface area that is exposed to the disinfecting light. For instance, in the implementation of FIG. 39A each of fibers 302 may be substituted with a dual radial and end emitting fiber. This would result in a disinfection of the connecting conduits with the end emitted light as discussed above, and would also result in a disinfection of those portions of the infusion shafts that reside below the mid-tray 402 with the radial emitted light. For this purpose, according to some implementations at least a portion of the length of the fiber channels 421a-c located in the mid-tray 402 are aligned with the tubular body 303 of the infusion shafts 300 located below the mid-tray. Furthermore, because all of the optical fibers in one way or another pass across at least a portion of the main shaft 200 inside the hub 400, the radial emitted light emanating from these fibers can also be used to cause a disinfecting of the main shaft inside the hub.

In a modified implementation of the CVC of FIG. 35A one or more of fibers 337a-c is a dual radial and end emitting fiber and fibers 302 are end emitting fibers. In a like manner, in a modified implementation of the CVC of FIG. 39A one or more of fibers 338a-c is a dual radial and end emitting fiber and fibers 302 are end emitting fibers.

Figure 40:
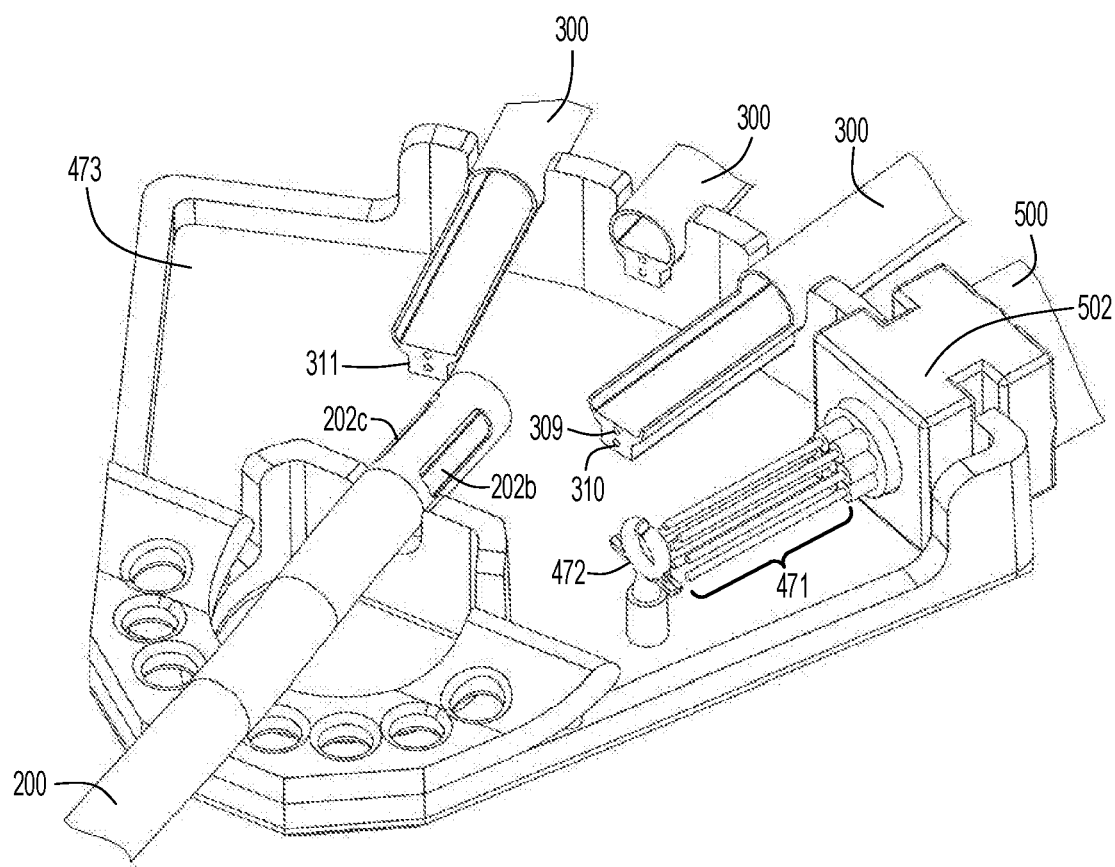
FIG. 40 illustrates a partially constructed hub of a central venous catheter according to another implementation.

FIG. 40 depicts a partially constructed hub 470 of a CVC according to another implementation wherein optical fibers 471 are routed through the hub by use of support fixtures 472 dispersed about and supported on the hub tray 473. The hub is configured to support the distal ends of the infusion shafts 300 and the proximal end of the main shaft 200. Upon the optical fibers 471 being properly routed into their respective lumens inside the infusion shafts 300 and/or main shafts 300, the fibers are appropriately covered during a process in which the hub is encased by a casting material. With beadings/mandrels extending between the working lumens of the infusion shafts 300 and main shaft 200 as described above, the conduits that fluidly connect the working lumens are formed during the casting process. The support fixtures 472 are disbursed about the hub in a manner that prevents a bending of one or more or all of the optical fibers 471 beyond their minimum bending radius. In the implementations discussed above, one or more of the fiber channels may be substituted with one or more support fixtures 472 to guide the fibers to their desired destination and in a way that prevents them from bending beyond their minimum bending radius.

Figure 41:
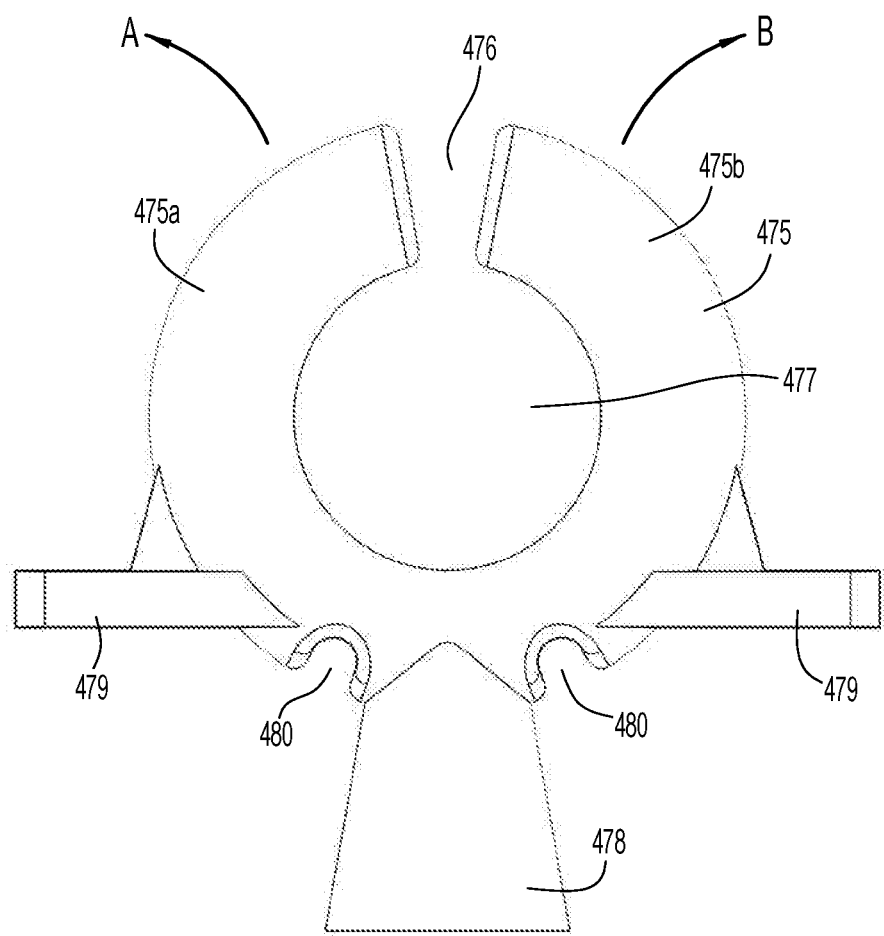
FIG. 41 shows a fixture for routing optical fibers within the hub of FIG. 40

According to one implementation the support fixture 472 includes an expandable elastomeric O-ring 475 that has a top opening/gap 476 through which the optical fibers 471 may be introduced into the O-ring opening 477. The elastomeric O-ring is resiliently biased in the position shown in FIG. 41.

The O-ring is supported on a post 478 that is attached to the floor of the hub tray 473. Notches 480 in the bottom portion of the O-ring produce hinges that allow the arms 475a and 475b of the O-ring to be flexed outward in opposite directions A and B to increase the size of the gap 476 when a downward force is applied to the protruding arms 479 located near the base of the O-ring. When the downward applied force to the arms 479 is released, the arms 475a and 475b of the O-ring attempt to return to their original position to lock the optical fibers within the opening 477.

As discussed above in conjunction with FIGS. 10B and 10C, according to some implementations one or more of the infusion shafts 300 are equipped with dual working lumens 308a and 308b that are separated by a longitudinal wall/septum 321. In the aforestated implementations the radially emitting fiber lumen 309 and end emitting fiber lumen 310 are located in the septum 321.

In the discussion that follows, apparatus and methods for forming conduits between the respective working lumens of the infusion shafts 300 to the working lumens of the main shaft are disclosed. A portion of the conduits are formed during a casting process like those described above, wherein a casting material is used to encapsulate the hub. During the casting process at least a portion of the length of the conduits is formed with the use of strategically placed mandrels that are enveloped in the casting material during the casting process and ultimately removed.

According to some implementations the apparatus includes a hub 600 that is adapted to makes use of mandrels 604a, 604b to form conduits to connect the two working lumens 308a, 308b of a single infusion shaft 300 to a common working lumen inside the main shaft 200. Although the discussion below is directed primarily to fluidly coupling the two working lumens of an infusion shaft 300c to the working lumen 201c of the main shaft 200, it is appreciated that the working lumens of the other infusion shafts 300a, 300b may be coupled with the working lumens 201a and 201b of the main shaft 200 in a similar manner.

Figure 43:
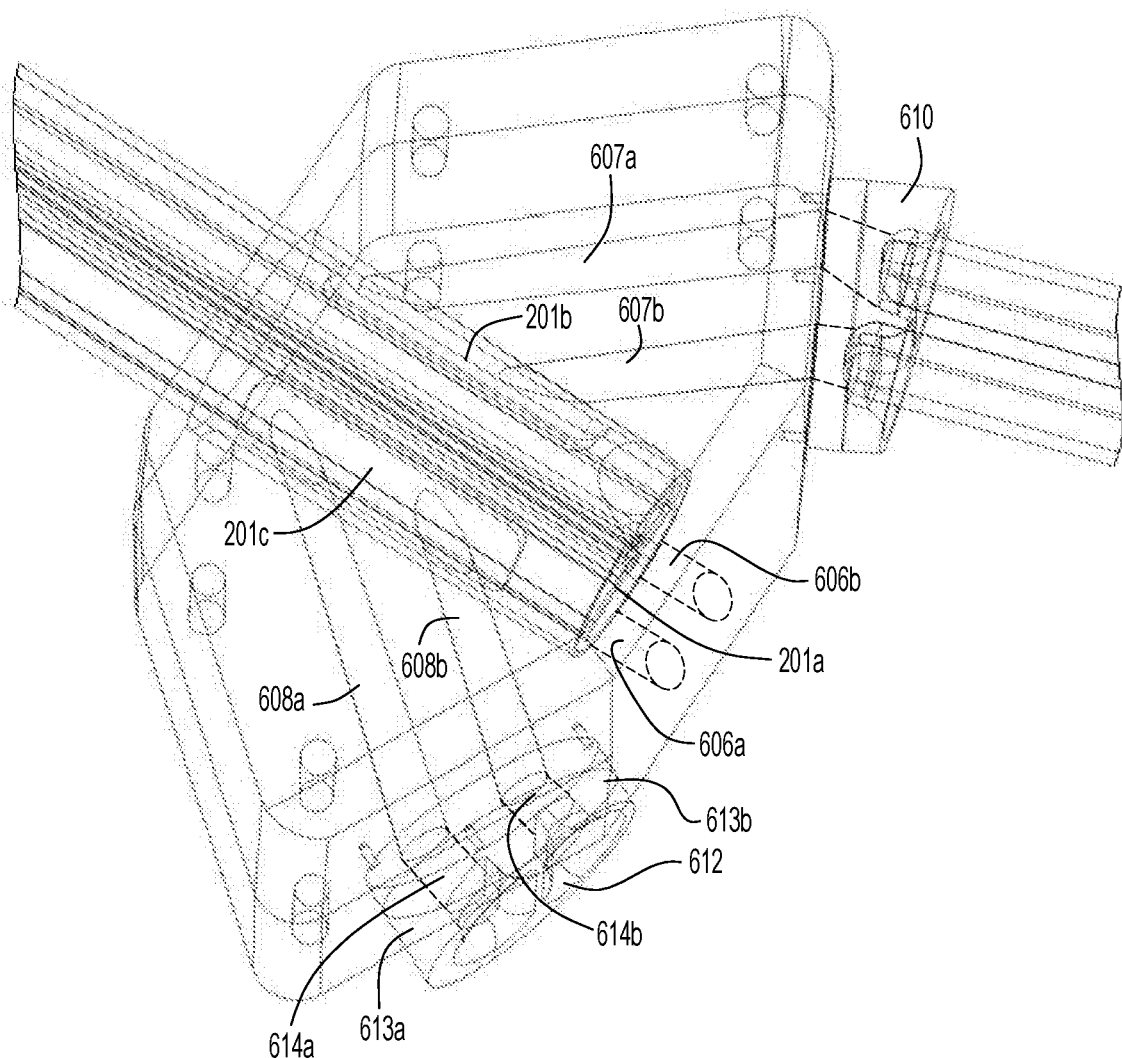
FIG. 43 is a transparent view of a manifold of the hub of FIG. 43 having internal conduits that are fluidly coupled to the working lumens of the main shaft.

According to one implementation the hub 600 includes a tray 601 onto which are arranged at a proximal end thereof infusion shaft support fixtures 605a-c. The proximal end of the main shaft 200 of the CVC resides inside a manifold 602 located at the distal end of the tray 601. As best seen in FIG. 43, the manifold includes internal conduits 606a, 606b, 607a, 607b, 608a and 608b that are fluidly coupled with the working lumens 201a-c of the main shaft 200. Internal conduits 606a and 606b are fluidly coupled with working lumen 201a, internal conduits 607a and 607b are fluidly coupled with working lumen 201b, and internal conduits 608a and 608b are fluidly coupled with working lumen 201c.

The proximal face of the manifold 602 includes mandrel support fixtures 610 and 612 that have multiple lumens (e.g. 2 lumens) fluidly coupled to the internal conduits of the manifold that are respectively coupled to the working lumens 201b and 201c of the main shaft 200. Although not shown in the figures, the manifold 602 may also include a mandrel support fixture that has multiple lumens (e.g. 2 lumens) that communicate with the working lumen 201a of the main shaft 200.

Figure 44:
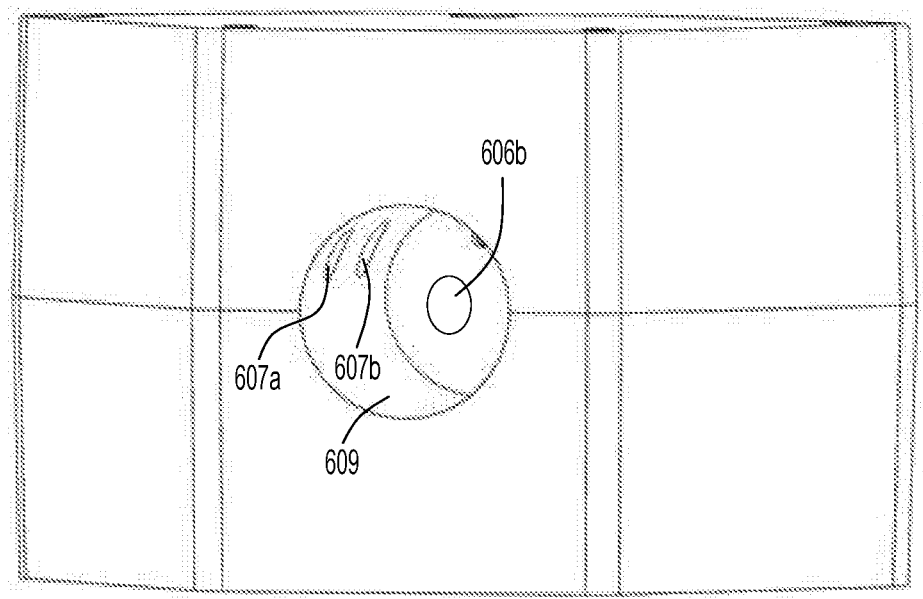
FIG. 44 is a perspective view of the distal side of the manifold of FIG. 43.

FIG. 44 shows a distal side of the manifold 602 that includes an opening 609 into which the proximal end of the main shaft 200 resides when the hub 600 is fully assembled. The opening 609 is in fluid communication with each of internal conduits 606a, 606b, 607a, 607b, 608a and 608b. According to some implementations the proximal end of the main shaft 200 is fixed inside the opening 609 by use of an adhesive. The proximal end of the main shaft may also be press-fit inside the opening 609. In any event, each of the inlets of the working lumens 201a-c are aligned with a respective pair of the internal conduits as shown in FIG. 43.

Figure 45A:
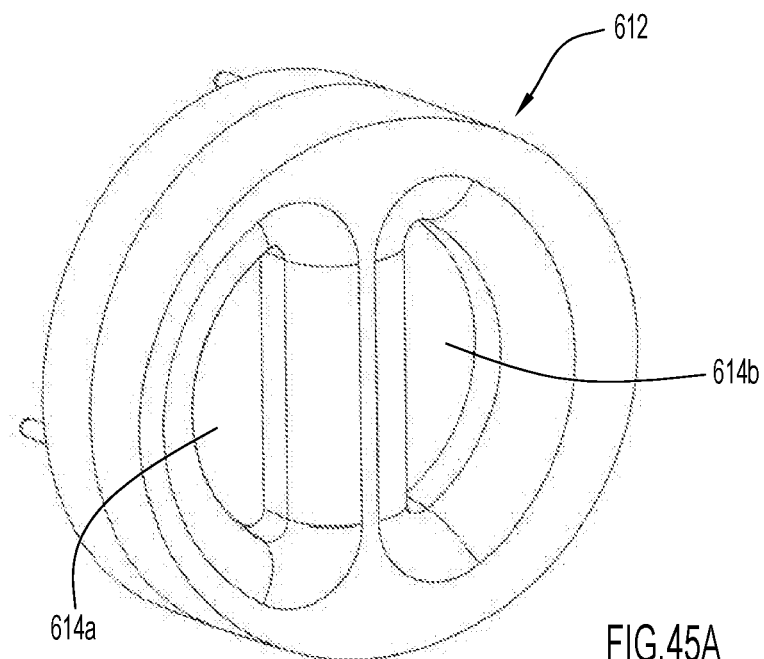
FIGS. 45A and 45B show perspective views of a manifold adapter according to one implementation.
Figure 45B:
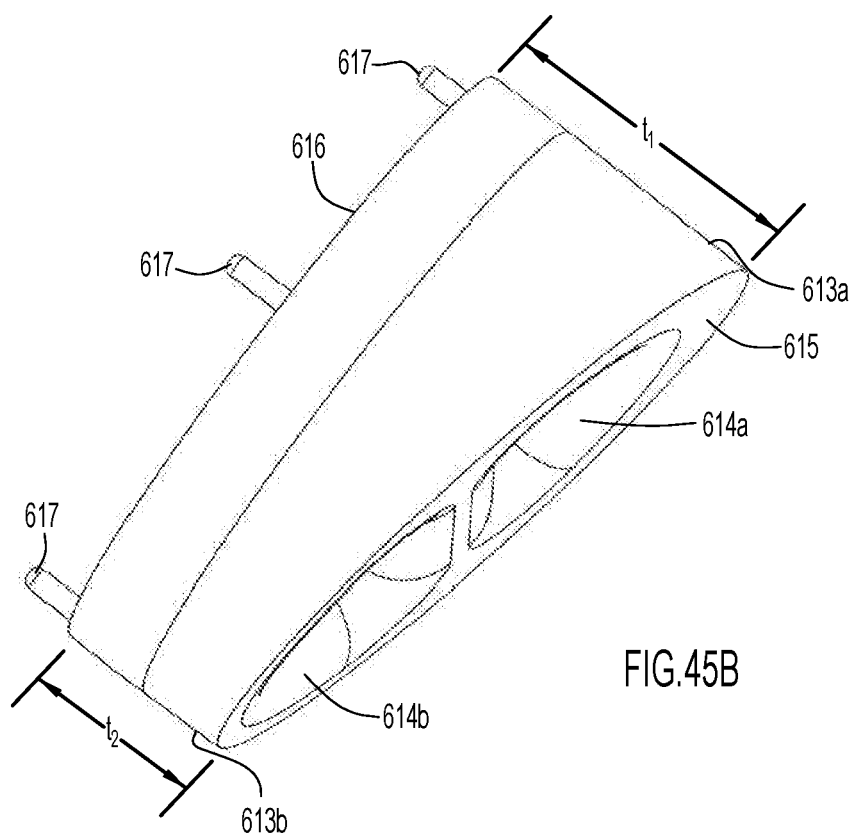

The mandrel support fixture 612 includes a proximal side 615, a distal side 616 and two through lumens 614a and 614b that each extends between the proximal and distal sides. Through lumen 614a is in fluid communication with manifold conduit 608a and through lumen 614b is in fluid communication with manifold conduit 608b. According to some implementations the mandrel support fixtures 610 and 612 located on the sides of the manifold 602 each have sloped proximal sides 615. For example, as shown in FIGS. 43 and 45B, the outer side 613a of the fixture 612 has a thickness t1 and the inner side 613b of the fixture 612 has a thickness t2 that is less than the thickness of t1. The purpose of the sloped proximal side is discussed below. According to some implementations fixture 612 is attached to the manifold 602 by the use of posts 617 that protrude from its distal side 16 into openings (not shown) in the proximal side of the manifold 602.

Figure 42:
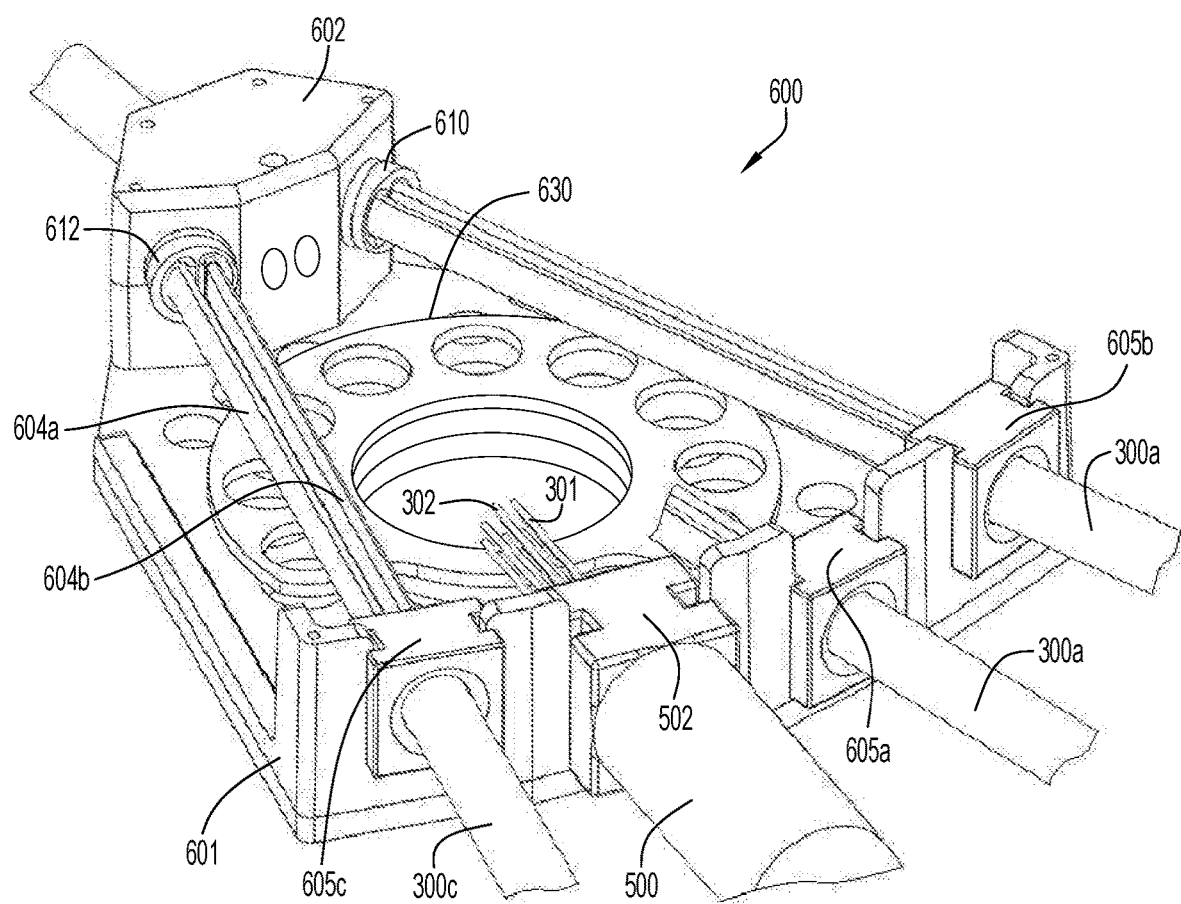
FIG. 42 is a perspective view of a partially constructed hub of a central venous catheter according to another implementation.
Figure 46:
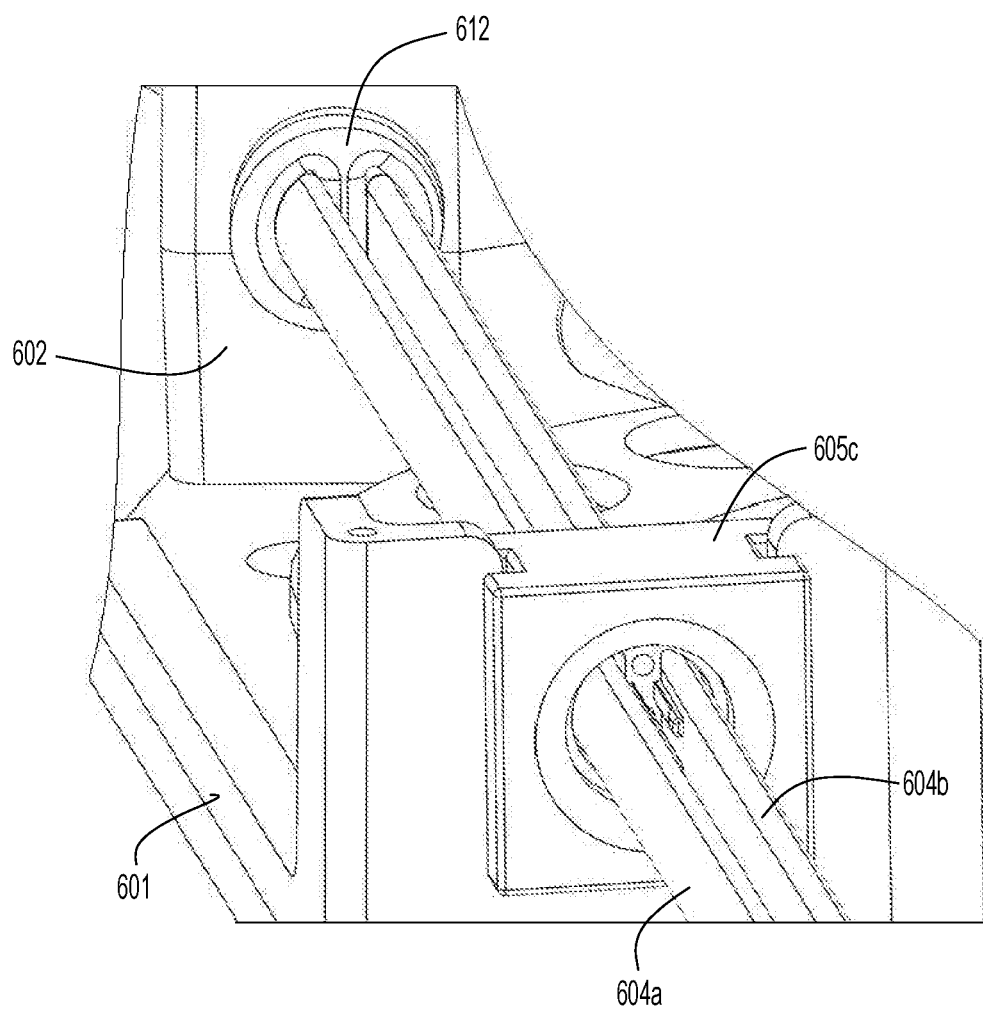
FIG. 46 shows mandrels being supported inside an infusion shaft support fixture and the manifold adapter of the hub of FIG. 42.

As briefly mentioned above, a proximal end of the hub tray 601 includes infusion shaft support fixtures 605a-c. Each of the infusion shaft support fixtures 605a-c is configured to couple the distal end of an infusion shaft 300a-c to the hub 600 and to also accommodate a passage of the mandrels from inside the infusion shafts into the hub 600. When, for example, the mandrels 604a and 604b are in place during the manufacturing of the hub 600 as shown in FIGS. 42 and 46, they extend through the working lumens 308a, 308b of the infusion shaft 300c, through the infusion shaft support fixture 605c and into the mandrel support fixture 612 located on the manifold 602.

Figure 47A:
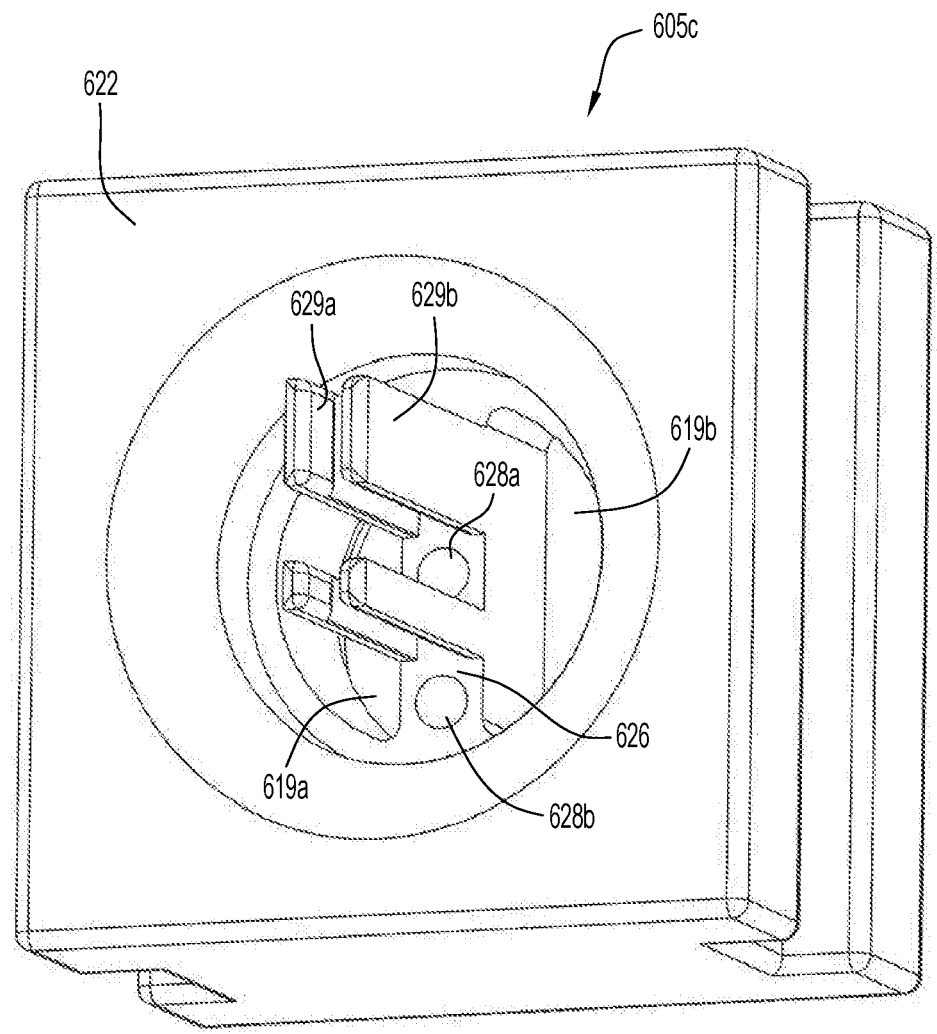
FIG. 47A shows a proximal side of the infusion shaft support fixture of FIG. 46.
Figure 47B:
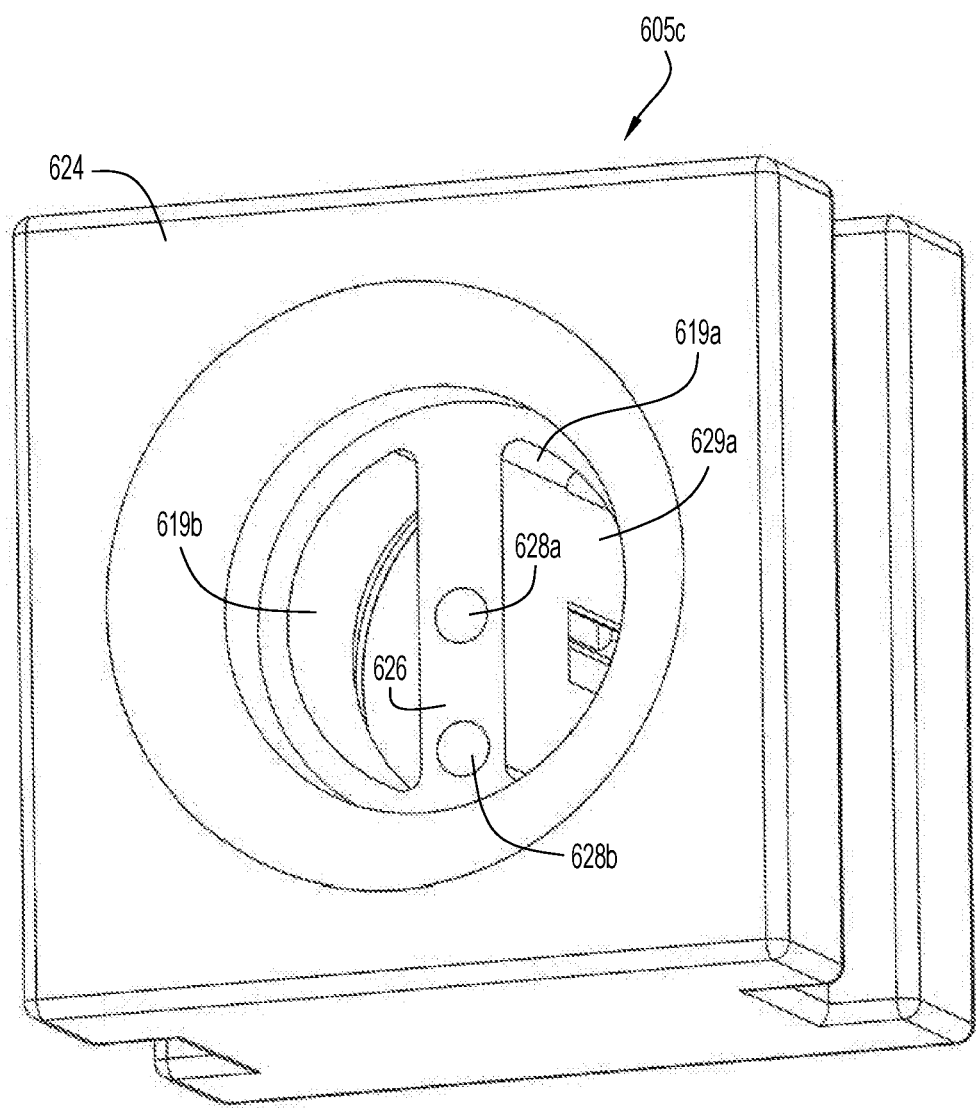
FIG. 47B shows a distal side of the infusion shaft support fixture of FIG. 46.

FIGS. 47A and 47B respectively show the proximal and distal sides 622 and 624 of the infusion shaft support fixture 605c according to one implementation. The fixture includes first and second through lumens 619a and 619b that extend between the proximal and distal sides 622 and 624. Disposed between lumens 619a and 619b is a septum 626 through which two other through lumens 628a and 628b pass. According to some implementations the distal end of the infusion shaft 300c is attached to the proximal side 622 of the fixture 605c by use of a pair of wall segments 629a and 629b that protrude proximally from the septum 626. The wall segments are spaced-apart so that a gap exists between them. Attachment of the proximal end of the infusion shaft 300c is accomplished by inserting the septum 321 of the infusion shaft between the spaced-apart wall segments 629a and 629b so that the face of the shaft septum 321 abuts the proximal face of the fixture septum 626. When the infusion shaft 300c is attached to the fixture 605c the radially emitting fiber lumen 309 is axially aligned with lumen 628a and the end emitting fiber lumen 310 is axially aligned with lumen 628b. In this way, optical fibers 301 and 302 may be routed from the fiber optic umbilical 500 and respectively into lumens 628a and 628b of the fixture 605c, and then into the fiber lumens 309 and 310 of the infusion shaft 300c. Examples of how the fiber 301 and 302 may reside inside the infusion shaft are discussed above.

According to some implementations, a roundabout 630 is located inside the hub tray 601 which is used to route the optical fibers to their destinations in a manner that prevents the fibers from bending beyond their minimum bending radius. For example, fibers 301 and 302 may extend from the umbilical hub connector 502 in a counter-clockwise direction about the roundabout 630 and into their respective lumens 628a and 628b of the infusion shaft support fixture 605c. According to some implementations the radius of curvature of the one or more bends in the roundabout 630 is each greater than the minimum bending radius the optical fibers 301 and 302. The remainder of the optical fibers may be delivered to infusion shafts 300a and 300b in a similar way, but in a clockwise direction about the roundabout 630.

Upon optical fibers 301 and 302 being placed inside infusion shaft 300c, mandrels 604a and 604b may be introduced respectively into the working lumens 308a and 308b through the proximal opening in the proximal connector 304. The lengths of the mandrels are sufficient for them to pass through the infusion shaft 300c and through the hub tray 601 until their distal ends reside supported in the mandrel support fixture 612. When the mandrels 604a and 604b are in place, each of their distal ends respectively resides inside the through lumens 614a and 614b of the fixture 612 and their proximal ends reside outside the proximal connector 304 of the infusion shaft 300c. When the optical fibers and mandrels for all of the infusions shafts and main shaft are in place, the assembly is cast as discussed above to form an encapsulated hub that has an appearance similar to the hub 400 shown in FIG. 3.

As discussed above the proximal side 615 of the mandrel support fixture 612 is sloped. The purpose of the slope is to align the proximal side 615 in a plane that is parallel with that of the distal side 624 of the infusion shaft support fixture 605c. This provides a direct line of sight between the lumens 619a and 619b of fixture 605c with the lumens 614a and 614b of fixture 612 to allow the placement of straight rigid mandrels between the respective lumens.

While specific implementations and applications have been illustrated and described, it is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention.

For example, the disclosure describes in detail various implementations of a CVC and of its individual components. It is appreciated, however, that the disclosed inventive features are applicable to a host of other types of devices inside and outside the medical field. As mentioned above, the apparatus and methods disclosed herein can also be applied to equipment or components of water processing plants, food processing plants, dairies, livestock habitation facilities, etc.

The following clauses disclose in an unlimited way additional implementations, with each clause representing an implementation. Additional implementations are represented by one or more of the implementations of one group or groups of clauses with one or more implementations of another group or groups of clauses. Group A through H clauses are provided.

Group a Clauses:

Clause 1. An assembly comprising:
a first optical fiber having a length;
a first body having a first receptacle in which at least a portion of the length of the first optical fiber resides.

Clause 2. The assembly according to clause 1, wherein the first optical fiber is a radially emitting fiber that is configured to radially emit bacterial disinfecting light to disinfect at least a portion of the first body.

Clause 3. The assembly according to clause 1, wherein the first optical fiber is an end emitting fiber that is configured to end emit bacterial disinfecting light to disinfect at least a portion of the first body.

Clause 4. The assembly according to clause 1, wherein the first optical fiber is a radially emitting and end emitting fiber that is configured to radially emit bacterial disinfecting light to disinfect at least a portion of the first body.

Clause 5. The assembly according to clause 1, wherein the first optical fiber is a dual emitting fiber that is configured to radially emit bacterial disinfecting light to disinfect at least a first portion of the first body and to end emit bacterial disinfecting light to disinfect at least a second portion of the first body.

Clause 6. The assembly according to clause 1, further comprising a second optical fiber having a length, the first body having a second receptacle in which at least a portion of the length of the second optical fiber resides.

Clause 7. The assembly according to clause 6, wherein the first optical fiber is an end emitting fiber that is configured to end emit bacterial disinfecting light to disinfect at least a first portion of the first body, and the second optical fiber is a radially emitting fiber that is configured to radially emit bacterial disinfecting light to disinfect at least a second portion of the first body.

Clause 8. The assembly according to clauses 1, 3 and 7, wherein at least a portion of the first optical fiber is attached to the first body inside the first receptacle.

Clause 9. The assembly according to clauses 1, 2 and 4, wherein the first optical fiber is not attached to the first body and is slideable inside the first receptacle.

Clause 10. The assembly according to clauses 3, 5 and 7, wherein the first body includes one or more optical surfaces that direct the end emitted bacterial disinfecting light onto the second portion of the first body.

Clause 11. The assembly according to clause 6, wherein the second optical fiber is an imaging fiber.

Clause 12. The assembly according to clauses 2, 3, 6, 9 and 11, wherein the first body is a main shaft of a central venous catheter.

Clause 13. The assembly according to clauses 2-7 and 9-10, wherein the first body is an infusion shaft of a central venous catheter.

Clause 14. The assembly according to clauses 1-13, wherein the first body has a working lumen and an external surface, the external surface comprising a light reflective coating that is configured to reflect at least a portion of the radial emitted disinfecting light into the working lumen.

Clause 15. The assembly according to clauses 1-13, wherein the first body has a working lumen and an external surface, the external surface having disposed thereon a reflective film that is configured to reflect at least a portion of the radial emitted disinfecting light into the working lumen.

Clause 16. The assembly according to clause 15, wherein the film is heat shrunk onto the external surface of the first body.

Clause 17. The assembly according to clauses 1, 2, 4 and 5-7, wherein the first body has a working lumen and a light reflector, the light reflector being embedded in the first body and configured to reflect at least a portion of the radial emitted disinfecting light into the working lumen.

Clause 18. The assembly according to clauses 1, 3 and 5-7, wherein the first body has a working lumen and a light reflector, the light reflector being embedded in the first body and configured to reflect at least a portion of the end emitted disinfecting light into the working lumen.

Clause 19. The assembly according to clause 7, wherein the first body has a working lumen and a light reflector located between the first and second receptacles, the light reflector being embedded in the first body and configured to reflect at least a portion of the radially emitted disinfecting light into the working lumen.

Clause 20. The assembly according to clauses 1-5, wherein a part of the first body that contains the first and second optical fibers is resistive to being bent beyond a minimum bending radius of the first and second optical fiber.

Clause 21. The assembly according to clauses 3, 5 and 7, wherein the first optical fiber comprises at an end thereof a power density lowering end cap.

Group B Clauses:

Clause 1. An assembly comprising:
a first optical fiber having a length;
a first body having a receptacle in which at least a first portion of the length of the first optical fiber resides;
a second body having formed therein a first channel that houses at least a second portion of the length of the first optical fiber.

Clause 2. The assembly according to clause 1, wherein the first optical fiber is a radially emitting fiber that is configured to radially emit bacterial disinfecting light to disinfect at least a portion of the first body.

Clause 3. The assembly according to clause 1, wherein the first optical fiber is a radially emitting fiber that is configured to radially emit bacterial disinfecting light to disinfect at least a portion of the second body.

Clause 4. The assembly according to clause 1, wherein the first optical fiber is a radially emitting fiber that is configured to radially emit bacterial disinfecting light to disinfect at least a portion of the first body and at least a portion of the second body.

Clause 5. The assembly according to clause 1, wherein the first optical fiber is an end emitting fiber that is configured to end emit bacterial disinfecting light to disinfect at least a portion of the first body.

Clause 6. The assembly according to clause 1, wherein the first optical fiber is a dual emitting fiber that is configured to radially emit bacterial disinfecting light to disinfect at least a portion of the first body.

Clause 7. The assembly according to clause 1, wherein the first optical fiber is a dual emitting fiber that is configured to radially emit bacterial disinfecting light to disinfect at least a portion of the first body and at least a portion of the second body.

Clause 8. The assembly according to clause 1, wherein the first optical fiber is a dual emitting fiber that is configured to radially emit bacterial disinfecting light to disinfect at least a first portion of the first body and to end emit bacterial disinfecting light to disinfect at least a second portion of the first body.

Clause 9. The assembly according to clause 1, wherein the first optical fiber is a dual emitting fiber that is configured to radially emit bacterial disinfecting light to disinfect at least a first portion of the first body and a portion of the second body and to end emit bacterial disinfecting light to disinfect at least a second portion of the first body.

Clause 10. The assembly according to clause 1, further comprising a second optical fiber that has a length, wherein the second body has a second channel that houses at least a portion of the length of the second optical fiber.

Clause 11. The assembly according to clause 10, wherein the first optical fiber is a radially emitting fiber that is configured to radially emit bacterial disinfecting light to disinfect at least a portion of the first body and the second optical fiber is a radially emitting fiber that is configured to radially emit bacterial disinfecting light to disinfect at least a first portion of the second body.

Clause 12. The assembly according to clause 11, wherein the first optical fiber is configured to radially emit bacterial disinfecting light to disinfect at least a second portion of the second body.

Clause 13. The assembly according to clause 10, wherein the first optical fiber is an end emitting fiber that is configured to end emit bacterial disinfecting light to disinfect at least a first portion of the first body, and the second optical fiber is a radially emitting fiber that is configured to radially emit bacterial disinfecting light to disinfect at least a second portion of the first body.

Clause 14. The assembly according to clause 10, wherein the first optical fiber is an end emitting fiber that is configured to end emit bacterial disinfecting light to disinfect at least a first portion of the first body, and the second optical fiber is a radially emitting fiber that is configured to radially emit bacterial disinfecting light to disinfect at least a second portion of the first body and a portion of the second body.

Clause 15. The assembly according to clause 10, wherein the first optical fiber is an end emitting fiber that is configured to end emit bacterial disinfecting light to disinfect at least a first portion of the first body, and the second optical fiber is also an end emitting fiber that is configured to end emit bacterial disinfecting light to disinfect at least a portion of the second body.

Clause 16. The assembly according to clause 10, wherein the second optical fiber is configured to end emit bacterial disinfecting light to disinfect at least a portion of the first body.

Clause 17. The assembly according to clause 10, wherein the first optical fiber is a dual emitting fiber that is configured to radially emit bacterial disinfecting light to disinfect at least a first portion of the first body and to end emit bacterial disinfecting light to disinfect at least a second portion of the first body, the second optical fiber being a dual emitting fiber that is configured to radially emit bacterial disinfecting light to disinfect at least a first portion of the second body and to end emit bacterial disinfecting light to disinfect at least a second portion of the second body.

Clause 18. The assembly according to clause 10, wherein the first optical fiber is a dual emitting fiber that is configured to radially emit bacterial disinfecting light to disinfect at least a first portion of the first body and to end emit bacterial disinfecting light to disinfect at least a second portion of the first body, the second optical fiber being a radially emitting fiber that is configured to radially emit bacterial disinfecting light to disinfect at least a portion of the second body.

Clause 19. The assembly according to clause 10, wherein the first optical fiber is a dual emitting fiber that is configured to radially emit bacterial disinfecting light to disinfect at least a first portion of the first body and to end emit bacterial disinfecting light to disinfect at least a second portion of the first body, the second optical fiber being an end emitting fiber that is configured to end emit bacterial disinfecting light to disinfect at least a portion of the second body.

Clause 20. The assembly according to clause 10, wherein a portion of the second channel overlaps a portion of the first channel.

Clause 21. The assembly according to clause 10, wherein the first body is a flexible structure and the second body is a rigid structure.

Clause 22. The assembly according to clause 1, wherein the first body is a flexible structure and the second body is a rigid structure.

Clause 23. The assembly according to clauses 1-22, wherein at least a portion of the first optical fiber is attached to the first body inside the receptacle.

Clause 24. The assembly according to clauses 1-22, wherein the first optical fiber is not attached to the first body and is slideable inside the receptacle.

Clause 25. The assembly according to clauses 1-24, wherein the at least second portion of the length of the first optical fiber is not held taut along at least a portion of the length of the first channel.

Clause 26. The assembly according to clauses 10-24, wherein the at least second portion of the length of the first optical fiber is not held taut along at least a portion of the length of the first channel and the at least second portion of the length of the second optical fiber is not held taut along at least a portion of the length of the second channel.

Clause 27. The assembly according to clause 10-22, wherein at least a portion of the length of the first channel and at least a portion of the length of the second channel reside at different heights inside the second body.

Clause 28. The assembly according to clause 10-22, wherein the second body comprises a raised platform that has side walls that at least partially define the first and second channels, the first optical fiber being routed inside the second body in a clockwise direction around the raised platform and the second optical fiber being routed inside the second body in a counter-clockwise direction around the raised platform.

Clause 29. The assembly according to clauses 5 and 13-19, further comprising one or more optical surfaces that direct the end emitted bacterial disinfecting light onto the first body.

Clause 30. The assembly according to clauses 15-17 and 19, further comprising one or more optical surfaces that direct the end emitted bacterial disinfecting light onto the second body.

Clause 31. The assembly according to clauses 1-27, wherein the first body and second body are respectively a main shaft and a hub of a central venous catheter.

Clause 32. The assembly according to clauses 1-27, wherein the first body and second body are respectively an infusion shaft and a hub of a central venous catheter.

Clause 33. The assembly according to clause 31, further comprising an infusion shaft, the infusion shaft and main shaft being fluidly coupled inside the hub by a conduit.

Clause 34. The assembly according to clause 33, wherein at least a portion of one of the first channel and second channel resides above, below or to the side of the conduit.

Clause 35. The assembly according to clauses 3, 5 and 7, wherein the end emitting fiber comprises at an end thereof a power density lowering end cap.

Clause 36. An assembly comprising:
an end emitting optical fiber having a length;
a body having formed therein a channel that houses at least a portion of the length of the end emitting optical fiber, the end emitting optical fiber configured to end emit bacterial disinfecting light to disinfect at least a portion of the first body.

Group C Clauses:

Clause 1. An assembly comprising:
a first optical fiber having a length and a first minimum bending radius;
a first body having a receptacle in which at least a first portion of the length of the first optical fiber resides;
a second body attached to the first body, the second body having formed therein a first channel that houses at least a second portion of the length of the first optical fiber, the first channel having a length and one or more bends along the length, each of the one or more bends having a radius of curvature that is equal to or greater than the first minimum bending radius of the first optical fiber.

Clause 2. The assembly according to clause 1, wherein the first optical fiber is a radially emitting fiber that is configured to radially emit bacterial disinfecting light to disinfect at least a portion of the first body.

Clause 3. The assembly according to clause 1, wherein the first optical fiber is a radially emitting fiber that is configured to radially emit bacterial disinfecting light to disinfect at least a portion of the second body.

Clause 4. The assembly according to clause 1, wherein the first optical fiber is a radially emitting fiber that is configured to radially emit bacterial disinfecting light to disinfect at least a portion of the first body and at least a portion of the second body.

Clause 5. The assembly according to clause 1, wherein the first optical fiber is an end emitting fiber that is configured to end emit bacterial disinfecting light to disinfect at least a portion of the first body.

Clause 6. The assembly according to clause 1, wherein the first optical fiber is a dual emitting fiber that is configured to radially emit bacterial disinfecting light to disinfect at least a portion of the first body.

Clause 7. The assembly according to clause 1, wherein the first optical fiber is a dual emitting fiber that is configured to radially emit bacterial disinfecting light to disinfect at least a portion of the first body and at least a portion of the second body.

Clause 8. The assembly according to clause 1, wherein the first optical fiber is a dual emitting fiber that is configured to radially emit bacterial disinfecting light to disinfect at least a first portion of the first body and to end emit bacterial disinfecting light to disinfect at least a second portion of the first body.

Clause 9. The assembly according to clause 1, wherein the first optical fiber is a dual emitting fiber that is configured to radially emit bacterial disinfecting light to disinfect at least a first portion of the first body and a portion of the second body and to end emit bacterial disinfecting light to disinfect at least a second portion of the first body.

Clause 10. The assembly according to clause 1, further comprising a second optical fiber that has a length and a second minimum bending radius, wherein the second body has a second channel that houses at least a portion of the length of the second optical fiber, the second channel having a length and one or more bends along the length, each of the one or more bends of the second channel having a radius of curvature that is equal to or greater than the second minimum bending radius of the second optical fiber.

Clause 11. The assembly according to clause 10, wherein the first optical fiber is a radially emitting fiber that is configured to radially emit bacterial disinfecting light to disinfect at least a portion of the first body and the second optical fiber is a radially emitting fiber that is configured to radially emit bacterial disinfecting light to disinfect at least a first portion of the second body.

Clause 12. The assembly according to clause 11, wherein the first optical fiber is configured to radially emit bacterial disinfecting light to disinfect at least a second portion of the second body.

Clause 13. The assembly according to clause 10, wherein the first optical fiber is an end emitting fiber that is configured to end emit bacterial disinfecting light to disinfect at least a first portion of the first body, and the second optical fiber is a radially emitting fiber that is configured to radially emit bacterial disinfecting light to disinfect at least a second portion of the first body.

Clause 14. The assembly according to clause 10, wherein the first optical fiber is an end emitting fiber that is configured to end emit bacterial disinfecting light to disinfect at least a first portion of the first body, and the second optical fiber is a radially emitting fiber that is configured to radially emit bacterial disinfecting light to disinfect at least a second portion of the first body and a portion of the second body.

Clause 15. The assembly according to clause 10, wherein the first optical fiber is an end emitting fiber that is configured to end emit bacterial disinfecting light to disinfect at least a first portion of the first body, and the second optical fiber is also an end emitting fiber that is configured to end emit bacterial disinfecting light to disinfect at least a portion of the second body.

Clause 16. The assembly according to clause 10, wherein the second optical fiber is also configured to end emit bacterial disinfecting light to disinfect at least a portion of the first body.

Clause 17. The assembly according to clause 10, wherein the first optical fiber is a dual emitting fiber that is configured to radially emit bacterial disinfecting light to disinfect at least a first portion of the first body and to end emit bacterial disinfecting light to disinfect at least a second portion of the first body, the second optical fiber being a dual emitting fiber that is configured to radially emit bacterial disinfecting light to disinfect at least a first portion of the second body and to end emit bacterial disinfecting light to disinfect at least a second portion of the second body.

Clause 18. The assembly according to clause 10, wherein the first optical fiber is a radially dual emitting fiber that is configured to radially emit bacterial disinfecting light to disinfect at least a first portion of the first body and to end emit bacterial disinfecting light to disinfect at least a second portion of the first body, the second optical fiber being a radially emitting fiber that is configured to radially emit bacterial disinfecting light to disinfect at least a portion of the second body.

Clause 19. The assembly according to clause 10, wherein the first optical fiber is a dual emitting fiber that is configured to radially emit bacterial disinfecting light to disinfect at least a first portion of the first body and to end emit bacterial disinfecting light to disinfect at least a second portion of the first body, the second optical fiber being an end emitting fiber that is configured to end emit bacterial disinfecting light to disinfect at least a portion of the second body.

Clause 20. The assembly according to clause 10, wherein a portion of the second channel overlaps a portion of the first channel.

Clause 21. The assembly according to clause 10, wherein the first body is a flexible structure and the second body is a rigid structure.

Clause 22. The assembly according to clause 1, wherein the first body is a flexible structure and the second body is a rigid structure.

Clause 23. The assembly according to clauses 1-22, wherein at least a portion of the first optical fiber is attached to the first body inside the receptacle.

Clause 24. The assembly according to clauses 1-22, wherein the first optical fiber is not attached to the first body and is slideable inside the receptacle.

Clause 25. The assembly according to clauses 1-24, wherein the at least second portion of the length of the first optical fiber is not held taut along at least a portion of the length of the first channel so that the first optical fiber possesses slack.

Clause 26. The assembly according to clauses 10-24, wherein the at least second portion of the length of the first optical fiber is not held taut along at least a portion of the length of the first channel and the at least second portion of the length of the second optical fiber is not held taut along at least a portion of the length of the second channel.

Clause 27. The assembly according to clause 10-22, wherein at least a portion of the length of the first channel and at least a portion of the length of the second channel reside at different heights inside the second body.

Clause 28. The assembly according to clause 10-22, wherein the second body comprises a raised platform that has side walls that at least partially define the first and second channels, the first optical fiber being routed inside the second body in a clockwise direction around the raised platform and the second optical fiber being routed inside the second body in a counter-clockwise direction around the raised platform.

Clause 29. The assembly according to clauses 5 and 13-19, further comprising one or more optical surfaces through which the end emitted bacterial disinfecting light passes before the bacterial disinfecting light is delivered to the first body.

Clause 30. The assembly according to clauses 15-17 and 19, further comprising one or more optical surfaces through which the end emitted bacterial disinfecting light passes before the bacterial disinfecting light is delivered to the first body.

Clause 31. The assembly according to clauses 1-27, wherein the first body and second body are respectively a main shaft and a hub of a central venous catheter.

Clause 32. The assembly according to clauses 1-27, wherein the first body and second body are respectively an infusion shaft and a hub of a central venous catheter.

Clause 33. The assembly according to clause 32, further comprising an infusion shaft, the infusion shaft and main shaft being fluidly coupled inside the hub by a conduit.

Clause 34. The assembly according to clause 33, wherein at least a portion of one of the first channel or second channel resides above, below or to the side of the tubular conduit.

Clause 35. An assembly comprising:
an end emitting optical fiber having a length and a minimum bending radius;
a body having formed therein a channel that houses at least a portion of the length of the end emitting optical fiber, the channel having a length and one or more bends along the length, each of the one or more bends having a radius of curvature that is equal to or greater than the minimum bending radius of the end emitting optical fiber, the end emitting optical fiber configured to end emit bacterial disinfecting light to disinfect at least a portion of the first body.

Group D Clauses:

Clause 1. An assembly comprising:
a first optical fiber having a length;
a first body having a receptacle in which at least a first portion of the length of the first optical fiber resides;
a second body in which a portion of the first body resides, the second body having formed therein a first channel that houses at least a second portion of the length of the first optical fiber;
wherein the at least second portion of the length of the first optical fiber is not held taut along at least a portion of the length of the first channel so that the first optical fiber possesses slack.

Clause 2. The assembly according to clause 1, wherein the first optical fiber is a radially emitting fiber that is configured to radially emit bacterial disinfecting light to disinfect at least a portion of the first body.

Clause 3. The assembly according to clause 1, wherein the first optical fiber is a radially emitting fiber that is configured to radially emit bacterial disinfecting light to disinfect at least a portion of the second body.

Clause 4. The assembly according to clause 1, wherein the first optical fiber is a radially emitting fiber that is configured to radially emit bacterial disinfecting light to disinfect at least a portion of the first body and at least a portion of the second body.

Clause 5. The assembly according to clause 1, wherein the first optical fiber is an end emitting fiber that is configured to end emit bacterial disinfecting light to disinfect at least a portion of the first body.

Clause 6. The assembly according to clause 1, wherein the first optical fiber is a dual emitting fiber that is configured to radially emit bacterial disinfecting light to disinfect at least a portion of the first body.

Clause 7. The assembly according to clause 1, wherein the first optical fiber is a dual emitting fiber that is configured to radially emit bacterial disinfecting light to disinfect at least a portion of the first body and at least a portion of the second body.

Clause 8. The assembly according to clause 1, wherein the first optical fiber is a dual emitting fiber that is configured to radially emit bacterial disinfecting light to disinfect at least a first portion of the first body and to end emit bacterial disinfecting light to disinfect at least a second portion of the first body.

Clause 9. The assembly according to clause 1, wherein the first optical fiber is a dual emitting fiber that is configured to radially emit bacterial disinfecting light to disinfect at least a first portion of the first body and a portion of the second body, and to end emit bacterial disinfecting light to disinfect at least a second portion of the first body.

Clause 10. The assembly according to clause 1, further comprising a second optical fiber that has a length and the second body has a second channel that houses at least a portion of the length of the second optical fiber;

wherein the at least second portion of the length of the first optical fiber is not held taut along at least a portion of the length of the first channel and the at least second portion of the length of the second optical fiber is not held taut along at least a portion of the length of the second channel.

Clause 11. The assembly according to clause 10, wherein the first optical fiber is a radially emitting fiber that is configured to radially emit bacterial disinfecting light to disinfect at least a portion of the first body and the second optical fiber is a radially emitting fiber that is configured to radially emit bacterial disinfecting light to disinfect at least a first portion of the second body.

Clause 12. The assembly according to clause 11, wherein the first optical fiber is configured to radially emit bacterial disinfecting light to disinfect at least a second portion of the second body.

Clause 13. The assembly according to clause 10, wherein the first optical fiber is an end emitting fiber that is configured to end emit bacterial disinfecting light to disinfect at least a first portion of the first body, and the second optical fiber is a radially emitting fiber that is configured to radially emit bacterial disinfecting light to disinfect at least a second portion of the first body.

Clause 14. The assembly according to clause 10, wherein the first optical fiber is an end emitting fiber that is configured to end emit bacterial disinfecting light to disinfect at least a first portion of the first body, and the second optical fiber is a radially emitting fiber that is configured to radially emit bacterial disinfecting light to disinfect at least a second portion of the first body and a portion of the second body.

Clause 15. The assembly according to clause 10, wherein the first optical fiber is an end emitting fiber that is configured to end emit bacterial disinfecting light to disinfect at least a first portion of the first body, and the second optical fiber is also an end emitting fiber that is configured to end emit bacterial disinfecting light to disinfect at least a portion of the second body.

Clause 16. The assembly according to clause 10, wherein the second optical fiber is also configured to end emit bacterial disinfecting light to disinfect at least a portion of the first body.

Clause 17. The assembly according to clause 10, wherein the first optical fiber is a dual emitting fiber that is configured to radially emit bacterial disinfecting light to disinfect at least a first portion of the first body and to end emit bacterial disinfecting light to disinfect at least a second portion of the first body, the second optical fiber being a dual emitting fiber that is configured to radially emit bacterial disinfecting light to disinfect at least a first portion of the second body and to end emit bacterial disinfecting light to disinfect at least a second portion of the second body.

Clause 18. The assembly according to clause 10, wherein the first optical fiber is a dual emitting fiber that is configured to radially emit bacterial disinfecting light to disinfect at least a first portion of the first body and to end emit bacterial disinfecting light to disinfect at least a second portion of the first body, the second optical fiber being a radially emitting fiber that is configured to radially emit bacterial disinfecting light to disinfect at least a portion of the second body.

Clause 19. The assembly according to clause 10, wherein the first optical fiber is a dual emitting fiber that is configured to radially emit bacterial disinfecting light to disinfect at least a first portion of the first body and to end emit bacterial disinfecting light to disinfect at least a second portion of the first body, the second optical fiber being an end emitting fiber that is configured to end emit bacterial disinfecting light to disinfect at least a portion of the second body.

Clause 20. The assembly according to clause 10, wherein a portion of the second channel overlaps a portion of the first channel.

Clause 21. The assembly according to clause 10, wherein the first body is a flexible structure and the second body is a rigid structure.

Clause 22. The assembly according to clause 1, wherein the first body is a flexible structure and the second body is a rigid structure.

Clause 23. The assembly according to clauses 1-22, wherein at least a portion of the first optical fiber is attached to the first body inside the receptacle.

Clause 24. The assembly according to clauses 1-22, wherein the first optical fiber is not attached to the first body and is slideable inside the receptacle.

Clause 25. The assembly according to clause 10-22, wherein at least a portion of the length of the first channel and at least a portion of the length of the second channel reside at different heights inside the second body.

Clause 26. The assembly according to clause 10-22, wherein the second body comprises a raised platform that has side walls that at least partially define the first and second channels, the first optical fiber being routed inside the second body in a clockwise direction around the raised platform and the second optical fiber being routed inside the second body in a counter-clockwise direction around the raised platform.

Clause 27. The assembly according to clauses 5 and 13-19, further comprising one or more optical surfaces through which the end emitted bacterial disinfecting light passes before the bacterial disinfecting light is delivered to the first body.

Clause 28. The assembly according to clauses 15-17 and 19, further comprising one or more optical surfaces through which the end emitted bacterial disinfecting light passes before the bacterial disinfecting light is delivered to the first body.

Clause 29. The assembly according to clauses 1-26, wherein the first body and second body are respectively a main shaft and a hub of a central venous catheter.

Clause 30. The assembly according to clauses 1-26, wherein the first body and second body are respectively an infusion shaft and a hub of a central venous catheter.

Clause 31. The assembly according to clause 29, further comprising an infusion shaft, the infusion shaft and main shaft being fluidly coupled inside the hub by a conduit.

Clause 32. The assembly according to clause 31, wherein at least a portion of one of the first channel or second channel resides above, below or to the side of the conduit.

Clause 33. An assembly comprising:
an end emitting optical fiber having a length;
a body having formed therein a channel that houses at least a portion of the length of the end emitting optical fiber, the end emitting optical fiber being configured to end emit bacterial disinfecting light to disinfect at least a portion of the second body;
wherein the at least portion of the length of the end emitting optical fiber is not held taut along at least a portion of the length of the channel.

Group E Clauses:

Clause 1. An assembly comprising:
an end emitting optical fiber having a length and configured to end emit bacterial disinfecting light;
a body having a receptacle in which at least a portion of the length of the end emitting optical fiber resides, the body having a disinfecting target area located therein;
one or more surfaces disposed on or in the body onto which the end emitted bacterial disinfecting light is configured to impinge when the end emitting light is activated, the one or more surfaces being configured to alter the trajectory of the disinfecting light so that the disinfecting light is directed toward the disinfecting target area via a disinfecting light pathway.

Clause 2. The assembly according to clause 1, wherein at least one of the one or more surfaces comprises a refractive optical surface.

Clause 3. The assembly according to clause 1, wherein at least one of the one or more surfaces comprises a total internal reflection optical surface.

Clause 4. The assembly according to clause 1, wherein at least one of the one or more surfaces comprises a light reflector.

Clause 5. The assembly according to clause 1, wherein the one or more surfaces comprise a refractive optical surface and a total internal reflection optical surface.

Clause 6. The assembly according to clause 1, wherein the one or more surfaces comprise a refractive optical surface and a light reflector.

Clause 7. The assembly according to clause 1, wherein the one or more surfaces comprise a total internal reflection optical surface and a light reflector.

Clause 8. The assembly according to clause 1, wherein the one or more surfaces comprise a refractive optical surface, a total internal reflection optical surface and a light reflector.

Clause 9. The assembly according to clause 2, wherein the at least one refractive optical surface is configured to collimate the disinfecting light.

Clause 10. The assembly according to clause 2, wherein the least one refractive optical surface is configured to converge the disinfecting light.

Clause 11. The assembly according to clause 2, wherein the least one refractive optical surface is configured to diverge the disinfecting light.

Clause 12. The assembly according to clause 2, wherein the least one refractive optical surface is flat.

Clause 13. The assembly according to clause 2, wherein the least one refractive optical surface has a semi-spherical shape.

Clause 14. The assembly according to clause 2, wherein the least one refractive optical surface has an a-spherical shape.

Clause 15. The assembly according to clause 5, wherein the refractive optical surface precedes the total internal reflection optical surface in the disinfecting light pathway.

Clause 16. The assembly according to clause 6, wherein the refractive optical surface precedes the light reflector in the disinfecting light pathway.

Clause 17. The assembly according to clause 7, wherein the total internal reflection optical surface precedes the light reflector in the disinfecting light pathway.

Clause 18. The assembly according to clause 8, wherein the refractive optical surface precedes the total internal reflection optical surface which precedes the light reflector in the disinfecting light pathway.

Clause 19. The assembly according to clause 2, wherein the end emitting optical fiber comprises a core having an end with there being an index matching material disposed between the end of the core and the refractive optical surface.

Clause 20. The assembly according to clause 19, wherein the index matching material is an adhesive that secures the end emitting optical fiber to the body.

Clause 21. The assembly according to clause 1, wherein the body comprises a part of an infusion shaft of a central venous catheter.

Clause 22. The assembly according to clause 21, wherein the part comprises a proximal connector of the infusion shaft.

Clause 23. The assembly according to clauses 1-22, wherein the end emitting fiber comprises at an end thereof a power density lowering end cap.

Group F Clauses:

Clause 1. An assembly comprising:
an elongate shaft having a longitudinal axis and an outer surface;
a radially emitting fiber spirally disposed inside the elongate shaft;
a plurality of through holes located between the radially emitting fiber and the outer surface, the through holes being longitudinally spaced-apart from one another;
a laser optically coupled with the radially emitting fiber;
a controller operatively coupled to the laser and configured to cause the laser to deliver pulsed light with a pulsed width into the radially emitting fiber, a longitudinal distance between adjacent through holes being such that the pulse width is shorter than a time for the light to travel between the adjacent through holes.

Clause 2. The assembly according to clause 1, further comprising a back reflectance detector that is optically coupled to the radially emitting fiber and configured to receive back reflected light pulses from the radially emitting fiber.

Clause 3. The assembly according to clause 2, wherein the light source is a laser that is optically coupled to the radially emitting fiber and configured to deliver the pulsed light to the radially emitting fiber via a mirror.

Clause 4. The assembly according to clause 3, wherein the mirror is also configured to direct the back reflected light pulses to the back reflectance detector.

Clause 5. The assembly according to clause 2, wherein the back reflectance detector is configured to generate data based upon the back reflected light pulses received in the back reflectance detector.

Clause 6. The assembly according to clause 5, wherein the back reflectance detector comprises means for comparing the data with baseline data to determine if an unwanted substance exists on the outer surface of the elongate shaft.

Clause 7. The assembly according to clause 5, wherein the back reflectance detector comprises means for processing the data to form an image that can be used to determine if an unwanted substance exists on the outer surface of the elongate shaft.

Clause 8. The assembly according to clause 6, wherein the unwanted substance is a biofilm or a clot.

Clause 9. The assembly according to clause 1, wherein the elongate shaft comprises a wall that extends between an inner surface and the outer surface, the inner surface defining a lumen that runs along a length of the elongate shaft.

Clause 10. The assembly according to clause 1, wherein the radially emitting fiber is fixed inside the elongate shaft.

Clause 11. The assembly according to clause 1, wherein the radially emitting fiber is disposed inside a spiral lumen inside a length of the elongate shaft, the radially emitting fiber being slideable inside the lumen.

Clause 12. The assembly according to clause 1 comprising a single radially emitting fiber.

Clause 13. The assembly according to clause 1, wherein the radially emitting fiber is located nearer the outer surface of the elongate shaft than to the longitudinal axis of the elongate shaft.

Clause 14. The assembly according to clause 1, wherein the laser is configured to emit red light.

Clause 15. A method of determining the presence of an unwanted substance on the outer surface of an elongate shaft, the elongate shaft including a longitudinal axis, an outer surface, a radially emitting fiber spirally disposed inside the elongate shaft, and a plurality of through holes located between the radially emitting fiber and the outer surface, the through holes being longitudinally spaced-apart from one another, the method comprising:

emitting pulsed light having a pulsed width from the radially emitting fiber so that at least a portion of the pulsed light is delivered through the plurality of through holes;

sequentially receiving in the radially emitting fiber through the plurality of through holes a plurality of back reflected light pulses;

delivering the plurality of back reflected light pulses to a back reflective detector;

generating data that correlates with the plurality of back reflected light pulses.

Clause 16. The method according to clause 15, further comprising comparing the data with baseline data to determine if an unwanted substance exists on the outer surface of the elongate shaft.

Clause 17. The method according to clause 15, further comprising means for processing the data to form an image that can be used to determine if an unwanted substance exists on the outer surface of the elongate shaft.

Clause 18. The method according to clause 15, wherein the elongate shaft has a proximal end and a distal end, and the plurality of through holes includes a proximal-most through hole, a distal-most through hole and one or more through holes dispersed there between, the plurality of back reflected pulses being delivered to the back reflective detector sequentially beginning with the back reflected pulse received in the radially emitting fiber through the proximal-most through hole and ending with the back reflected pulse received in the radially emitting fiber through the distal-most through hole.

Clause 19. The method according to clause 15, further comprising delivery light from a laser to the radially emitting fiber via a mirror and delivering the plurality of back reflected pulses to the back reflectance detector via the mirror.

Clause 20. The method according to clause 19, wherein the light is red light.

Group G Clauses:

Clause 1. A hub comprising:

a first optical fiber, the first optical fiber having a length and a first minimum bending radius;

a first channel that houses at least a portion of the length of the first optical fiber, the first channel having a length and one or more bends along the length, each of the one or more bends having a radius of curvature that is equal to or greater than the first minimum bending radius of the first optical fiber.

Clause 2. The hub according to clause 1, wherein the first optical fiber is a radially emitting fiber that is configured to emit bacterial disinfecting light to disinfect at least a portion of the hub.

Clause 3. The hub according to clause 1, wherein the first optical fiber is an end emitting fiber that is configured to emit bacterial disinfecting light to disinfect at least a portion of the hub.

Clause 4 The hub according to clause 3, further comprising a proximal end portion of a main shaft, the main shaft including a working lumen that has a proximal opening located inside the hub, the end emitting fiber being configured to the emit bacterial disinfecting light to disinfect at least a portion of the proximal end portion of the main shaft.

Clause 5. The hub according to clause 1, further comprising:

a distal end portion of an infusion shaft, the infusion shaft including a working lumen that has a distal opening located inside the hub;

a proximal end portion of a main shaft, the main shaft including a working lumen that has a proximal opening located inside the hub;

a conduit that fluidly couples the distal opening of the working lumen of the infusion shaft to the proximal opening of the working lumen of the main shaft, the conduit having a length;

at least a portion of the length of the first channel that houses the first optical fiber being located above, below or to the side of at least a portion of the length of the conduit.

Clause 6. The hub according to clause 5, wherein the first optical fiber is a radially emitting fiber that is configured to emit a bacterial disinfecting light and to expose the conduit to the bacterial disinfecting light.

Clause 7. The hub according to clause 1, further comprising:

a distal end portion of an infusion shaft, the infusion shaft including a working lumen that has a distal opening located inside the hub;

a proximal end portion a main shaft, the main shaft including a working lumen that has a proximal opening located inside the hub;

a conduit that fluidly couples the distal opening of the working lumen of the infusion shaft to the proximal opening of the working lumen of the main shaft, the conduit having a length;

wherein the first optical fiber is an end emitting fiber that is configured to emit bacterial disinfecting light to disinfect at least a portion of the hub.

Clause 8. The hub according to clause 6, wherein the conduit comprises a tubular body that is transparent or translucent to the bacterial disinfecting light.

Clause 9. The hub according to clause 1, further comprising:

a distal end portion of an infusion shaft, the infusion shaft including a working lumen that has a distal opening located inside the hub;

a proximal end portion a main shaft, the main shaft including a working lumen that has a proximal opening located inside the hub;

a conduit that fluidly couples the distal opening of the working lumen of the infusion shaft to the proximal opening of the working lumen of the main shaft, the conduit having a length;

at least a portion of the length of the first channel that houses the first optical fiber being located above or below at least a portion of a length of the working lumen located in the distal portion of the infusion shaft.

Clause 10. The hub according to clause 9, wherein the first optical fiber is a radially emitting fiber that is configured to emit a bacterial disinfecting light and to expose the at least portion of the length of the working lumen of the infusion shaft to the bacterial disinfecting light.

Clause 11. The hub according to clause 9, wherein the first optical fiber is an end emitting fiber that is configured to emit a bacterial disinfecting light and to expose the at least portion of the length of the working lumen of the infusion shaft to the bacterial disinfecting light.

Clause 12. The hub according to clause 10, wherein the at least portion of the length of the working lumen of the infusion shaft resides inside a tubular body that is transparent or translucent to the bacterial disinfecting light.

Clause 13. The hub according to clause 11, wherein the at least portion of the length of the working lumen of the infusion shaft resides inside a tubular body, the tubular body having an opening through which the bacterial disinfecting light is configured to propagate into the working lumen.

Clause 14. The hub according to clause 11, further comprising one or more optical surfaces through which the bacterial disinfecting light emitted by the end emitting fiber passes before the bacterial disinfecting light is delivered to the at least portion of the length of the working lumen of the infusion shaft.

Clause 15. The hub according to clause 5, wherein the distal end portion of the infusion shaft includes a fiber lumen that contains at least a portion of the first optical fiber.

Clause 16. The hub according to clause 15, wherein the first optical fiber is a radially emitting fiber that is configured to emit bacterial disinfecting light.

Clause 17. The hub according to clause 15, wherein the first optical fiber is an end emitting fiber that is configured to emit bacterial disinfecting light.

Clause 18. The hub according to clause 9, wherein the proximal end portion of the main shaft includes a fiber lumen that contains at least a portion of the first optical fiber.

Clause 19. The hub according to clause 18, wherein the first optical fiber is a radially emitting fiber that is configured to emit bacterial disinfecting light.

Clause 20. The hub according to clause 18, wherein the first optical fiber is an end emitting fiber that is configured to emit bacterial disinfecting light.

Clause 21. The hub according to clause 5, further comprising:

a second optical fiber, the second optical fiber having a length and a second minimum bending radius;

a second channel that houses at least a portion of the length of the second optical fiber, the second channel having a length and one or more bends along the length, each of the one or more bends having a radius of curvature that is equal to or greater than the second minimum bending radius of the second optical fiber;

at least a portion of the length of the second channel that houses the second optical fiber being located above or below at least a portion of a length of the working lumen located in the distal portion of the infusion shaft.

Clause 22. The hub according to clause 21, wherein at least a portion of the length of the first channel and at least a portion of the length of the second channel overlap.

Clause 23. The hub according to clause 21, wherein at least a portion of the length of the second channel resides vertically above at least a portion of the length of the first channel.

Clause 24. The hub according to clause 21, wherein each of the first and second optical fibers is a radially emitting fiber that is configured to emit bacterial disinfecting light.

Clause 25. The hub according to clause 21, wherein each of the first and second optical fibers is an end emitting fiber that is configured to emit bacterial disinfecting light.

Clause 26. The hub according to clause 21, wherein the first optical fiber is a radially emitting fiber that is configured to emit bacterial disinfecting light and the second optical fiber is an end-emitting fiber that is configured to emit bacterial emitting light.

Clause 27. The hub according to clause 24, wherein the proximal end portion of the main shaft includes a fiber lumen that contains at least a portion of the second optical fiber.

Clause 28. The hub according to clause 24, wherein the distal end portion of the infusion shaft includes a fiber lumen that contains at least a portion of the first optical fiber.

Clause 29. The hub according to clause 27, wherein the distal end portion of the infusion shaft includes a fiber lumen that contains at least a portion of the first optical fiber.

Clause 30. The hub according to clause 1, further comprising:

a distal end portion of an infusion shaft, the infusion shaft including a working lumen that has a distal opening located inside the hub;

a proximal end portion a main shaft, the main shaft including a working lumen that has a proximal opening located inside the hub, the proximal end portion of the main shaft having a fiber lumen;

a conduit that fluidly couples the distal opening of the working lumen of the infusion shaft to the proximal opening of the working lumen of the main shaft, the conduit having a length;

wherein the first optical fiber is an imaging fiber, at least a portion of a length of the imaging fiber residing inside the fiber lumen.

Clause 31. The hub according to clause 1, wherein the first optical fiber is not held taut along at least a portion of the length of the first channel.

Clause 32. The hub according to clause 5, wherein the first optical fiber is not held taut along at least a portion of the length of the first channel.

Clause 33. The hub according to clause 21, wherein the first optical fiber is not held taut along at least a portion of the length of the first channel and the second optical fiber is not held taut along at least a portion of the length of the second channel.

Group H Clauses:

Clause 1. An assembly comprising:

a polymeric body having walls that define a working lumen and a fiber lumen, the polymeric body having a first part in which the working lumen resides and a second part in which the fiber lumen resides, the first part having a first external shape and the second part having a second external shape that is different from the first shape, the polymeric body having an external profile defined by a perimeter of the first and second parts: and a clamp transitional between an open position and a closed position, in the closed position the clamp applies a force on the second part of the polymeric body to cause a deformation of the first part to cause a full or partial closure of the working lumen, the clamp having a proximal wall and a distal wall, at least one of the proximal and distal walls having a through opening that has an internal profile that is substantially similar to the external profile of the polymeric body, at least a portion of the polymeric body residing in the through opening so that the polymeric body is prevented from rotating in the clamp.

Clause 2. The assembly according to clause 1, further comprising an optical fiber residing in the fiber lumen.

Clause 3. The assembly according to clause 1, wherein the working lumen is defined by a top wall having a first thickness, a bottom wall having a second thickness and first and second side walls that each have a third thickness, the first and second side walls being located between the top and bottom walls, the third thickness being less than both the first and second thicknesses, the dimensional characteristics of the top wall, bottom wall and first and second side walls result in a bending of the first and second side walls when a downward force is applied to the top wall by the clamp, the bending allowing an inner surface of the top wall to contact an inner surface of the bottom wall to effectuate the full or partial closure of the working lumen.

Clause 4. The assembly according to clause 1, wherein a wall segment that defines at least in part the fiber lumen protrudes into the working lumen.

Clause 5. The assembly according to clause 3, wherein a wall segment that defines at least in part the fiber lumen protrudes into the working lumen.

Clause 6. The assembly according to clause 5, wherein the inner surface of the top wall includes a recess that is configured to mate with the protruding wall segment.

Clause 7. The assembly according to clause 2, wherein the first optical fiber is a radially emitting fiber.

Clause 8. The assembly according to clause 2, wherein the first optical fiber is an end emitting fiber.

Clause 9. The assembly according to clause 1, wherein the clamp includes an upper pad and a lower pad, the lower pad including a groove in which at least a portion of the first part of the polymeric body resides.

Clause 10. The assembly according to clause 9, wherein the first part and the groove are configured to inhibit a rotating of the polymeric body in the clamp.

Clause 11. The assembly according to clause 9, wherein when clamp is in the open position the upper pad does not press against the polymeric body and when the clamp is in the closed position the upper pad presses downward on the polymeric body, the clamp being continuously urged in the open direction.

Clause 12. The assembly according to clause 11, wherein the clamp includes a latch assembly to hold the clamp in the closed position.

Clause 13. The assembly according to clause 9, wherein the clamp includes a base onto which the lower pad is attached and an arm onto which the upper pad is attached, the arm being joined to the base by the proximal wall.

Clause 14. The assembly according to clause 13, wherein the proximal wall includes a hinge.

Clause 15. The assembly according to clause 1, wherein the polymeric body is an infusion shaft of a central venous catheter.

Clause 16. The assembly according to clause 1, wherein each of the proximal and distal walls have a through opening that has an internal profile that is substantially similar to the external profile of the polymeric body, at least a portion of the polymeric body residing in each of the through openings so that the polymeric body is prevented from rotating in the clamp.

Clause 17. The assembly according to clause 11, wherein the clamp further comprises a stop to limit the amount by which the upper pad can be pressed against the polymeric body.

Clause 18. The assembly according to clause 13, wherein a bottom of the base includes one or more slip resistant grips.

Clause 19. The assembly according to clause 13, wherein a top of the arm includes one or more slip resistant grips.

Clause 20. The assembly according to clause 15 wherein the infusion shaft includes a proximal connector, the clamp being directly attached to the proximal connector.

Clause 21. An assembly comprising:

a polymeric body having walls that define a first working lumen, a second working lumen and a fiber lumen, the fiber lumen being located inside a septum that separates the first and second working lumens, the polymeric body having a first part in which the first working lumen, second working lumen and fiber lumen reside, the polymeric body having a second part that protrudes radially from the first part, the first part having a first external shape and the second part having a second external shape that is different from the first shape, the polymeric body having an external profile defined by a perimeter of the first and second parts; and a clamp that is transitional between an open position and a closed position, in the closed position the clamp applies a force on the second part of the polymeric body to cause a deformation of the first part to cause a full or partial closure of at least one of the first and second working lumens, the clamp having a proximal wall and a distal wall, at least one of the proximal and distal walls having a through opening that has an internal profile that is substantially similar to the external profile of the polymeric body, at least a portion of the polymeric body residing in the through opening so that the polymeric body is prevented from rotating in the clamp.

Clause 22. The assembly according to clause 21, further comprising an optical fiber residing in the fiber lumen.

Clause 23. The assembly according to clause 21, wherein a part of the septum that defines the fiber lumen protrudes into one or both of the first and second working lumens.

Clause 24. The assembly according to clause 22, wherein the first optical fiber is a radially emitting fiber.

Clause 25. The assembly according to clause 22, wherein the first optical fiber is an end emitting fiber.

Clause 26. The assembly according to clause 21, wherein the clamp is continuously urged in the open direction and includes a latch assembly to hold the clamp in the closed position.

Clause 27. The assembly according to clause 21, wherein the clamp includes a base and an arm that is joined to the base by the proximal wall the through opening of the proximal wall having an internal profile that is substantially similar to the external profile of the polymeric body.

Clause 28. The assembly according to clause 27, wherein the proximal wall includes a hinge.

Clause 29. The assembly according to clause 21, wherein the polymeric body is an infusion shaft of a central venous catheter.

Clause 30. The assembly according to clause 21, wherein each of the proximal and distal walls have a through opening that has an internal profile that is substantially similar to the external profile of the polymeric body, at least a portion of the polymeric body residing in each of the through openings so that the polymeric body is prevented from rotating in the clamp.

What is claimed is:

1. A central venous catheter comprising:
   a main shaft having a proximal end portion and a distal end portion, the distal end portion configured for placement inside a patient, the main shaft having a working lumen;
   a first infusion shaft having a proximal end and a distal end, the first infusion shaft having a working lumen;
   a first end emitting fiber having a length and being configured to end emit bacterial disinfecting light;
   a hub, the distal end of the first infusion shaft being coupled to the proximal end portion of the main shaft by a first conduit located inside the hub, the first conduit fluidly connecting the working lumen of the first infusion shaft with the working lumen of the main shaft, the first end emitting fiber being arranged in the hub so that when bacterial disinfecting light is end emitted from the first end emitting fiber the bacterial disinfecting light impinges on the first conduit, the hub including a first channel that houses at least a portion of the length of the first end emitting fiber, the first channel being located outside the first conduit.

2. The central venous catheter according to claim 1, wherein the first conduit comprises a body that is transparent or translucent to the bacterial disinfecting light.

3. The central venous catheter according to claim 2, wherein an end of the first end emitting fiber through which the bacterial disinfecting light emits is spaced apart from the first conduit.

4. The central venous catheter according to claim 1, wherein an end of the first end emitting fiber through which the bacterial disinfecting light emits is spaced apart from the first conduit.

5. The central venous catheter according to claim 1, wherein the first end emitting fiber comprises at an end thereof a power density lowering end cap.

6. The central venous catheter according to claim 5, wherein the first conduit comprises a body that is transparent or translucent to the bacterial disinfecting light.

7. The central venous catheter according to claim 5, wherein the power density lowering end cap is spaced apart from the first conduit.

8. A central venous catheter comprising:
   a main shaft having a proximal end portion and a distal end portion, the distal end portion configured for placement inside a patient, the main shaft having a working lumen;
   a first infusion shaft having a proximal end and a distal end, the first infusion shaft having a working lumen;
   a first end emitting fiber having a length and being configured to end emit bacterial disinfecting light;
   a hub, the distal end of the first infusion shaft being coupled to the proximal end portion of the main shaft by a first conduit located inside the hub, the first conduit fluidly connecting the working lumen of the first infusion shaft with the working lumen of the main shaft, the first end emitting fiber being arranged in the hub so that when bacterial disinfecting light is end emitted from the first end emitting fiber the bacterial disinfecting light impinges on the first conduit;
   a second infusion shaft having a proximal end and a distal end, the second infusion shaft having a working lumen;
   a second end emitting fiber having a length and being configured to end emit bacterial disinfecting light;
   the distal end of the second infusion shaft being coupled to the proximal end portion of the main shaft by a second conduit located inside the hub, the second conduit fluidly connecting the working lumen of the second infusion shaft with the working lumen of the main shaft, the second end emitting fiber being arranged in the hub so that when bacterial disinfecting light is end emitted from the second end emitting fiber the bacterial disinfecting light impinges on the second conduit.

9. The central venous catheter according to claim 8, wherein the second conduit comprises a body that is transparent or translucent to the bacterial disinfecting light.

10. The central venous catheter according to claim 9, wherein an end of the second end emitting fiber through which the bacterial disinfecting light emits is spaced apart from the second conduit.

11. The central venous catheter according to claim 9, wherein the hub includes a second channel that houses at least a portion of the length of the second end emitting fiber, the second channel being located outside the second conduit.

12. The central venous catheter according to claim 8, wherein an end of the second end emitting fiber through which the bacterial disinfecting light emits is spaced apart from the second conduit.

13. The central venous catheter according to claim 8, wherein the hub includes a second channel that houses at least a portion of the length of the second end emitting fiber, the second channel being located outside the second conduit.

14. The central venous catheter according to claim 8, wherein the second end emitting fiber comprises at an end thereof a power density lowering end cap.

15. The central venous catheter according to claim 14, wherein the second conduit comprises a body that is transparent or translucent to the bacterial disinfecting light.

16. The central venous catheter according to claim 14, wherein the power density lowering end cap is spaced apart from the second conduit.

* * * * *